(12) United States Patent
Salamat-Miller et al.

(10) Patent No.: US 9,770,410 B2
(45) Date of Patent: *Sep. 26, 2017

(54) METHODS AND COMPOSITIONS FOR CNS DELIVERY OF ARYLSULFATASE A

(75) Inventors: Nazila Salamat-Miller, Arlington, MA (US); Katherine Taylor, Arlington, MA (US); Paul Campolieto, Charlottesville, VA (US); Zahra Shahrokh, Weston, MA (US); Jing Pan, Boxborough, MA (US); Lawrence Charnas, Natick, MA (US); Teresa Leah Wright, Lexington, MA (US); Pericles Calias, Melrose, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 158 days.

This patent is subject to a terminal disclaimer.

(21) Appl. No.: 13/168,963

(22) Filed: Jun. 25, 2011

(65) Prior Publication Data
US 2012/0009171 A1    Jan. 12, 2012

Related U.S. Application Data

(60) Provisional application No. 61/358,857, filed on Jun. 25, 2010, provisional application No. 61/360,786, (Continued)

(51) Int. Cl.
*A61K 38/54* (2006.01)
*A61K 9/00* (2006.01)
(Continued)

(52) U.S. Cl.
CPC ............ *A61K 9/0085* (2013.01); *A61K 9/19* (2013.01); *A61K 38/465* (2013.01); *A61K 47/02* (2013.01);
(Continued)

(58) Field of Classification Search
None
See application file for complete search history.

(56) References Cited

U.S. PATENT DOCUMENTS

| 4,743,265 A | 5/1988 | Whitehouse et al. |
| 5,972,333 A | 10/1999 | Hopwood et al. |

(Continued)

FOREIGN PATENT DOCUMENTS

| RU | 2209080 C2 | 7/2003 |
| WO | WO 02/087510 | 11/2002 |

(Continued)

OTHER PUBLICATIONS

Matzner et al., Hum. Mol. Gen. 14(9): 1139-1152 (2005).*
(Continued)

*Primary Examiner* — Erin M Bowers
(74) *Attorney, Agent, or Firm* — Proskauer Rose LLP; Fangli Chen

(57) ABSTRACT

The present invention provides, among other things, compositions and methods for CNS delivery of lysosomal enzymes for effective treatment of lysosomal storage diseases. In some embodiments, the present invention includes a stable formulation for direct CNS intrathecal administration comprising an arylsulfatase A (ASA) protein, salt, and a polysorbate surfactant for the treatment of Metachromatic Leukodystrophy Disease.

32 Claims, 42 Drawing Sheets

Related U.S. Application Data filed on Jul. 1, 2010, provisional application No. 61/387,862, filed on Sep. 29, 2010, provisional application No. 61/435,710, filed on Jan. 24, 2011, provisional application No. 61/442,115, filed on Feb. 11, 2011, provisional application No. 61/476,210, filed on Apr. 15, 2011, provisional application No. 61/495,268, filed on Jun. 9, 2011.

(51) Int. Cl.
*A61K 9/19* (2006.01)
*A61K 38/46* (2006.01)
*A61K 47/02* (2006.01)
*A61K 47/26* (2006.01)

(52) U.S. Cl.
CPC ...... *A61K 47/26* (2013.01); *C12Y 301/06013* (2013.01); *A61K 9/0019* (2013.01)

(56) References Cited

U.S. PATENT DOCUMENTS

| | | | |
|---|---|---|---|
| 6,118,045 | A | 9/2000 | Reuser et al. |
| 6,217,552 | B1 | 4/2001 | Barbut et al. |
| 6,534,300 | B1 | 3/2003 | Canfield |
| 6,537,785 | B1 | 3/2003 | Canfield |
| 7,351,410 | B2 | 4/2008 | van Bree et al. |
| 7,396,811 | B2 | 7/2008 | LeBowitz et al. |
| 7,442,372 | B2 | 10/2008 | Kakkis |
| 7,560,424 | B2 | 7/2009 | LeBowitz et al. |
| 7,629,309 | B2 | 12/2009 | LeBowitz et al. |
| 8,545,837 | B2 | 10/2013 | Zhu et al. |
| 2002/0052311 | A1 | 5/2002 | Solomon et al. |
| 2002/0099025 | A1 | 7/2002 | Heywood |
| 2003/0072761 | A1 | 4/2003 | LeBowitz |
| 2003/0082176 | A1 | 5/2003 | LeBowitz et al. |
| 2004/0005309 | A1 | 1/2004 | LeBowitz et al. |
| 2004/0006008 | A1 | 1/2004 | LeBowitz et al. |
| 2004/0172665 | A1 | 9/2004 | Reuser et al. |
| 2004/0243058 | A1 | 12/2004 | Barbut et al. |
| 2004/0248262 | A1 | 12/2004 | Koeberl et al. |
| 2005/0042227 | A1 | 2/2005 | Zankel et al. |
| 2005/0048047 | A1* | 3/2005 | Kakkis .............. A61K 38/47 424/94.61 |
| 2005/0208090 | A1 | 9/2005 | Keimel et al. |
| 2005/0244400 | A1 | 11/2005 | LeBowitz et al. |
| 2005/0281805 | A1 | 12/2005 | LeBowitz et al. |
| 2006/0029656 | A1 | 2/2006 | O'Donnell et al. |
| 2006/0177433 | A1 | 8/2006 | Treco et al. |
| 2008/0003211 | A1 | 1/2008 | Fogh et al. |
| 2008/0299640 | A1 | 12/2008 | LeBowitz et al. |
| 2009/0017005 | A1 | 1/2009 | Kakkis |
| 2009/0041741 | A1 | 2/2009 | Sly et al. |
| 2009/0130079 | A1 | 5/2009 | Dodge et al. |
| 2009/0191178 | A1 | 7/2009 | Zankel et al. |
| 2009/0246187 | A1 | 10/2009 | Nilsson |
| 2009/0291062 | A1 | 11/2009 | Fraunhofer et al. |
| 2009/0297592 | A1 | 12/2009 | Sakuraba et al. |
| 2010/0068195 | A1 | 3/2010 | Vellard et al. |
| 2010/0260706 | A1 | 10/2010 | Bogin et al. |
| 2011/0105560 | A1 | 5/2011 | Wustman |
| 2011/0318323 | A1 | 12/2011 | Zhu et al. |
| 2011/0318324 | A1 | 12/2011 | Salamat-Miller et al. |
| 2011/0318327 | A1 | 12/2011 | Concino et al. |
| 2012/0003202 | A1 | 1/2012 | Calias et al. |
| 2012/0009171 | A1 | 1/2012 | Salamat-Miller et al. |
| 2012/0014936 | A1 | 1/2012 | Natoli et al. |
| 2012/0148558 | A1 | 6/2012 | Kakkis |
| 2012/0213762 | A1 | 8/2012 | LeBowitz et al. |
| 2013/0168961 | A1 | 7/2013 | Stahlkopf et al. |
| 2013/0295071 | A1 | 11/2013 | Salamat-Miller et al. |
| 2013/0295077 | A1 | 11/2013 | Concino et al. |
| 2014/0271598 | A1 | 9/2014 | Zhu et al. |

FOREIGN PATENT DOCUMENTS

| | | |
|---|---|---|
| WO | WO 03/032727 | 4/2003 |
| WO | WO 03/032913 | 4/2003 |
| WO | WO 03/102583 | 12/2003 |
| WO | WO2004/043373 A2 | 5/2004 |
| WO | WO-2005/002515 A2 | 1/2005 |
| WO | WO-2005/021064 A2 | 3/2005 |
| WO | WO 2005/078077 | 8/2005 |
| WO | WO-2007/141346 A2 | 12/2007 |
| WO | WO-2008/070769 A1 | 6/2008 |
| WO | WO 2009/137721 | 11/2009 |
| WO | WO 2011/163647 | 12/2011 |
| WO | WO 2011/163648 | 12/2011 |
| WO | WO 2011/163649 | 12/2011 |
| WO | WO 2011/163650 | 12/2011 |
| WO | WO 2011/163651 | 12/2011 |
| WO | WO 2011/163652 | 12/2011 |
| WO | WO-2012/023623 A2 | 2/2012 |

OTHER PUBLICATIONS

Kerwin, J. Pharm. Sci. 97: 2924-2935 (2008).*
Kakkis et al., Mol. Genet. and Metab. 83: 163-174 (2004).*
International Search Report for PCT/US11/41926, 5 pages (dated May 13, 2013).
Kakkis, E. et al., Intrathecal enzyme replacement therapy reduces lysosomal storage in the brain and meninges of the canine model of MPS I, Molecular Genetics and Metabolism 83:163-174 (2004).
Written Opinion for PCT/US11/41926, 8 pages (dated May 13, 2013).
Altschul et al., "Basic logic alignment search tool," J. Mol. Biol., 215(3): 403-410, 1990.
Altschul et al., "Gapped BLAST and PSI-BLAST: a new generation of protein database search programs," Nucleic Acids Res. 25: 3389-3402, 1997.
Altschul et al., "Local alignment statistics," 266:460-80, Methods in Enzymology., 1996.
Ammaya et al., "Subcutaneous Reservoir and Pump for Sterile Access to Ventricular Cerebrospinal Fluid," Lancet 2(7315): 983-984, 1963.
Baskin, G. et al., "Genetic galactocerebrosidase deficiency (globoid cell leukodystrophy, Krabbe disease) in rhesus monkeys (*Macaca mulatta*)," Lab Anim. Sci., 48(5): 476-482, 1998.
Baum, H. et al., "The assay of arylsulphatases A and B in human urine," Clin Chim Acta. 4(3): 453-455, 1959.
Begley et al., "Lysosomal storage diseases and the blood-brain barrier," Curr Pharm Des 14(16): 1566-1580, 2008.
Belichenko et al., Penetration, diffusion, and uptake of recombinant human alpha-L-iduronidase after intraventricular injection into the rat brain, Mol. Genet. Metab., 86(1-2): 141-149, 2005.
Beniaminovitz et al., "Prevention of rejection in cardiac transplantation by blockage of the interleukin-2 receptor with a monoclonal antibody," N. Engl. J. Med. 342(9): 613-619, 2000.
Berard et al., "A review of interleukin-2 receptor antagonists in solid organ transplantation," Pharmacotherapy 19(10): 1127-1137, 1999.
Bielicki et al., "Recombinant human sulphamidase: expression, amplification, purification and characterization," Journal of Biochemistry, 329(Pt 1): 145-150, 1998.
Biswas S. et al., "Substrate reduction intervention by L-cycloserine in twitcher mice (globoid cell leukodystrophy) on a B6; CAST/Ei background," Neurosci. Lett., 347(1): 33-36, 2003.
Blasberg, R.G. et al., "Intrathecal chemotherapy: brain tissue profiles after ventriculocisternal perfusion," J Pharmacol Exp Ther. 195(1): 73-83, 1975.
Bobo et al., "Convection-enhanced delivery of macromolecules in the brain," Proc. Natl. Acad. Sci. U.S.A. 91(6), 2076-2080, 1994.
Bowman, R.H., "Inhibition of citrate metabolism by sodium fluoroacetate in the perfused rat heart and the effect on phosphofructokinase activity and glucose utilization," 93(2): 13C-15C, 1964.
Branco et al., "Selective deletion of antigen-specific, activated T cells by a humanized MAB to CD2 (MEDI-507) is mediated by NK cells," Transplantation 68(10): 1588-1596, 1999.

(56) References Cited

OTHER PUBLICATIONS

Butt MT, "Morphologic changes associated with intrathecal catheters for direct delivery to the central nervous system im preclinical studies," Toxicol. Pathol., 39(1): 213-219, 2011.
Cabrera-Salazar, M.A. et al., "Intracerebroventricular delivery of glucocerebrosidase reduces substrates and increases lifespan in a mouse model of neuronopathic Gaucher disease," Exp Neurol. 225(2): 436-444, 2010.
Chirmule et al., "Readministration of adenovirus vector in nonhuman primate lungs by blockage of CD40-CD40 ligand interactions," J. Virol. 74(7): 3345-3352, 2000.
Chiro et al., "Spinal descent of cerebrospinal fluid in man," Neurology 26(1): 1-8, 1976.
Dekaban AS., "Changes in brain weights during the span of human life: relation of brain weights to body heights and body weights," Ann Neurol 4: 345-356, 1978.
Desnick, R.J., "Enzyme replacement and enhancement therapies for lysosomal diseases," J. Inherit. Metab. Dis., 27(3): 385-410, 2004.
Eckhoff et al., "The safety and efficacy of a two-dose daclizumab (zenapax) induction therapy in liver transplant recipients," Transplantation 69(9): 1867-1872, 2000.
Ekberg et al., "Daclizumab prevents acute rejection and improves patient survival post transplantation: 1 year pooled analysis," Transpl. Int. 13(2): 151-159, 2000.
Elaprase (idursulfase), http://www.elaprase.com/pdf/Elaprase_Overview_Sheet110811.pdf, REV 5, 2011.
Fenstermacher et al., "Drug "diffusion" within the brain," Ann NY Acad Sci 531: 29-39, 1988.
Ficko-Blean E, et al., "Structural and mechanistic insight into the basis of mucopolysaccharidosis IIIB," PNAS, 105(18): 6560-6565, 2008.
Fishwild et al., "Differential effects of administration of a human anti-CD4 monoclonal antibody, HM6G, in nonhuman primates," Clin. Immunol. 92(2): 138-152, 1999.
Gaziev et al., "Chronic graft-versus-host disease: is there an alternative to the conventional treatment?," Bone Marrow Transplant, 25(7): 689-696, 2000.
GeneCards, Galactosylceramidase, http://www.genecards.org/cgi-bin/carddisp.pl?gene=GALC&search=Galactocerebrosidase, 2012.
Ghersi-Egea, J.F. et al, "Rapid distribution of intraventricularly administered sucrose into cerebrospinal fluid cisterns via subarachnoid velae in rat," Neuroscience 75(4): 1271-1288, 1996.
Graham et al., "Characteristics of a human cell line transformed by DNA from human adenovirus type 5," J. Gen Virol., 36(1): 59-74, 1977.
Grubb JH et al., "New strategies for enzyme replacement therapy for lysosomal storage diseases," Rejuvenation Research 13(2-3): 229-236, 2010.
Gummert et al., "Newer immunosuppressive drugs: a review," J. Am. Soc. Nephrol, 10(6): 1366-1380, 1999.
Hashimoto R, "N-terminal deletion mutants of insulin-like growth factor-II (IGF-II) show Thr7 and Leu8 important for binding to insulin and IGF-I receptors and Leu8 critical for all IGF-II functions," J Biol Chem., 270(30); 18013-18018, 1995.
Hemsley, Kim M. et al., "Injection of recombinant human sulfamidase into the CSF via the cerebellomedullary cistern in MPS IIIA mice," Mol Genet Metab. 90(3): 313-328, 2007.
Henry ML, "Cyclosporine and tacrolimus (FK506): a comparison of efficacy and safety profiles," Clin. Transplant, 13(3): 209-220, 1999.
Hong et al., "Immunosuppressive agents in organ transplantation: past, present, and future," Semin. Nephrol. 20(2): 108-125, 2000.
Hood RD, Development and Reproductive Toxicology: A practical approach, 276, 2006.
Hoogerbrugge, P.M., et al., "Effect of bone marrow transplantation on enzyme levels and clinical course in the neurologically affected," J. Clin. Invest., 81(6): 1790-1794, 1988.
Hovland DN, et al., "Six-month continuous intraputamenal infusion toxicity study of recombinant methionyl human glial cell line-derived neurotrophic factor (r-metHuGDNF in rhesus monkeys," Toxicol. Pathol., 35(7): 1013-1029, 2007.
Ideguchi et al., "Local adenovirus-mediated CFLA40immunoglobulin expression suppresses the immune responses to adenovirus vectors in the brain," Neuroscience 95(1): 217-226, 2000.
International Search Report for PCT/US11/41922, dated Feb. 14, 2012.
International Search Report for PCT/US11/41924, dated Nov. 7, 2011.
International Search Report for PCT/US11/41925, dated Feb. 14, 2012.
International Search Report for PCT/US11/41927, dated Mar. 9, 2012.
Ito et al., "Induction of CTL responses by simultaneous administration of liposomal peptide vaccine with anti-CD40 and anti-CTLA-4 mAb," J. Immunol. 164(3): 1230-1235, 2000.
Johanson CE, et al., "Multiplicity of cerebrospinal fluid functions: New challenges in health and disease," Cerebrospinal Fluid Res., 14(5): 10, 2008.
Johnson, K., "Globoid leukodystrophy in the cat," J. Am. Vet. Med. Assoc., 157(12): 2057-2064, 1970.
Joshi S. et al., "Targeting the brain: rationalizing the novel methods of drug delivery to the central nervous system," Neurocrit Care 6(3): 200-212, 2007.
Kobayashi T. et al., "The Twitcher mouse: an enzymatically authentic model of human globoid cell leukodystrophy (Krabbe disease)," Brain Res., 202(2): 479-483, 1980.
Krewson, CE et al., "Distribution of nerve growth factor following direct delivery to brain interstitium," Brain Res. 680(1-2): 196-206, 1995.
Kurlberg et al., "Blockage of the B7-CD28 pathway by CTLA4-lg counteracts rejection and prolongs survival in small bowel transplantation," Scand. J. Immunol, 51(3): 224-230, 2000.
Lazorthes et al., Advances in Drug Delivery Systems and Application in Neurosurgery, 18: 143-192, 1991.
Lee, et al., "Single-dose intracerebroventricular administration of galactocerebrosidase improves survival in a mouse model of globoid cell leukodystrophy," FASEB Journal, 21(10): 2520-2527, 2007.
LeVine S. et al., "L-cycloserine slows the clinical and pathological course in mice with globoid cell leukodystrophy (twitcher mice)," J. Neurosci. Res., 60(2): 231-236, 2000.
Li HH, et al., "Mouse model of Sanfilippo syndrome type B produced by targeted disruption of the gene encoding alpha-N-acetylglucosaminidase," PNAS 96(25): 14505-14510, 1999.
Li, et al., "Attenuated plasticity in neurons and astrocytes in the mouse model of Sanfilippo syndrome type B," J Neurosci Res, 69(1): 30-8, 2002.
Lin, D., et al., "Central nervous system-directed AAV2/5-mediated gene therapy synergizes with bone marrow transplantation in the murine model of globoid-cell leukodystrophy," Mol. Ther., 15(1): 44-52, 2007.
Luca, Tonia, "Axons mediate the distribution of arylsulfatase A within the mouse hippocampus upon gene delivery," Mol Ther. 12(4): 669-679, 2005.
Marinova-Mutafchieva et al., "A comparative study into the mechanisms of action of anti-tumor necrosis factor alpha, anti-CD4, and combined anti-tumor necrosis factor alpha/anti-CD4 treatment in early collagen-induced arthritis," Arthritis Rheum 43: 638-644, 2000.
Mather et al., "Culture of testicular cells in hormone-supplemented serum-free medium," Ann N.Y. Acad. Sci., 383: 44-68, 1982.
Mather, "Establishment and characterization of two distinct mouse testicular epithelial cell lines," Biol. Reprod., 23: 243-251, 1980.
Matheus, MG et al., "Brain MRI findings in patients with mucopolysaccharidosis types I and Ii and mild clinical presentation," Neuroradiology 46(8): 666-672, 2004.
Meikle et al., "Diagnosis of lysosomal storage disorders: evaluation of lysosome-associated membrane protein LAMP-1 as a diagnostic marker," Clin Chem., 43(8 Pt 1): 1325-1335, 1997.
Middaugh et al., "Determination of the apparent thermodynamic activities of saturated protein solutions," J. Biol. Chem. 254(2): 367-370, 1979.

(56) References Cited

OTHER PUBLICATIONS

Moder, KG., "New medications for use in patients with rheumatoid arthritis," Ann. Allergy. Asthma Immunol. 84(3): 280-284, 2000.

Nagaraja, TN et al., "In normal rat, intraventricularly administered insulin-like growth factor-1 is rapidly cleared from CSF with limited distribution into brain," Cerebrospinal Fluid Res. 2: 1-15, 2005.

Nail S.L. et al., "Fundamentals of freeze-drying, in Development and manufacture of protein pharmaceuticals," Nail S.L. editor New York: Kluwer Academic/Plenum Publishers, 281-353, 2002.

Neufeld EF, Muenzer J., "The mucopolysaccharidoses," In: Scriver CR, Beaudet AI, Sly WS, et al, eds. The Metabolic and Molecular Bases of Inherited Disease. www.ommbid.com 8th ed. New York, NY: McGraw-Hill; 2001:3421-3452.

Neufeld, E.F., Enzyme Replacement therapy. Lysosomal disorders of the Brain, ed. F.M.a.W. Platt, S.V. 2004: Oxford University Press: 327-338, 2004.

Nevins, TE., "Overview of new immunosuppressive therapies," Curr. Opin. Pediatr. 12(2): 146-150, 2000.

Nguyen et al., "Convective distribution of macromolecules in the primate brain demonstrated using computerized tomography and magnetic resonance imaging," J. Neurosurg. 98(3), 584-590, 2003.

Ohmi, et al., "Activated microglia in cortex of mouse models of mucopolysaccharidoses I and IIIB," Proc Natl Acad Sci, 100(4): 1902-7, 2002.

Ommaya et al., "Implantable devices for chronic access and drug delivery to the central nervous system," Cancer Drug Delivery, 1(2): 169-179, 1984.

Pardridge WM., "Drug transport in brain via the cerebrospinal fluid," Fluids Barriers CNS, 8(1): 7, 2011.

Passini, MA et al., "Distribution of a lysosomal enzyme in the adult brain by axonal transport and by cells of the rostral migratory stream," J Neurosci 22(15): 6437-6446, 2002.

Penn, RD et al., "Intrathecal ciliary neurotrophic factor delivery for treatment of amyotrophic lateral sclerosis (phase I trial)," Neurosurgery 40(1): 94-99, 1997.

Ponce RP, et al., "Immunogenicity of biologically-derived therapeutics: assessment and interpretation of nonclinical safety studies," Regul. Toxicol. Pharmacol., 54(2): 164-182, 2009.

Ponticelli et al., "Promising new agents in the prevention of transplant rejection," Drugs R.D. 1(1), 55-60, 1999.

Potter et al., "Review—the use of immunosuppressive agents to prevent neutralizing antibodies against a transgene product," Ann. N.Y. Acad. Sci. 875: 159-174, 1999.

Pritchard, D. et al., "Globoid cell leucodystrophy in polled Dorset sheet," Vet. Pathol., 17(4): 399-405, 1980.

Przepiorka et al., "A phase II study of BTI-322, a monoclonal anti-CD2 antibody, for treatment of steroid-resistant acute graft-versus-host disease," Blood 92(11): 4066-4071, 1998.

Qi et al., "Effect of tacrolimus (FK506) and sirolimus (rapamycin) mono- and combination therapy in prolongation of renal allograft survival in the monkey," Transplantation 69(7), 1275-1283, 2000.

Rieselbach RE et al., "Subarachnoid distribution of drugs after lumbar injection," N Engl J Med. 267(25): 1273-1278, 1962.

Savas, et al., "Intracerebral injection of sulfamidase delays neuropathology in murine MPS-IIIA," Mol Genet Metab., 82(4): 273-285, 2004.

Shahrokh et al., "Intrathecal delivery of protein therapeutics to treat genetic diseases involving the CNS, in: Injectable Drug Delivery 2010: Formulations Focus," ONdrugDelivery, pp. 16-20, 2010.

Simard JM et al., "Brain oedema in focal ischaemia: molecular pathophysiology and theoretical implications," Lancet Neurol. 6(3): 258-268, 2007.

Slavik et al., "CD28/CTLA-4 and CD80/CD86 families: signaling and function," Immunol Res. 19(1): 1-24, 1999.

Stamatovic SM, et al., "Brain endothelial cell-cell junctions: how to "open" the blood brain barrier," Curr. Neuropharmacol., 6(3): 179-192, 2008.

Stroobants S. et al., "Intracerebroventricular enzyme infusion corrects central nervous system pathology and dysfunction in a mouse model of metachromatic leukodystrophy," Hum Mol Genet. 20(14): 2760-2769, 2011.

Sturk, et al., "Combined Intracerebroventricular Intraperitoneal Enzyme Replacement Therapy Improves Survival and Reduces Brain Psychosine in a Mouse Model of Krabbe Disease," European Task Force on Brain and Neurogenerative Lysosomal Storage Diseases, http://www.brains4brain.eu/assets/files/abstract-francoforte-2009.pdf p. 42, 2009.

Tang, X. et al., "Design of freeze-drying processes for pharmaceuticals: Practical advice," Pharm. Res., 21(2): 191-200, 2004.

Toyoshima, E. et al., "Nerve conduction studies in the Twitcher mouse (murine globoid cell leukodystrophy)," J. Neurol. Sci., 74(2-3): 307-318, 1986.

Urlaub and Chasin, "Isolation of Chinese hamster cell mutants deficient in dihydrofolate reductase activity," Proc. Natl. Acad. Sci. USA, 77(7): 4216-4220, 1980.

Vedolin, L. et al., "Correlation of MR imaging and MR spectroscopy findings with cognitive impairment in mucopolysaccharidosis II," AJNR Am J Neuroradial 28(6): 1029-1033, 2007.

Vite, Charles H. et al., "Biodistribution and pharmacodynamics of recombinant human alpha-L-iduronidase (rhIDU) in mucopolysaccharidosis type I-affected cats following multiple intrathecal administrations," Mol Genet Metab 103(3): 268-274, 2011.

Vogler, C. et al., "Overcoming the blood-brain barrier with high-dose enzyme replacement therapy in murine mucopolysaccharidosis VII," Proc Natl Acad Sci USA 102(41): 14777-14782, 2005.

Waheed, A et al., "Purification of mammalian arylsulfatase A enzymes by subunit affinity chromatography," Int J Pept Protein Res., 26(4): 362-372, 1985.

Walkley, "Cell Pathology of lysosomal storage disorders," Brain Pathol., 8, 175-93, 1998.

Wang et al., "Lyophilization and development of solid protein pharmaceuticals," Int. J. Pharm., 203(1-2): 1-60, 2000.

Wang et al., "Treatment reduces or stabilizes brain imaging abnormalities in patients with MPS I and II," Molecular Genetics and Metabolism, 98(4): 406-11, 2009.

Watson et al., "Intrathecal administration of AAV vectors for the treatment of lysosomal storage in the brains of MPS I mice," Gene Ther., 13(11): 917-925, 2006.

Wenger, D.A. et al., Galactosylceramide Lipidosis: Globoid Cell Leukodystrophy (Krabbe Disease), in the Metabolic and Molecular Bases of Inherited Disease, C.R. Scriver, Beaudet, A., Sly, W.S. and Valle, D. Editor 2001 McGraw-Hill, 3669-3687, 2001.

Wenger, D.A., "Murine, canine and non-human primate models of Krabbe disease," Mol. Med. Today, 6(11): 449-451, 2000.

Williams N. A. et al., "The lyophilization of pharmaceuticals; A literature review." J. Parenter Sci. Technol., 38(2): 48-59, 1984.

Wiseman et al., "Daclizumab: a review of its use in the prevention of acute rejection in renal transplant recipients," Drugs 58(6): 1029-1042, 1999.

Written Opinion for PCT/US11/41922, dated Feb. 14, 2012.
Written Opinion for PCT/US11/41924, dated Nov. 7, 2011.
Written Opinion for PCT/US11/41925, dated Feb. 14, 2012.
Written Opinion for PCT/US11/41927, dated Mar. 9, 2012.

Yan Q et al., "Distribution of intracerebral ventricularly administered neurotrophins in rat brain and its correlation with trk receptor expression," Exp Neurol. 127(1): 23-36, 1994.

Yeager A. et al., "Prolonged survival and remyelination after hematopoietic cell transplantation in the twitcher mouse," Science, 225(4666): 1052-1054, 1984.

Clarke, L. A., Idursulfase for the treatment of mucopolysaccharidosis II, Expert Opin. Pharmacother., 9(2):311-317 (2008).

Phosphate Buffer Calculation, http://www.egr.msu.edu/biofuelcell/tools/phosphate/phosphate.html, Dec. 31, 2000, accessed Aug. 28, 2012.

Schlessingerman, A., Mass of an Adult, obtained from hypertextbook.com/facts/2003/AlexSchlessingerman.shtml, 2003, 2 pages.

Sjoberg, M. et al., Long-term Intrathecal Morphine and Bupivacaine in Patients with Refractory Cancer Pain, Anesthesiology, 80:284-297 (1994).

(56) References Cited

OTHER PUBLICATIONS

Champion K. J. et al., Identification and characterization of a novel homozygous deletion in the x-N-acetylglucosaminidase gene in a patient with Sanfilippo type B syndrome (mucopolysaccharidosis IIIB), Molecular Genetics and Metabolism, 100: 51-56 (2010).
Cressent, A. et al., Improved Behavior and Neuropathology in the Mouse Model of Sanfilippo Type IIIB Disease after Adeno-Associated Virus-Mediated Gene Transfer in the Striatum, The Journal of Neuroscience, 24(45): 10229-10239 (2004).
Tippin, B. et al., Insulin-like Growth Factor-2 Peptide Fusion Enables Uptake and Lysosomal Delivery of N-Acetylglucosamindidase to Mucopolysaccharidosis IIIB Fibrboblasts, MPS Scientific Program: Plenary Papers, entire document: p. 100 (Jun. 26, 2010).
International Search Report for PCT/US2011/041928,4 pages (dated Sep. 26, 2012).
Written Opinion for PCT/US2011/041928,13 pages (dated Sep. 26, 2012).
Anonymous, TKT to Present Research on Intrathecal Delivery of I2S for Hunter Syndrome at ASHG, PRNewswire, 1 (2004).
Anonymous, TKT's Research Findings on Intrathecal Delivery of I2S Presented at ASHG, Evaluate Ltd, 1 (2004).
Descartes, M. et al., Enzyme Replacement Therapy for MPS II: Developing a Pre-Medication Protocol, University of Alabama and Children's Hospital of Alabama, 1 (2007).
Dickson, P.I., Novel Treatments and Future Perspectives: Outcomes of Intrathecal Drug Delivery, International Journal of Clinical Pharmacology and Therapeutics, 47:1 S124-127 (2009).
Extended European Search Report for 11799039.0, 12 pages (dated Jun. 10, 2014).
Fu, H. et al., Restoration of Central Nervous System a-N-Acetylglucosaminidase Activity and Therapeutic Benefits in Mucopolysaccharidosis IIIB Mice by a Single Intracisternal Recombinant Adeno-Associated Viral Type 2 Vector Delivery, The Journal of Gene Medicine, 12:624-633 (2010).
Fu, H. et al., Significantly Increased Lifespan and Improved Behavioral Performances by rAAV Gene Delivery in Adult Mucopolysaccharidosis IIIB Mice, Gene Therapy 14:1065-1077 (2007).
Garcia, A.R. et al., Intrathecal Delivery of Iduronate 2-Sulfatase to the CNS of Cynomolgus Monkeys, Shire Human Genetic Therapies, 1 (2007).
GenBank accession No. NM000263, *Homo sapiens* N-Acetylglucosaminidase, Alpha (NAGLU) mRNA, 1-4 (accessed May 3, 2014).
Lamsa, J.C et al., Delivery of I2S to the Canine CNS: Comparison of Intracisternal, Intralumbar and Intraventricular Dose Routes as Potential Treatents for Severe MPS II, Shire HGT, 1 (2006).
Lamsa, J.C. et al., Intrathecal Delivery of Iduronate 2-Sulfatase for MPS II to the Canine CNS, ASHG Annual Meeting, 1 (2004).
Lu, Y. et al., Direct Brain Delivery of Iduronate 2-Sulfastase Reduces Glycosaminoglycan Accumulation and Improves Histopathology in the CNS and Peripheral Tissue of Hunter Mice, Shire HGT, 1 (2007).
Sinow, C.S., Construction of an IGF-NAGLU Fusion Protein for Treatment of Sanfilippo B Syndrome, California State Sciene Fair, 1 (2008).
Vertemati, T. et al., Multidisciplinary Evaluation in 12 Mucopolysaccharidose Type II or Hunter Syndrome Patients Prior Enzyme Replacement Therapy, CREIM, UNIFESP, 1 (2007).
Wang, W. and Roberts, C., Aggregation of Therapeutic Proteins, published by John Wiley & Sons, Inc., Hoboken, New Jersey (2010).
Won, C., Stabilizers against heat-induced aggregation of RPR 114849, an acidic fibroblast growth factor (aFGF), International Journal of Pharmaceutics, 167:25-36 (1998).
Elaprase idursulface, European Medicines Agency—Science, Medicines, Health, XP-002716697, pp. 1-3 (2007).
Extended European Search Report for EP11799035.8, 7 pages, dated Dec. 16, 2013.
Felice, B.R. et al., Safety Evaluation of Chronic Intrathecal Administration of Idursulfase-IT in Cynomolgus Monkeys, Toxicology Pathology, 39:879-892 (2011).
Okuyama, T. et al., Japan Elaprase® Treatment (JET) study: Idursulfase enzyme replacement therapy in adult patients with attenuated Hunter syndrome (Mucopolysaccharidosis II, MPS II), Molecular Genetics and Metabolism, 99:18-25 (2010).
Scientific Discussion—Elaprase, XP00271916, pp. 1-43 (2007).
Shire Human Genetic Therapies, Intrathecal Delivery of Protein Therapeutics to Treat Genetic Diseases Involving the CNS, www.ondrugdelivery.com, pp. 16-20, (Publically available on Jun. 30, 2010).
Burrow, T. Andrew and Leslie, Nancy D., Review of the use of idursulfase in the treatment of mucopolysaccharidosis II, Biologics: Targets and Therapy, 2(2):311-320 (2008).
Dickson, P. et al., Intrathecal enzyme replacement therapy: Successful treatment of brain disease via the cerebrospinal fluid, Molecular Genetics & Metabolism, 91(1):61-68 (2007).
Esposito, S. et al, Heparan N-sulfatase gene: two novel mutations and transient expression of 15 defects, Biochimica et Biophysica Acta 1501, 1-11: 1 (2000).
European Search Report for EP, 11799034.1, 8 pages (dated Mar. 12, 2014).
Garbuzova-Davis, S. et al., Transplantation of Human Umbilical Cord Blood Cells Benefits an Animal Model of Sanfilippo Syndrome Type B, Stem Cells and Development, 14:384-394 (2005).
International Preliminary Report on Patentability for PCT/US11/41928, 36 pages (dated Mar. 29, 2013).
Kang, H. et al., Significantly increased lifespan and improved behavioral performances by rAAV gene delivery in adult mucupolysaccharidosis IIIB mice, Gene Therapy, 14:1066-1077 (2007).
Weber, B. et al., Novel Mutations in Sanfilippo A syndrome: Implications for Enzyme function, Hum. Mol. Genet., 6(9): 1573-1579 (1997).
Wraith, J.E. et al., Mucopolysaccharidosis type II (Hunter syndrome): a clinical review and recommendations for treatment in the era of enzyme replacement therapy, Eur. J. Pediatr., 167: 247-277 (2008).
Greene, et al., Metachromatic Leukodystriphym, Arch. Neurol., vol. 20, Feb. 1969, pp. 147-153.
Hemsley, et al., Effect of high dose, repeated intra-cerebrospinal fluid injection of sulphamidase on neuropathology in mucopolysaccharidosis type IIIA mise, Genes, Brain and Behavior, 7:740-753, (2008), pp. 740-753.

\* cited by examiner

WT        Vehicle        IT treated

WT= Wild type; IT treated mice received 4 weekly doses of 520 mg/kg brain weight of rhASA1 (0.21 mg), 4X magnification.

\*\* P<0.001; \* P<0.05
T-Spinal cord = total spinal cord
T-GM = total gray matter
L-GM = lumbar gray matter
C-GM = cervical gray matter
T-WM = total white matter
L-WM = lumbar white matter
C-WM = cervical white matter WT= Wild type; IT treated mice received 4 weekly doses of 520 mg/kg brain weight of rhASA1 (0.21 mg), 20X magnification.

62-133 #458

Slice 4

Anatomical label
1. Subcortical WM
2. Periventricular WM and deep white matter
3. 3.Subcortical WM 1 cm 1 cm Anatomical label 4. Corpus callosum and pericallosal subcortical WM
5. Internal capsule, GPi
6. Internal capsule, caudate nucleus
7. Deep white matter
8. Subcortical WM and cortex
9. putamen
10. Temporal subcortical WM and cortex Anatomical label
15. Corpus callosum and pericallosal subcortical WM
16. Deep Subcortical WM
17. Deep grey
18. Deep grey
19. Periventricular WM
20. Subcortical WM
21. hippocampus 1 cm Anatomical label
24. Subcortical WM, occipital lobe
25. Cerebellar White Matte, including dentate nucleus (WM)

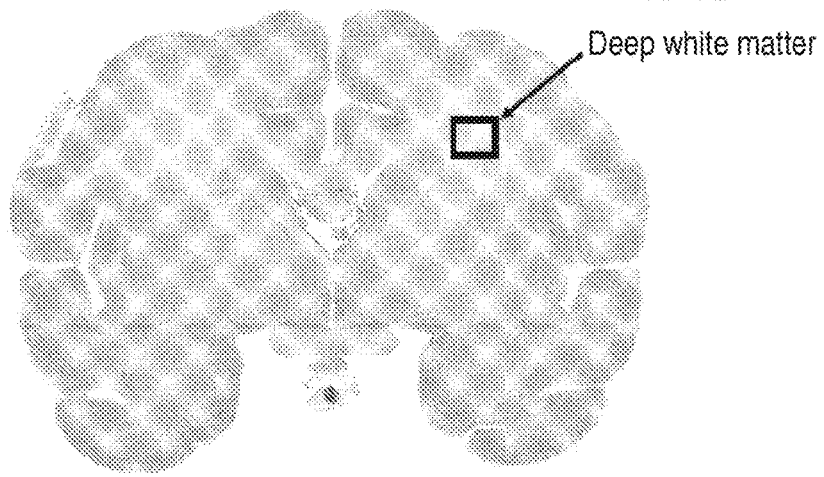
*Fig. 47A*
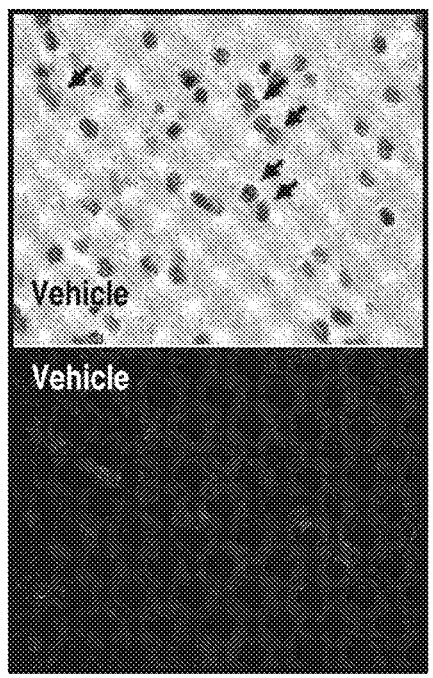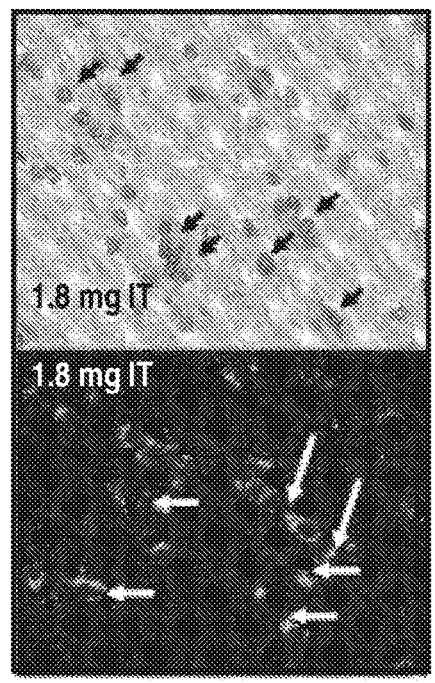
*Fig. 47B*

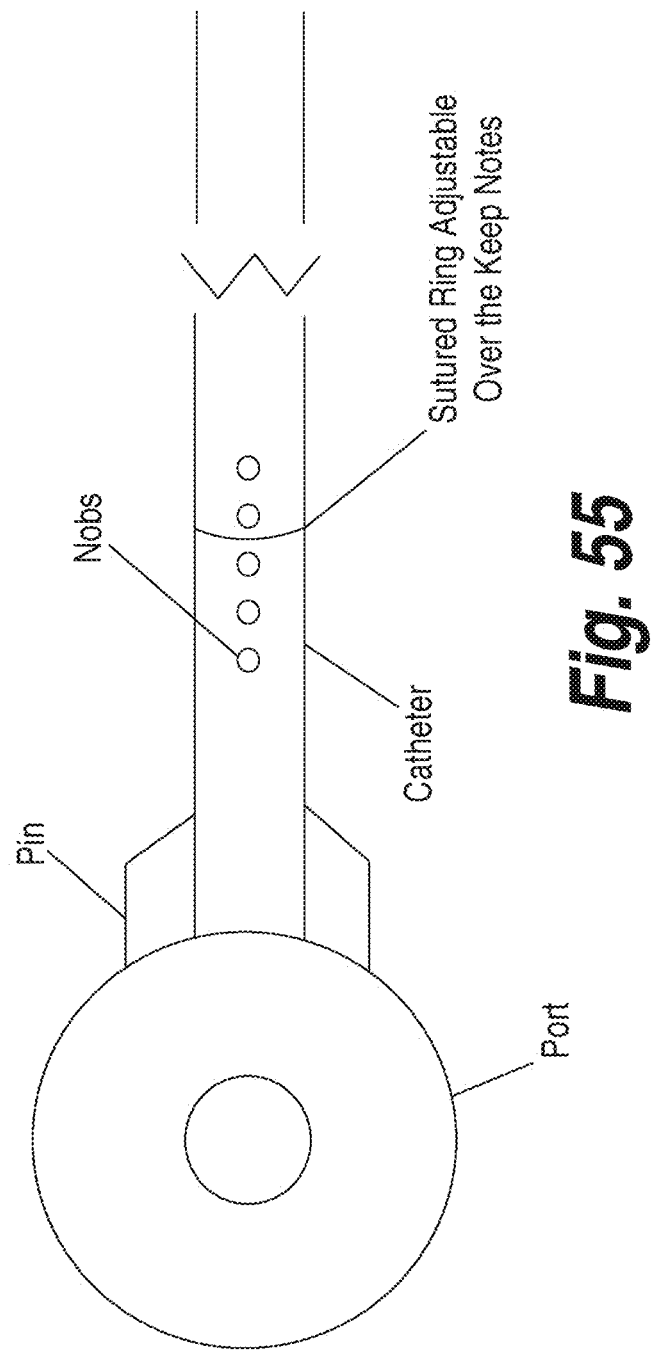

METHODS AND COMPOSITIONS FOR CNS DELIVERY OF ARYLSULFATASE A

CROSS REFERENCE TO RELATED APPLICATIONS

This application claims priority to U.S. Provisional Patent Application Ser. Nos. 61/358,857 filed Jun. 25, 2010; 61/360,786, filed Jul. 1, 2010; 61/387,862, filed Sep. 29, 2010; 61/435,710, filed Jan. 24, 2011; 61/442,115, filed Feb. 11, 2011; 61/476,210, filed Apr. 15, 2011 and 61/495,268 filed on Jun. 9, 2011; the entirety of each of which is hereby incorporated by reference.

This application relates to US applications entitled "CNS Delivery of Therapeutic Agents," filed on even date; "Methods and Compositions for CNS Delivery of Heparan N-Sulfatase," filed on even date; "Methods and Compositions for CNS Delivery of Iduronate-2-Sulfatase," filed on even date; "Methods and Compositions for CNS Delivery of β-Galactocerebrosidase," filed on even date; "Treatment of Sanfilippo Syndrome Type B," filed on even date; the entirety of each of which is hereby incorporated by reference.

SEQUENCE LISTING

In accordance with 37 CFR 1.52(e)(5), a Sequence Listing in the form of a text file (entitled "SequenceListing.txt," created on Aug. 3, 2011, and 9 kilobytes in size) is incorporated herein by reference in its entirety.

BACKGROUND

Enzyme replacement therapy (ERT) involves the systemic administration of natural or recombinantly-derived proteins and/or enzymes to a subject. Approved therapies are typically administered to subjects intravenously and are generally effective in treating the somatic symptoms of the underlying enzyme deficiency. As a result of the limited distribution of the intravenously administered protein and/or enzyme into the cells and tissues of the central nervous system (CNS), the treatment of diseases having a CNS etiology has been especially challenging because the intravenously administered proteins and/or enzymes do not adequately cross the blood-brain barrier (BBB).

The blood-brain barrier (BBB) is a structural system comprised of endothelial cells that functions to protect the central nervous system (CNS) from deleterious substances in the blood stream, such as bacteria, macromolecules (e.g., proteins) and other hydrophilic molecules, by limiting the diffusion of such substances across the BBB and into the underlying cerebrospinal fluid (CSF) and CNS.

There are several ways of circumventing the BBB to enhance brain delivery of a therapeutic agent including direct intra-cranial injection, transient permeabilization of the BBB, and modification of the active agent to alter tissue distribution. Direct injection of a therapeutic agent into brain tissue bypasses the vasculature completely, but suffers primarily from the risk of complications (infection, tissue damage, immune responsive) incurred by intra-cranial injections and poor diffusion of the active agent from the site of administration. To date, direct administration of proteins into the brain substance has not achieved significant therapeutic effect due to diffusion barriers and the limited volume of therapeutic that can be administered. Convection-assisted diffusion has been studied via catheters placed in the brain parenchyma using slow, long-term infusions (Bobo, et al., Proc. Natl. Acad. Sci. U.S.A 91, 2076-2080 (1994); Nguyen, et al. J. Neurosurg. 98, 584-590 (2003)), but no approved therapies currently use this approach for long-term therapy. In addition, the placement of intracerebral catheters is very invasive and less desirable as a clinical alternative.

Intrathecal (IT) injection, or the administration of proteins to the cerebrospinal fluid (CSF), has also been attempted but has not yet yielded therapeutic success. A major challenge in this treatment has been the tendency of the active agent to bind the ependymal lining of the ventricle very tightly which prevented subsequent diffusion. Currently, there are no approved products for the treatment of brain genetic disease by administration directly to the CSF.

In fact, many believed that the barrier to diffusion at the brain's surface, as well as the lack of effective and convenient delivery methods, were too great an obstacle to achieve adequate therapeutic effect in the brain for any disease.

Many lysosomal storage disorders affect the nervous system and thus demonstrate unique challenges in treating these diseases with traditional therapies. There is often a large build-up of glycosaminoglycans (GAGs) in neurons and meninges of affected individuals, leading to various forms of CNS symptoms. To date, no CNS symptoms resulting from a lysosomal disorder has successfully been treated by any means available.

Thus, there remains a great need to effectively deliver therapeutic agents to the brain. More particularly, there is a great need for more effective delivery of active agents to the central nervous system for the treatment of lysosomal storage disorders.

SUMMARY OF THE INVENTION

The present invention provides an effective and less invasive approach for direct delivery of therapeutic agents to the central nervous system (CNS). The present invention is, in part, based on unexpected discovery that a replacement enzyme (e.g., arylsulfatase A (ASA)) for a lysosomal storage disease (e.g., MLD) can be directly introduced into the cerebrospinal fluid (CSF) of a subject in need of treatment at a high concentration (e.g., greater than about 3 mg/ml, 4 mg/ml, 5 mg/ml, 10 mg/ml or more) such that the enzyme effectively and extensively diffuses across various surfaces and penetrates various regions across the brain, including deep brain regions. More surprisingly, the present inventors have demonstrated that such high protein concentration delivery can be done using simple saline or buffer-based formulations and without inducing substantial adverse effects, such as severe immune response, in the subject. Therefore, the present invention provides a highly efficient, clinically desirable and patient-friendly approach for direct CNS delivery for the treatment various diseases and disorders that have CNS components, in particular, lysosomal storage diseases. The present invention represents a significant advancement in the field of CNS targeting and enzyme replacement therapy.

As described in detail below, the present inventors have successfully developed stable formulations for effective intrathecal (IT) administration of an arylsulfatase A (ASA) protein. It is contemplated, however, that various stable formulations described herein are generally suitable for CNS delivery of therapeutic agents, including various other lysosomal enzymes. Indeed, stable formulations according to the present invention can be used for CNS delivery via various techniques and routes including, but not limited to, intraparenchymal, intracerebral, intravetricular cerebral (ICV), intrathecal (e.g., IT-Lumbar, IT-cisterna magna) administrations and any other techniques and routes for injection directly or indirectly to the CNS and/or CSF.

It is also contemplated that various stable formulations described herein are generally suitable for CNS delivery of other therapeutic agents, such as therapeutic proteins including various replacement enzymes for lysosomal storage diseases. In some embodiments, a replacement enzyme can be a synthetic, recombinant, gene-activated or natural enzyme.

In various embodiments, the present invention includes a stable formulation for direct CNS intrathecal administration comprising an arylsulfatase A (ASA) protein, salt, and a polysorbate surfactant. In some embodiments, the ASA protein is present at a concentration ranging from approximately 1-300 mg/ml (e.g., 1-250 mg/ml, 1-200 mg/ml, 1-150 mg/ml, 1-100 mg/ml, 1-50 mg/ml). In some embodiments, the ASA protein is present at or up to a concentration selected from 2 mg/ml, 3 mg/ml, 4 mg/ml, 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml, 100 mg/ml, 150 mg/ml, 200 mg/ml, 250 mg/ml, or 300 mg/ml.

In various embodiments, the present invention includes a stable formulation of any of the embodiments described herein, wherein the ASA protein comprises an amino acid sequence of SEQ ID NO:1. In some embodiments, the ASA protein comprises an amino acid sequence at least 60%, 65%, 70%, 75%, 80%, 85%, 90%, 95%, or 98% identical to SEQ ID NO:1. In some embodiments, the stable formulation of any of the embodiments described herein includes a salt. In some embodiments, the salt is NaCl. In some embodiments, the NaCl is present as a concentration ranging from approximately 0-300 mM (e.g., 0-250 mM, 0-200 mM, 0-150 mM, 0-100 mM, 0-75 mM, 0-50 mM, or 0-30 mM). In some embodiments, the NaCl is present at a concentration ranging from approximately 137-154 mM. In some embodiments, the NaCl is present at a concentration of approximately 154 mM.

In various embodiments, the present invention includes a stable formulation of any of the embodiments described herein, wherein the polysorbate surfactant is selected from the group consisting of polysorbate 20, polysorbate 40, polysorbate 60, polysorbate 80 and combination thereof. In some embodiments, the polysorbate surfactant is polysorbate 20. In some embodiments, the polysorbate 20 is present at a concentration ranging approximately 0-0.02%. In some embodiments, the polysorbate 20 is present at a concentration of approximately 0.005%.

In various embodiments, the present invention includes a stable formulation of any of the embodiments described herein, wherein the formulation further comprises a buffering agent. In some embodiments, the buffering agent is selected from the group consisting of phosphate, acetate, histidine, sccinate, Tris, and combinations thereof. In some embodiments, the buffering agent is phosphate. In some embodiments, the phosphate is present at a concentration no greater than 50 mM (e.g., no greater than 45 mM, 40 mM, 35 mM, 30 mM, 25 mM, 20 mM, 15 mM, 10 mM, or 5 mM). In some embodiments, the phosphate is present at a concentration no greater than 20 mM. In various aspects the invention includes a stable formulation of any of the embodiments described herein, wherein the formulation has a pH of approximately 3-8 (e.g., approximately 4-7.5, 5-8, 5-7.5, 5-6.5, 5-7.0, 5.5-8.0, 5.5-7.7, 5.5-6.5, 6-7.5, or 6-7.0). In some embodiments, the formulation has a pH of approximately 5.5-6.5 (e.g., 5.5, 6.0, 6.1, 6.2, 6.3, 6.4, or 6.5). In some embodiments, the formulation has a pH of approximately 6.0.

In various embodiments, the present invention includes stable formulations of any of the embodiments described herein, wherein the formulation is a liquid formulation. In various embodiments, the present invention includes stable formulation of any of the embodiments described herein, wherein the formulation is formulated as lyophilized dry powder.

In some embodiments, the present invention includes a stable formulation for intrathecal administration comprising an arylsulfatase A (ASA) protein at a concentration ranging from approximately 1-300 mg/ml, NaCl at a concentration of approximately 154 mM, polysorbate 20 at a concentration of approximately 0.005%, and a pH of approximately 6.0. In some embodiments, the ASA protein is at a concentration of approximately 10 mg/ml. In some embodiments, the ASA protein is at a concentration of approximately 30 mg/ml, 40 mg/ml, 50 mg/ml, 100 mg/ml, 150 mg/ml, 200 mg/ml, 250 mg/ml, or 300 mg/ml.

In various aspects, the present invention includes a container comprising a single dosage form of a stable formulation in various embodiments described herein. In some embodiments, the container is selected from an ampule, a vial, a bottle, a cartridge, a reservoir, a lyo-ject, or a pre-filled syringe. In some embodiments, the container is a pre-filled syringe. In some embodiments, the pre-filled syringe is selected from borosilicate glass syringes with baked silicone coating, borosilicate glass syringes with sprayed silicone, or plastic resin syringes without silicone. In some embodiments, the stable formulation is present in a volume of less than about 50 mL (e.g., less than about 45 ml, 40 ml, 35 ml, 30 ml, 25 ml, 20 ml, 15 ml, 10 ml, 5 ml, 4 ml, 3 ml, 2.5 ml, 2.0 ml, 1.5 ml, 1.0 ml, or 0.5 ml). In some embodiments, the stable formulation is present in a volume of less than about 3.0 mL.

In various aspects, the present invention includes methods of treating Metachromatic Leukodystrophy Disease including the step of administering intrathecally to a subject in need of treatment a formulation according to any of the embodiments described herein.

In some embodiments, the present invention includes a method of treating Metachromatic Leukodystrophy Disease including a step of administering intrathecally to a subject in need of treatment a formulation comprising an arylsulfatase A (ASA) protein at a concentration ranging from approximately 1-300 mg/ml, NaCl at a concentration of approximately 154 mM, polysorbate 20 at a concentration of approximately 0.005%, and a pH of approximately 6.

In some embodiments, the intrathecal administration results in no substantial adverse effects (e.g., severe immune response) in the subject. In some embodiments, the intrathecal administration results in no substantial adaptive T cell-mediated immune response in the subject.

In some embodiments, the intrathecal administration of the formulation results in delivery of the arylsulfatase A protein to various target tissues in the brain, the spinal cord, and/or peripheral organs. In some embodiments, the intrathecal administration of the formulation results in delivery of the arylsulfatase A protein to target brain tissues. In some embodiments, the brain target tissues comprise white matter and/or neurons in the gray matter. In some embodiments, the arylsulfatase A protein is delivered to neurons, glial cells, perivascular cells and/or meningeal cells. In some embodiments, the arylsulfatase A protein is further delivered to the neurons in the spinal cord.

In some embodiments, the intrathecal administration of the formulation further results in systemic delivery of the ASA protein in peripheral target tissues. In some embodiments, the peripheral target tissues are selected from liver, kidney, spleen and/or heart.

In some embodiments, the intrathecal administration of the formulation results in lysosomal localization in brain target tissues, spinal cord neurons and/or peripheral target tissues. In some embodiments, the intrathecal administration of the formulation results in reduction of sulfatide storage in the brain target tissues, spinal cord neurons and/or peripheral target tissues. In some embodiments, the sulfatide storage is reduced by at least 10%, 20%, 30%, 40%, 50%, 60%, 70%, 80%, 90%, 1-fold, 1.5-fold, or 2-fold as compared to a control (e.g., the pre-treatment GAG storage in the subject). In some embodiments, the intrathecal administration of the formulation results in reduced vacuolization in neurons (e.g., by at least 20%, 40%, 50%, 60%, 80%, 90%, 1-fold, 1.5-fold, or 2-fold as compared to a control). In some embodiments, the neurons comprises Purkinje cells.

In some embodiments, the intrathecal administration of the formulation results in increased ASA enzymatic activity in the brain target tissues, spinal cord neurons and/or peripheral target tissues. In some embodiments, the ASA enzymatic activity is increased by at least 1-fold, 2-fold, 3-fold, 4-fold, 5-fold, 6-fold, 7-fold, 8-fold, 9-fold or 10-fold as compared to a control (e.g., the pre-treatment endogenous enzymatic activity in the subject). In some embodiments, the increased ASA enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg.

In some embodiments, the ASA enzymatic activity is increased in the lumbar region. In some embodiments, the increased ASA enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In some embodiments, the intrathecal administration of the formulation results in reduced intensity, severity, or frequency, or delayed onset of at least one symptom or feature of MLD. In some embodiments, the at least one symptom or feature of the MLD is cognitive impairment; white matter lesions; dilated perivascular spaces in the brain parenchyma, ganglia, corpus callosum, and/or brainstem; atrophy; and/or ventriculomegaly.

In some embodiments, the intrathecal administration takes place once every two weeks. In some embodiments, the intrathecal administration takes place once every month. In some embodiments, the intrathecal administration takes place once every two months. In some embodiments, the intrathecal administration is used in conjunction with intravenous administration. In some embodiments, the intravenous administration is no more frequent than once every week. In some embodiments, the intravenous administration is no more frequent than once every two weeks. In some embodiments, the intravenous administration is no more frequent than once every month. In some embodiments, the intravenous administration is no more frequent than once every two months. In certain embodiments, the intravenous administration is more frequent than monthly administration, such as twice weekly, weekly, every other week, or twice monthly.

In some embodiments, intraveneous and intrathecal administrations are performed on the same day. In some embodiments, the intraveneous and intrathecal administrations are not performed within a certain amount of time of each other, such as not within at least 2 days, within at least 3 days, within at least 4 days, within at least 5 days, within at least 6 days, within at least 7 days, or within at least one week. In some embodiments, intraveneous and intrathecal administrations are performed on an alternating schedule, such as alternating administrations weekly, every other week, twice monthly, or monthly. In some embodiments, an intrathecal administration replaces an intravenous administration in an administration schedule, such as in a schedule of intraveneous administration weekly, every other week, twice monthly, or monthly, every third or fourth or fifth administration in that schedule can be replaced with an intrathecal administration in place of an intravenous administration.

In some embodiments, intraveneous and intrathecal administrations are performed sequentially, such as performing intraveneous administrations first (e.g., weekly, every other week, twice monthly, or monthly dosing for two weeks, a month, two months, three months, four months, five months, six months, a year or more) followed by IT administrations (e.g., weekly, every other week, twice monthly, or monthly dosing for more than two weeks, a month, two months, three months, four months, five months, six months, a year or more). In some embodiments, intrathecal administrations are performed first (e.g., weekly, every other week, twice monthly, monthly, once every two months, once every three months dosing for two weeks, a month, two months, three months, four months, five months, six months, a year or more) followed by intraveneous administrations (e.g., weekly, every other week, twice monthly, or monthly dosing for more than two weeks, a month, two months, three months, four months, five months, six months, a year or more).

In some embodiments, the intrathecal administration is used in absence of intravenous administration.

In some embodiments, the intrathecal administration is used in absence of concurrent immunosuppressive therapy.

BRIEF DESCRIPTION OF THE DRAWINGS

FIG. 47A illustrates the area of deep white matter tissue extracted from a cynomolgus monkey IT-administered 1.8 mg of rhASA. FIG. 47B illustrates immunostaining of the deep white matter tissue and revealed distribution of rhASA in relevant cells. In FIG. 47C, ASA immunostaining is illustrated in the top left box.

FIG. 55 illustrates and exemplary diagram of an intrathecal drug delivery device (IDDD) with a securing mechanism.

DEFINITIONS

Figure 1:
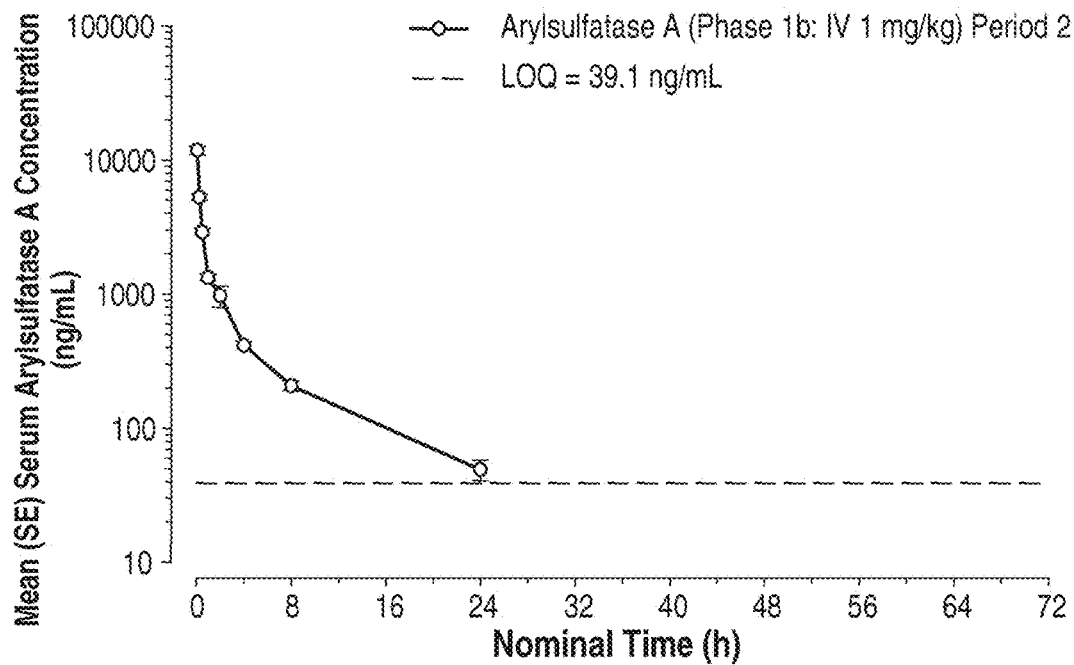
FIG. 1 illustrates exemplary arylsulfatase A (rhASA) concentration data in serum after IV administration.
Figure 2:
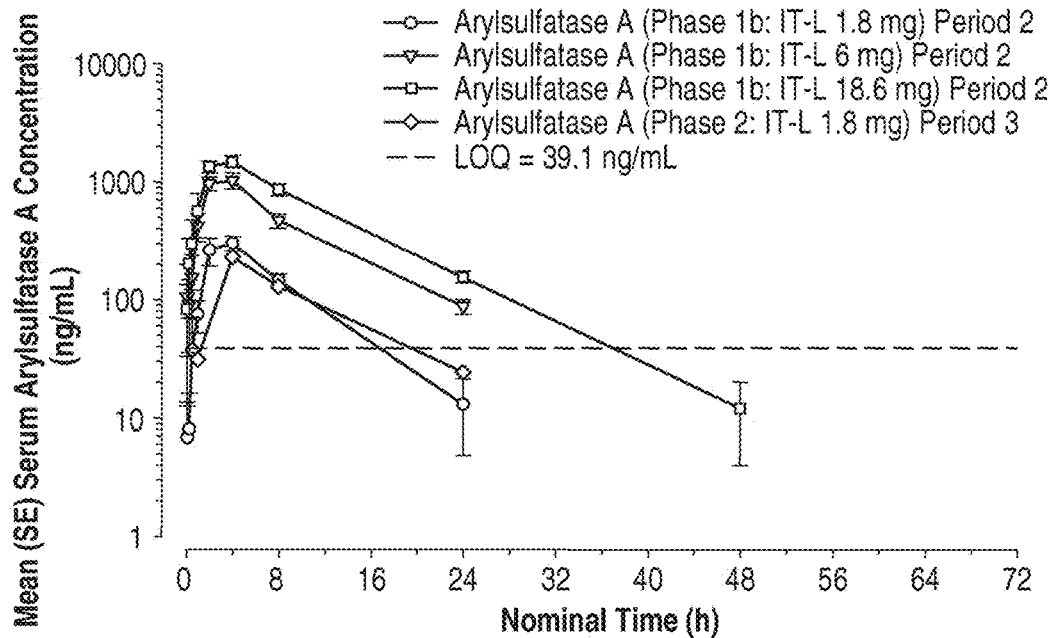
FIG. 2 illustrates exemplary rhASA concentration data in serum after IT-lumbar administration.
Figure 3:
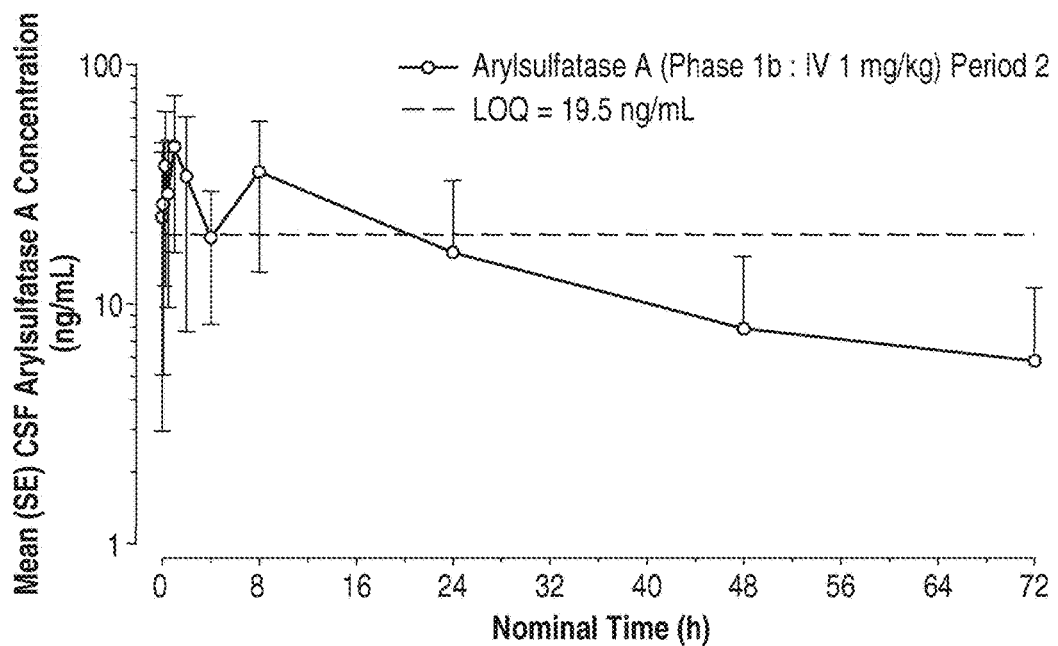
FIG. 3 illustrates exemplary rhASA concentration in CSF after IV administration.
Figure 4:
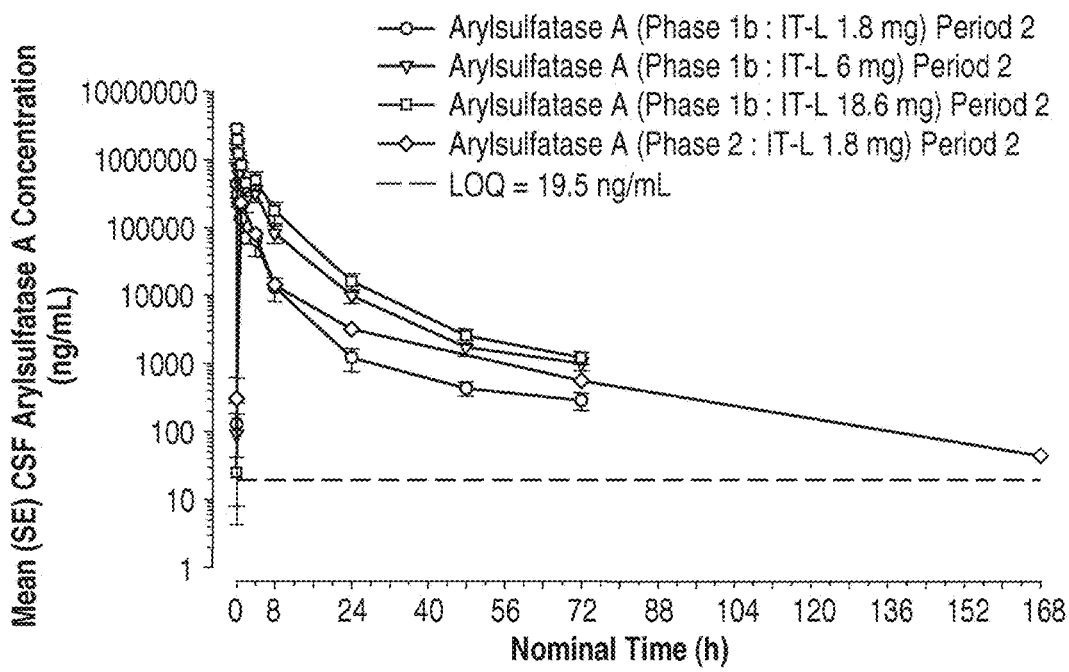
FIG. 4 illustrates exemplary rhASA concentration in CSF after IT-lumbar administration.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Bulking agent: As used herein, the term "bulking agent" refers to a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, sodium chloride, hydroxyethyl starch, lactose, sucrose, trehalose, polyethylene glycol and dextran.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Concurrent immunosuppressant therapy: As used herein, the term "concurrent immunosuppressant therapy" includes any immunosuppressant therapy used as pre-treatment, pre-conditioning or in parallel to a treatment method.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein for the patient to be treated. Each unit contains a predetermined quantity of active material calculated to produce the desired therapeutic effect. It will be understood, however, that the total dosage of the composition will be decided by the attending physician within the scope of sound medical judgment.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodsteam. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease.

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Lyoprotectant: As used herein, the term "lyoprotectant" refers to a molecule that prevents or reduces chemical and/or physical instability of a protein or other substance upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate: a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In some embodiments, a lyoprotectant is a non-reducing sugar, such as trehalose or sucrose.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Lysosomal enzyme deficiency: As used herein, "lysosomal enzyme deficiency" refers to a group of genetic disorders that result from deficiency in at least one of the enzymes that are required to break macromolecules (e.g., enzyme substartes) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents in accordance with the present invention are soluble in its corresponding pharmaceutical composition. It will be appreciated that, while isotonic solutions are generally preferred for parenterally administered drugs, the use of isotonic solutions may limit adequate solubility for some therapeutic agents and, in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated in monkeys. For example, the most common approved CNS bolus formulation composition is saline (150 mM NaCl in water).

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Synthetic CSF: As used herein, the term "synthetic CSF" refers to a solution that has pH, electrolyte composition, glucose content and osmalarity consistent with the cerebrospinal fluid. Synthetic CSF is also referred to as artificial CSF. In some embodiments, synthetic CSF is an Elliott's B solution.

Suitable for CNS delivery: As used herein, the phrase "suitable for CNS delivery" or "suitable for intrathecal delivery" as it relates to the pharmaceutical compositions of the present invention generally refers to the stability, tolerability, and solubility properties of such compositions, as well as the ability of such compositions to deliver an effective amount of the therapeutic agent contained therein to the targeted site of delivery (e.g., the CSF or the brain).

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Therapeutic moiety: As used herein, the term "therapeutic moiety" refers to a portion of a molecule that renders the therapeutic effect of the molecule. In some embodiments, a therapeutic moiety is a polypeptide having therapeutic activity.

Therapeutically effective amount: As used herein, the term "therapeutically effective amount" refers to an amount of a therapeutic protein (e.g., replacement enzyme) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome, Sanfilippo B syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF THE INVENTION

The present invention provides, among other things, improved methods and compositions for effective direct delivery of a therapeutic agent to the central nervous system (CNS). As discussed above, the present invention is based on unexpected discovery that a replacement enzyme (e.g., an ASA protein) for a lysososmal storage disease (e.g., Metachromatic Leukodystrophy Disease) can be directly introduced into the cerebrospinal fluid (CS F) of a subject in need of treatment at a high concentration without inducing substantial adverse effects in the subject. More surprisingly, the present inventors found that the replacement enzyme may be delivered in a simple saline or buffer-based formulation, without using synthetic CSF. Even more unexpectedly, intrathecal delivery according to the present invention does not result in substantial adverse effects, such as severe immune response, in the subject. Therefore, in some embodiments, intrathecal delivery according to the present invention may be used in absence of concurrent immunosuppressant therapy (e.g., without induction of immune tolerance by pre-treatment or pre-conditioning).

In some embodiments, intrathecal delivery according to the present invention permits efficient diffusion across various brain tissues resulting in effective delivery of the replacement enzyme in various target brain tissues in surface, shallow and/or deep brain regions. In some embodiments, intrathecal delivery according to the present invention resulted in sufficient amount of replacement enzymes entering the peripheral circulation. As a result, in some cases, intrathecal delivery according to the present invention resulted in delivery of the replacement enzyme in peripheral tissues, such as liver, heart, spleen and kidney. This discovery is unexpected and can be particular useful for the treatment of lysosomal storage diseases that have both CNS and peripheral components, which would typically require both regular intrathecal administration and intravenous administration. It is contemplated that intrathecal delivery according to the present invention may allow reduced dosing and/or frequency of iv injection without compromising therapeutic effects in treating peripheral symptoms.

The present invention provides various unexpected and beneficial features that allow efficient and convenient delivery of replacement enzymes to various brain target tissues, resulting in effective treatment of lysosomal storage diseases that have CNS indications.

Various aspects of the invention are described in detail in the following sections. The use of sections is not meant to limit the invention. Each section can apply to any aspect of the invention. In this application, the use of "or" means "and/or" unless stated otherwise.

Therapeutic Proteins

In some embodiments, inventive methods and compositions provided by the present invention are used to deliver an arylsulfatase A (ASA) protein to the CNS for treatment of Metachromatic Leukodystrophy Disease. A suitable ASA protein can be any molecule or a portion of a molecule that can substitute for naturally-occurring arylsulfatase A (ASA) protein activity or rescue one or more phenotypes or symptoms associated with ASA-deficiency. In some embodiments, a replacement enzyme suitable for the invention is a polypeptide having an N-terminus and a C-terminus and an amino acid sequence substantially similar or identical to mature human ASA protein.

Typically, human ASA is produced as a precursor molecule that is processed to a mature form. This process generally occurs by removing the 18 amino acid signal peptide. Typically, the precursor form is also referred to as full-length precursor or full-length ASA protein, which contains 507 amino acids. The N-terminal 18 amino acids are cleaved, resulting in a mature form that is 489 amino acids in length. Thus, it is contemplated that the N-terminal 18 amino acids is generally not required for the ASA protein activity. The amino acid sequences of the mature form (SEQ ID NO:1) and full-length precursor (SEQ ID NO:2) of a typical wild-type or naturally-occurring human ASA protein are shown in Table 1.

mature human ASA protein containing one or more amino acid substitutions, deletions, and/or insertions as compared to a wild-type or naturally-occurring ASA protein (e.g., SEQ ID NO:1), while retaining substantial ASA protein activity. Thus, in some embodiments, a therapeutic moiety suitable for the present invention is substantially homologous to mature human ASA protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%. 93%, 94%, 95%, 96%, 97%, 98%, 99% or more homologous to SEQ ID NO:1. In some embodiments, a therapeutic moiety suitable for the present invention is substantially identical to mature human ASA protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a therapeutic moiety suitable for the present invention contains a fragment or a portion of mature human ASA protein.

Alternatively, a replacement enzyme suitable for the present invention is full-length ASA protein. In some embodiments, a suitable replacement enzyme may be a homologue or an analogue of full-length human ASA protein. For example, a homologue or an analogue of full-length human ASA protein may be a modified full-length human ASA protein containing one or more amino acid substitutions, deletions, and/or insertions as compared to a wild-type or naturally-occurring full-length ASA protein (e.g., SEQ ID NO:2), while retaining substantial ASA protein activity. Thus, In some embodiments, a replacement enzyme suitable for the present invention is substantially homologous to full-length human ASA protein (SEQ ID NO:2). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to

TABLE 1

Human Arylsulfatase A

| | |
|---|---|
| Mature Form | RPPNIVLIFADDLGYGDLGCYGHPSSTTPNLDQLAAGGLRFTDFYVPVSLCTPS RAALLTGRLPVRMGMYPGVLVPSSRGGLPLEEVTVAEVLAARGYLTGMAGKWHL GVGPEGAFLPPHQGFHRFLGIPYSHDQGPCQNLTCFPPATPCDGGCDQGLVPIP LLANLSVEAQPPWLPGLEARYMAFAHDLMADAQRQDRPFFLYYASHHTHYPQFS GQSFAERSGRGPFGDSLMELDAAVGTLMTAIGDLGLLEETLVIFTADNGPETMR MSRGGCSGLLRCGKGTTYEGGVREPALAFWPGHIAPGVTHELASSLDLLPTLAA LAGAPLPNVTLDGFDLSPLLLGTGKSPRQSLFFYPSYPDEVRGVFAVRTGKYKA HFFTQGSAHSDTTADPACHASSSLTAHEPPLLYDLSKDPGENYNLLGGVAGATP EVLQALKQLQLLKAQLDAAVTFGPSQVARGEDPALQICCHPGCTPRPACCHCPD PHA (SEQ ID NO: 1) |
| Full-Length Precursor | MGAPRSLLLALAAGLAVARPPNIVLIFADDLGYGDLGCYGHPSSTTPNLDQLAA GGLRFTDFYVPVSLCTPSRAALLTGRLPVRMGMYPGVLVPSSRGGLPLEEVTVA EVLAARGYLTGMAGKWHLGVGPEGAFLPPHQGFHRFLGIPYSHDQGPCQNLTCF PPATPCDGGCDQGLVPIPLLANLSVEAQPPWLPGLEARYMAFAHDLMADAQRQD RPFFLYYASHHTHYPQFSGQSFAERSGRGPFGDSLMELDAAVGTLMTAIGDLGL LEETLVIFTADNGPETMRMSRGGCSGLLRCGKGTTYEGGVREPALAFWPGHIAP GVTHELASSLDLLPTLAALAGAPLPNVTLDGFDLSPLLLGTGKSPRQSLFFYPS YPDEVRGVFAVRTGKYKAHFFTQGSAHSDTTADPACHASSSLTAHEPPLLYDLS KDPGENYNLLGGVAGATPEVLQALKQLQLLKAQLDAAVTFGPSQVARGEDPALQ ICCHPGCTPRPACCHCPDPHA (SEQ ID NO: 2) |

Thus, in some embodiments, a therapeutic moiety suitable for the present invention is mature human ASA protein (SEQ ID NO:1). In some embodiments, a suitable therapeutic moiety may be a homologue or an analogue of mature human ASA protein. For example, a homologue or an analogue of mature human ASA protein may be a modified SEQ ID NO:2. In some embodiments, a replacement enzyme suitable for the present invention is substantially identical to SEQ ID NO:2. In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a replacement enzyme suitable for the present invention contains a fragment or a portion of full-length human ASA protein. As used herein, a full-length ASA protein typically contains signal peptide sequence.

In some embodiments, a therapeutic protein includes a targeting moiety (e.g., a lysosome targeting sequence) and/or a membrane-penetrating peptide. In some embodiments, a targeting sequence and/or a membrane-penetrating peptide is an intrinsic part of the therapeutic moiety (e.g., via a chemical linkage, via a fusion protein). In some embodiments, a targeting sequence contains a mannose-6-phosphate moiety. In some embodiments, a targeting sequence contains an IGF-I moiety. In some embodiments, a targeting sequence contains an IGF-II moiety.

Other Lysosomal Storage Diseases and Replacement Enzymes

It is contemplated that inventive methods and compositions according to the present invention can be used to treat other lysosomal storage diseases, in particular those lysosomal storage diseases having CNS etiology and/or symptoms, including, but are not limited to, aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, .beta.-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten disease, Niemann-Pick disease types A/B, Niemann-Pick disease type C1, Niemann-Pick disease type C2, pycnodysostosis, Schindler disease types I/II, Gaucher disease and sialic acid storage disease.

A detailed review of the genetic etiology, clinical manifestations, and molecular biology of the lysosomal storage diseases are detailed in Scriver et al., eds., The Metabolic and Molecular Basis of Inherited Disease, 7.sup.th Ed., Vol. II, McGraw Hill, (1995). Thus, the enzymes deficient in the above diseases are known to those of skill in the art, some of these are exemplified in Table 2 below:

TABLE 2

| Disease Name | Enzyme Deficiency | Substance Stored |
| --- | --- | --- |
| Pompe Disease | Acid-a1, 4-Glucosidase | Glycogen α□1-4 linked Oligosaccharides |
| GM1 Gangliodsidosis | β-Galactosidase | $GM_1$ Gangliosides |
| Tay-Sachs Disease | β-Hexosaminidase A | $GM_2$ Ganglioside |
| GM2 Gangliosidosis: AB Variant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetyl-glucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| α-Mannosidosis | α-□Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Aspartyl-glucosaminuria | N-Aspartyl-β-Glucosaminidase | Aspartylgluco-samine Asparagines |
| Sialidosis (Mucolipidosis I) | α-Neuraminidase | Sialyloligo-saccharides |
| Galactosialidosis (Goldberg Syndrome) | Lysosomal Protective Protein Deficiency | Sialyloligo-saccharides |
| Schindler Disease | α-N-Acetyl-Galactosaminidase | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

Inventive methods according to the present invention may be used to deliver various other replacement enzymes. As used herein, replacement enzymes suitable for the present invention may include any enzyme that can act to replace at least partial activity of the deficient or missing lysosomal enzyme in a lysosomal storage disease to be treated. In some embodiments, a replacement enzyme is capable of reducing accumulated substance in lysosomes or that can rescue or ameliorate one or more lysosomal storage disease symptoms.

In some embodiments, a suitable replacement enzyme may be any lysosomal enzyme known to be associated with the lysosomal storage disease to be treated. In some embodiments, a suitable replacement enzyme is an enzyme selected from the enzyme listed in Table 2 above.

In some embodiments, a replacement enzyme suitable for the invention may have a wild-type or naturally occurring sequence. In some embodiments, a replacement enzyme suitable for the invention may have a modified sequence having substantial homology or identify to the wild-type or naturally-occurring sequence (e.g., having at least 50%, 55%, 60%, 65%, 70%. 75%, 80%, 85%, 90%, 95%, 98% sequence identity to the wild-type or naturally-occurring sequence).

A replacement enzyme suitable for the present invention may be produced by any available means. For example, replacement enzymes may be recombinantly produced by utilizing a host cell system engineered to express a replacement enzyme-encoding nucleic acid. Alternatively or additionally, replacement enzymes may be produced by activating endogenous genes. Alternatively or additionally, replacement enzymes may be partially or fully prepared by chemical synthesis. Alternatively or additionally, replacements enzymes may also be purified from natural sources.

Where enzymes are recombinantly produced, any expression system can be used. To give but a few examples, known expression systems include, for example, egg, baculovirus, plant, yeast, or mammalian cells.

In some embodiments, enzymes suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, inventive methods according to the present invention are used to deliver replacement enzymes produced from human cells. In some embodiments, inventive methods according to the present invention are used to deliver replacement enzymes produced from CHO cells.

In some embodiments, replacement enzymes delivered using a method of the invention contain a moiety that binds to a receptor on the surface of brain cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a replacement enzyme suitable for the present invention contains M6P residues on the surface of the protein. In some embodiments, a replacement enzyme suitable for the present invention may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable replacement enzymes may be modified by certain enzymes which are capable of catalyzing the transfer of N-acetylglucosamine-L-phosphate from UDP-GlcNAc to the 6' position of α-1,2-linked mannoses on lysosomal enzymes. Methods and compositions for producing and using such enzymes are described by, for example, Canfield et al. in U.S. Pat. No. 6,537,785, and U.S. Pat. No. 6,534,300, each incorporated herein by reference.

In some embodiments, replacement enzymes for use in the present invention may be conjugated or fused to a lysosomal targeting moiety that is capable of binding to a receptor on the surface of brain cells. A suitable lysosomal targeting moiety can be IGF-I, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence).

In some embodiments, replacement enzymes suitable for the present invention have not been modified to enhance delivery or transport of such agents across the BBB and into the CNS.

In some embodiments, a therapeutic protein includes a targeting moiety (e.g., a lysosome targeting sequence) and/or a membrane-penetrating peptide. In some embodiments, a targeting sequence and/or a membrane-penetrating peptide is an intrinsic part of the therapeutic moiety (e.g., via a chemical linkage, via a fusion protein). In some embodiments, a targeting sequence contains a mannose-6-phosphate moiety. In some embodiments, a targeting sequence contains an IGF-I moiety. In some embodiments, a targeting sequence contains an IGF-II moiety.

Formulations

Aqueous pharmaceutical solutions and compositions (i.e., formulations) that are traditionally used to deliver therapeutic agents to the CNS of a subject include unbuffered isotonic saline and Elliott's B solution, which is artificial CSF. A comparison depicting the compositions of CSF relative to Elliott's B solution is included in Table 3 below. As shown in Table 3, the concentration of Elliot's B Solution closely parallels that of the CSF. Elliott's B Solution, however contains a very low buffer concentration and accordingly may not provide the adequate buffering capacity needed to stabilize therapeutic agents (e.g., proteins), especially over extended periods of time (e.g., during storage conditions). Furthermore, Elliott's B Solution contains certain salts which may be incompatible with the formulations intended to deliver some therapeutic agents, and in particular proteins or enzymes. For example, the calcium salts present in Elliott's B Solution are capable of mediating protein precipitation and thereby reducing the stability of the formulation.

TABLE 3

| Solution | Na+ mEq/L | K+ mEq/L | Ca++ mEq/L | Mg++ mEq/L | HCO3− mEq/L | Cl− mEq/L | pH | Phosphorous mg/L | Glucose mg/L |
|---|---|---|---|---|---|---|---|---|---|
| CSF | 117-137 | 2.3 | 2.2 | 2.2 | 22.9 | 113-127 | 7.31 | 1.2-2.1 | 45-80 |
| Elliott's B Sol'n | 149 | 2.6 | 2.7 | 2.4 | 22.6 | 132 | 6.0-7.5 | 2.3 | 80 |

The present invention provides formulations, in either aqueous, pre-lyophilized, lyophilized or reconstituted form, for therapeutic agents that have been formulated such that they are capable of stabilizing, or alternatively slowing or preventing the degradation, of one or more therapeutic agents formulated therewith (e.g., recombinant proteins). In some embodiments, the present formulations provide lyophilization formulation for therapeutic agents. In some embodiments, the present formulations provide aqueous formulations for therapeutic agents. In some embodiments the formulations are stable formulations.

Stable Formulations

As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., preferably for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Stability of the therapeutic agent is of particular importance with respect to the maintenance of the specified range of the therapeutic agent concentration required to enable the agent to serve its intended therapeutic function. Stability of the therapeutic agent may be further assessed relative to the biological activity or physiochemical integrity of the therapeutic agent over extended periods of time. For example, stability at a given time point may be compared against stability at an earlier time point (e.g., upon formulation day 0) or against unformulated therapeutic agent and the results of this comparison expressed as a percentage. Preferably, the pharmaceutical compositions of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the therapeutic agent's biological activity or physiochemical integrity over an extended period of time (e.g., as measured over at least about 6-12 months, at room temperature or under accelerated storage conditions).

The therapeutic agents are preferably soluble in the pharmaceutical compositions of the present invention. The term "soluble" as it relates to the therapeutic agents of the present invention refer to the ability of such therapeutic agents to form a homogenous solution. Preferably the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts.) In some embodiments, the pharmaceutical compositions are formulated such that calcium salts are excluded from such compositions.

Suitable formulations, in either aqueous, pre-lyophilized, lyophilized or reconstituted form, may contain a therapeutic agent of interest at various concentrations. In some embodiments, formulations may contain a protein or therapeutic agent of interest at a concentration in the range of about 0.1 mg/ml to 100 mg/ml (e.g., about 0.1 mg/ml to 80 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 15 mg/ml, about 0.1 mg/ml to 10 mg/ml, about 0.1 mg/ml to 5 mg/ml, about 1 mg/ml to 10 mg/ml, about 1 mg/ml to 20 mg/ml, about 1 mg/ml to 40 mg/ml, about 5 mg/ml to 100 mg/ml, about 5 mg/ml to 50 mg/ml, or about 5 mg/ml to 25 mg/ml). In some embodiments, formulations according to the invention may contain a therapeutic agent at a concentration of approximately 1 mg/ml, 5 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, or 100 mg/ml.

The formulations of the present invention are characterized by their tolerability either as aqueous solutions or as reconstituted lyophilized solutions. As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Many therapeutic agents, and in particular the proteins and enzymes of the present invention, require controlled pH and specific excipients to maintain their solubility and stability in the pharmaceutical compositions of the present invention. Table 4 below identifies typical aspects of protein formulations considered to maintain the solubility and stability of the protein therapeutic agents of the present invention.

TABLE 4

| Parameter | Typical Range/Type | Rationale |
|---|---|---|
| pH | 5 to 7.5 | For stability Sometimes also for solubility |
| Buffer type | acetate, succinate, citrate, histidine, phosphate or Tris | To maintain optimal pH May also affect stability |

TABLE 4-continued

| Parameter | Typical Range/Type | Rationale |
|---|---|---|
| Buffer concentration | 5-50 mM | To maintain pH<br>May also stabilize or add ionic strength |
| Tonicifier | NaCl, sugars, mannitol | To render iso-osmotic or isotonic solutions |
| Surfactant | Polysorbate 20, polysorbate 80 | To stabilize against interfaces and shear |
| Other | Amino acids (e.g. arginine) at tens to hundreds of mM | For enhanced solubility or stability |

Buffers

The pH of the formulation is an additional factor which is capable of altering the solubility of a therapeutic agent (e.g., an enzyme or protein) in an aqueous formulation or for a pre-lyophilization formulation. Accordingly the formulations of the present invention preferably comprise one or more buffers. In some embodiments the aqueous formulations comprise an amount of buffer sufficient to maintain the optimal pH of said composition between about 4.0-8.0 (e.g., about 4.0, 4.5, 5.0, 5.5, 6.0, 6.2, 6.4, 6.5, 6.6, 6.8, 7.0, 7.5, or 8.0). In some embodiments, the pH of the formulation is between about 5.0-7.5, between about 5.5-7.0, between about 6.0-7.0, between about 5.5-6.0, between about 5.5-6.5, between about 5.0-6.0, between about 5.0-6.5 and between about 6.0-7.5. Suitable buffers include, for example acetate, citrate, histidine, phosphate, succinate, tris(hydroxymethyl) aminomethane ("Tris") and other organic acids. The buffer concentration and pH range of the pharmaceutical compositions of the present invention are factors in controlling or adjusting the tolerability of the formulation. In some embodiments, a buffering agent is present at a concentration ranging between about 1 mM to about 150 mM, or between about 10 mM to about 50 mM, or between about 15 mM to about 50 mM, or between about 20 mM to about 50 mM, or between about 25 mM to about 50 mM. In some embodiments, a suitable buffering agent is present at a concentration of approximately 1 mM, 5 mM, 10 mM, 15 mM, 20 mM, 25 mM, 30 mM, 35 mM, 40 mM, 45 mM 50 mM, 75 mM, 100 mM, 125 mM or 150 mM.

Tonicity

In some embodiments, formulations, in either aqueous, pre-lyophilized, lyophilized or reconstituted form, contain an isotonicity agent to keep the formulations isotonic. Typically, by "isotonic" is meant that the formulation of interest has essentially the same osmotic pressure as human blood. Isotonic formulations will generally have an osmotic pressure from about 240 mOsm/kg to about 350 mOsm/kg. Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in aqueous and/or pre-lyophilized formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight. In some embodiments, formulations for lyophilization contain an isotonicity agent to keep the pre-lyophilization formulations or the reconstituted formulations isotonic.

While generally isotonic solutions are preferred for parenterally administered drugs, the use of isotonic solutions may change solubility for some therapeutic agents and in particular may change solubility for some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated. The most common approved CNS bolus formulation composition is saline (about 150 mM NaCl in water).

Stabilizing Agents

In some embodiments, formulations may contain a stabilizing agent, or lyoprotectant, to protect the protein. Typically, a suitable stabilizing agent is a sugar, a non-reducing sugar and/or an amino acid. Exemplary sugars include, but are not limited to, dextran, lactose, mannitol, mannose, sorbitol, raffinose, sucrose and trehalose. Exemplary amino acids include, but are not limited to, arginine, glycine and methionine. Additional stabilizing agents may include sodium chloride, hydroxyethyl starch and polyvinylpyrolidone. The amount of stabilizing agent in the lyophilized formulation is generally such that the formulation will be isotonic. However, hypertonic reconstituted formulations may also be suitable. In addition, the amount of stabilizing agent must not be too low such that an unacceptable amount of degradation/aggregation of the therapeutic agent occurs. Exemplary stabilizing agent concentrations in the formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight. In some embodiments, the ratio of the mass amount of the stabilizing agent and the therapeutic agent is about 1:1. In other embodiments, the ratio of the mass amount of the stabilizing agent and the therapeutic agent can be about 0.1:1, 0.2:1, 0.25:1, 0.4:1, 0.5:1, 1:1, 2:1, 2.6:1, 3:1, 4:1, 5:1, 10:1, or 20:1. In some embodiments, suitable for lyophilization, the stabilizing agent is also a lyoprotectant.

In some embodiments, liquid formulations suitable for the present invention contain amorphous materials. In some embodiments, liquid formulations suitable for the present invention contain a substantial amount of amorphous materials (e.g., sucrose-based formulations). In some embodiments, liquid formulations suitable for the present invention contain partly crystalline/partly amorphous materials.

Bulking Agents

In some embodiments, suitable formulations for lyophilization may further include one or more bulking agents. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%).

Surfactants

In some embodiments, it is desirable to add a surfactant to formulations. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristarnidopropyl-, palmidopropyl-, or isostearamidopropyl-dimethylamine; sodium methyl cocoyl-, or disodium methyl ofeyl-taurate; and the MONA- QUAT™ series (Mona Industries, Inc., Paterson, N.J.), polyethyl glycol, polypropyl glycol, and copolymers of ethylene and propylene glycol (e.g., Pluronics, PF68, etc). Typically, the amount of surfactant added is such that it reduces aggregation of the protein and minimizes the formation of particulates or effervescences. For example, a surfactant may be present in a formulation at a concentration from about 0.001-0.5% (e.g., about 0.005-0.05%, or 0.005-0.01%). In particular, a surfactant may be present in a formulation at a concentration of approximately 0.005%, 0.01%, 0.02%, 0.1%, 0.2%, 0.3%, 0.4%, or 0.5%, etc. Alternatively, or in addition, the surfactant may be added to the lyophilized formulation, pre-lyophilized formulation and/or the reconstituted formulation.

Other pharmaceutically acceptable carriers, excipients or stabilizers such as those described in Remington's Pharmaceutical Sciences 16th edition, Osol, A. Ed. (1980) may be included in the formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include, but are not limited to, additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

Formulations, in either aqueous, pre-lyophilized, lyophilized or reconstituted form, in accordance with the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C., 45° C. etc.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock.

Lyophilization

Inventive methods in accordance with the present invention can be utilized to lyophilize any materials, in particular, therapeutic agents. Typically, a pre-lyophilization formulation further contains an appropriate choice of excipients or other components such as stabilizers, buffering agents, bulking agents, and surfactants to prevent compound of interest from degradation (e.g., protein aggregation, deamidation, and/or oxidation) during freeze-drying and storage. The formulation for lyophilization can include one or more additional ingredients including lyoprotectants or stabilizing agents, buffers, bulking agents, isotonicity agents and surfactants.

After the substance of interest and any additional components are mixed together, the formulation is lyophilized. Lyophilization generally includes three main stages: freezing, primary drying and secondary drying. Freezing is necessary to convert water to ice or some amorphous formulation components to the crystalline form. Primary drying is the process step when ice is removed from the frozen product by direct sublimation at low pressure and temperature. Secondary drying is the process step when bounded water is removed from the product matrix utilizing the diffusion of residual water to the evaporation surface. Product temperature during secondary drying is normally higher than during primary drying. See, Tang X. et al. (2004) "Design of freeze-drying processes for pharmaceuticals: Practical advice," *Pharm. Res.,* 21:191-200; Nail S. L. et al. (2002) "Fundamentals of freeze-drying," in Development and manufacture of protein pharmaceuticals. Nail S. L. editor New York: Kluwer Academic/Plenum Publishers, pp 281-353; Wang et al. (2000) "Lyophilization and development of solid protein pharmaceuticals," *Int. J. Pharm.,* 203:1-60; Williams N. A. et al. (1984) "The lyophilization of pharmaceuticals; A literature review." *J. Parenteral Sci. Technol.,* 38:48-59. Generally, any lyophilization process can be used in connection with the present invention.

In some embodiments, an annealing step may be introduced during the initial freezing of the product. The annealing step may reduce the overall cycle time. Without wishing to be bound by any theories, it is contemplated that the annealing step can help promote excipient crystallization and formation of larger ice crystals due to re-crystallization of small crystals formed during supercooling, which, in turn, improves reconstitution. Typically, an annealing step includes an interval or oscillation in the temperature during freezing. For example, the freeze temperature may be −40° C., and the annealing step will increase the temperature to, for example, −10° C. and maintain this temperature for a set period of time. The annealing step time may range from 0.5 hours to 8 hours (e.g., 0.5, 1.0 1.5, 2.0, 2.5, 3, 4, 6, and 8 hours). The annealing temperature may be between the freezing temperature and 0° C.

Lyophilization may be performed in a container, such as a tube, a bag, a bottle, a tray, a vial (e.g., a glass vial), syringe or any other suitable containers. The containers may be disposable. Lyophilization may also be performed in a large scale or small scale. In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial.

Many different freeze-dryers are available for this purpose such as Hull pilot scale dryer (SP Industries, USA), Genesis (SP Industries) laboratory freeze-dryers, or any freeze-dryers capable of controlling the given lyophilization process parameters. Freeze-drying is accomplished by freezing the formulation and subsequently subliming ice from the frozen content at a temperature suitable for primary drying. Initial freezing brings the formulation to a temperature below about −20° C. (e.g., −50° C., −45° C., −40° C., −35° C., −30° C., −25° C., etc.) in typically not more than about 4 hours (e.g., not more than about 3 hours, not more than about 2.5 hours, not more than about 2 hours). Under this condition, the product temperature is typically below the eutectic point or the collapse temperature of the formulation. Typically, the shelf temperature for the primary drying will range from about −30 to 25° C. (provided the product remains below the melting point during primary drying) at a suitable pressure, ranging typically from about 20 to 250 mTorr. The formulation, size and type of the container holding the sample (e.g., glass vial) and the volume of liquid will mainly dictate the time required for drying, which can range from a few hours to several days. A secondary drying stage is carried out at about 0-60° C., depending primarily on the type and size of container and the type of therapeutic protein employed. Again, volume of liquid will mainly dictate the time required for drying, which can range from a few hours to several days.

As a general proposition, lyophilization will result in a lyophilized formulation in which the moisture content thereof is less than about 5%, less than about 4%, less than about 3%, less than about 2%, less than about 1%, and less than about 0.5%.

Reconstitution

While the pharmaceutical compositions of the present invention are generally in an aqueous form upon administration to a subject, in some embodiments the pharmaceutical compositions of the present invention are lyophilized. Such compositions must be reconstituted by adding one or more diluents thereto prior to administration to a subject. At the desired stage, typically at an appropriate time prior to administration to the patient, the lyophilized formulation may be reconstituted with a diluent such that the protein concentration in the reconstituted formulation is desirable.

Various diluents may be used in accordance with the present invention. In some embodiments, a suitable diluent for reconstitution is water. The water used as the diluent can be treated in a variety of ways including reverse osmosis, distillation, deionization, filtrations (e.g., activated carbon, microfiltration, nanofiltration) and combinations of these treatment methods. In general, the water should be suitable for injection including, but not limited to, sterile water or bacteriostatic water for injection.

Additional exemplary diluents include a pH buffered solution (e.g., phosphate-buffered saline), sterile saline solution, Elliot's solution, Ringer's solution or dextrose solution. Suitable diluents may optionally contain a preservative. Exemplary preservatives include aromatic alcohols such as benzyl or phenol alcohol. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0%, from about 0.5-1.5%, or about 1.0-1.2%.

Diluents suitable for the invention may include a variety of additives, including, but not limited to, pH buffering agents, (e.g. Tris, histidine) salts (e.g., sodium chloride) and other additives (e.g., sucrose) including those described above (e.g. stabilizing agents, isotonicity agents).

According to the present invention, a lyophilized substance (e.g., protein) can be reconstituted to a concentration of at least 25 mg/ml (e.g., at least 50 mg/ml, at least 75 mg/ml, at least 100 mg) and in any ranges there between. In some embodiments, a lyophilized substance (e.g., protein) may be reconstituted to a concentration ranging from about 1 mg/ml to 100 mg/ml (e.g., from about 1 mg/ml to 50 mg/ml, from 1 mg/ml to 100 mg/ml, from about 1 mg/ml to about 5 mg/ml, from about 1 mg/ml to about 10 mg/ml, from about 1 mg/ml to about 25 mg/ml, from about 1 mg/ml to about 75 mg/ml, from about 10 mg/ml to about 30 mg/ml, from about 10 mg/ml to about 50 mg/ml, from about 10 mg/ml to about 75 mg/ml, from about 10 mg/ml to about 100 mg/ml, from about 25 mg/ml to about 50 mg/ml, from about 25 mg/ml to about 75 mg/ml, from about 25 mg/ml to about 100 mg/ml, from about 50 mg/ml to about 75 mg/ml, from about 50 mg/ml to about 100 mg/ml). In some embodiments, the concentration of protein in the reconstituted formulation may be higher than the concentration in the pre-lyophilization formulation. High protein concentrations in the reconstituted formulation are considered to be particularly useful where subcutaneous or intramuscular delivery of the reconstituted formulation is intended. In some embodiments, the protein concentration in the reconstituted formulation may be about 2-50 times (e.g., about 2-20, about 2-10 times, or about 2-5 times) of the pre-lyophilized formulation. In some embodiments, the protein concentration in the reconstituted formulation may be at least about 2 times (e.g., at least about 3, 4, 5, 10, 20, 40 times) of the pre-lyophilized formulation.

Reconstitution according to the present invention may be performed in any container. Exemplary containers suitable for the invention include, but are not limited to, such as tubes, vials, syringes (e.g., single-chamber or dual-chamber), bags, bottles, and trays. Suitable containers may be made of any materials such as glass, plastics, metal. The containers may be disposable or reusable. Reconstitution may also be performed in a large scale or small scale.

In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial. In some embodiments, a suitable container for lyophilization and reconstitution is a dual chamber syringe (e.g., Lyo-Ject,® (Vetter) syringes). For example, a dual chamber syringe may contain both the lyophilized substance and the diluent, each in a separate chamber, separated by a stopper (see Example 5). To reconstitute, a plunger can be attached to the stopper at the diluent side and pressed to move diluent into the product chamber so that the diluent can contact the lyophilized substance and reconstitution may take place as described herein (see Example 5).

The pharmaceutical compositions, formulations and related methods of the invention are useful for delivering a variety of therapeutic agents to the CNS of a subject (e.g., intrathecally, intraventricularly or intracisternally) and for the treatment of the associated diseases. The pharmaceutical compositions of the present invention are particularly useful for delivering proteins and enzymes (e.g., enzyme replacement therapy) to subjects suffering from lysosomal storage disorders. The lysosomal storage diseases represent a group of relatively rare inherited metabolic disorders that result from defects in lysosomal function. The lysosomal diseases are characterized by the accumulation of undigested macromolecules within the lysosomes, which results in an increase in the size and number of such lysosomes and ultimately in cellular dysfunction and clinical abnormalities.

CNS Delivery

It is contemplated that various stable formulations described herein are generally suitable for CNS delivery of therapeutic agents. Stable formulations according to the present invention can be used for CNS delivery via various techniques and routes including, but not limited to, intraparenchymal, intracerebral, intravetricular cerebral (ICV), intrathecal (e.g., IT-Lumbar, IT-cisterna magna) administrations and any other techniques and routes for injection directly or indirectly to the CNS and/or CSF.

Intrathecal Delivery

In some embodiments, a replacement enzyme is delivered to the CNS in a formulation described herein. In some embodiments, a replacement enzyme is delivered to the CNS by administering into the cerebrospinal fluid (CSF) of a subject in need of treatment. In some embodiments, intrathecal administration is used to deliver a desired replacement enzyme (e.g., an ASA protein) into the CSF. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al. Advances in Drug Delivery Systems and Applications in Neurosurgery, 143-192 and Omaya et al., Cancer Drug Delivery, 1: 169-179, the contents of which are incorporated herein by reference.

According to the present invention, an enzyme may be injected at any region surrounding the spinal canal. In some embodiments, an enzyme is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intravetricular Cerebral (ICV) delivery.

In some embodiments, "intrathecal administration" or "intrathecal delivery" according to the present invention refers to lumbar IT administration or delivery, for example, delivered between the third and fourth lumbar (lower back) vertebrae and, more inclusively, the L2-S1 region of the spine. It is contemplated that lumbar IT administration or delivery distinguishes over cisterna magna delivery in that lumbar IT administration or delivery according to our invention provides better and more effective delivery to the distal spinal canal, while cisterna magna delivery, among other things, typically does not deliver well to the distal spinal canal.

Device for Intrathecal Delivery

Figure 56A:
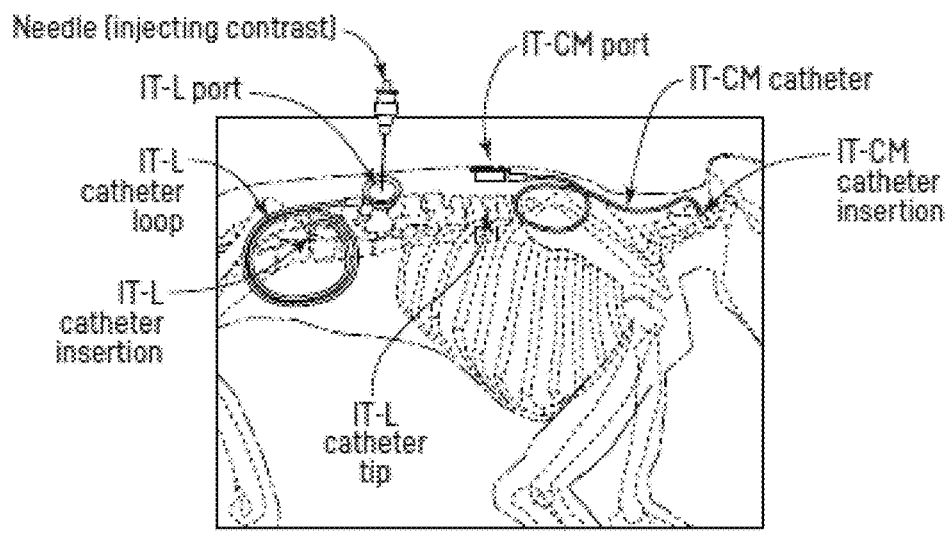
FIG. 56A depicts exemplary locations within a patient's body where an IDDD may be placed.
Figure 56B:
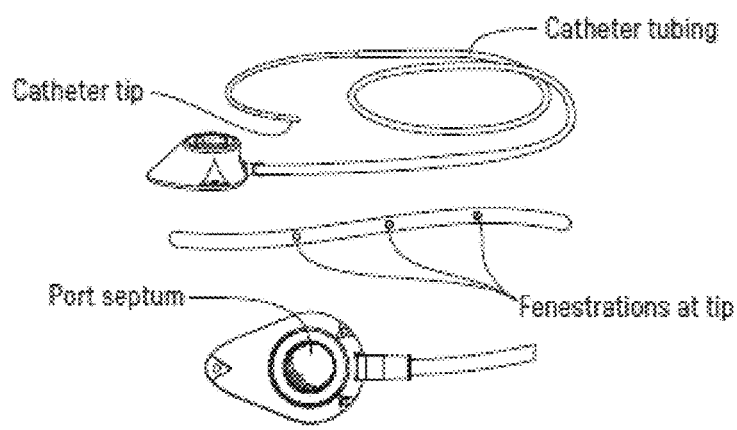
FIG. 56B depicts various components of an intrathecal drug delivery device (IDDD)
Figure 56C:
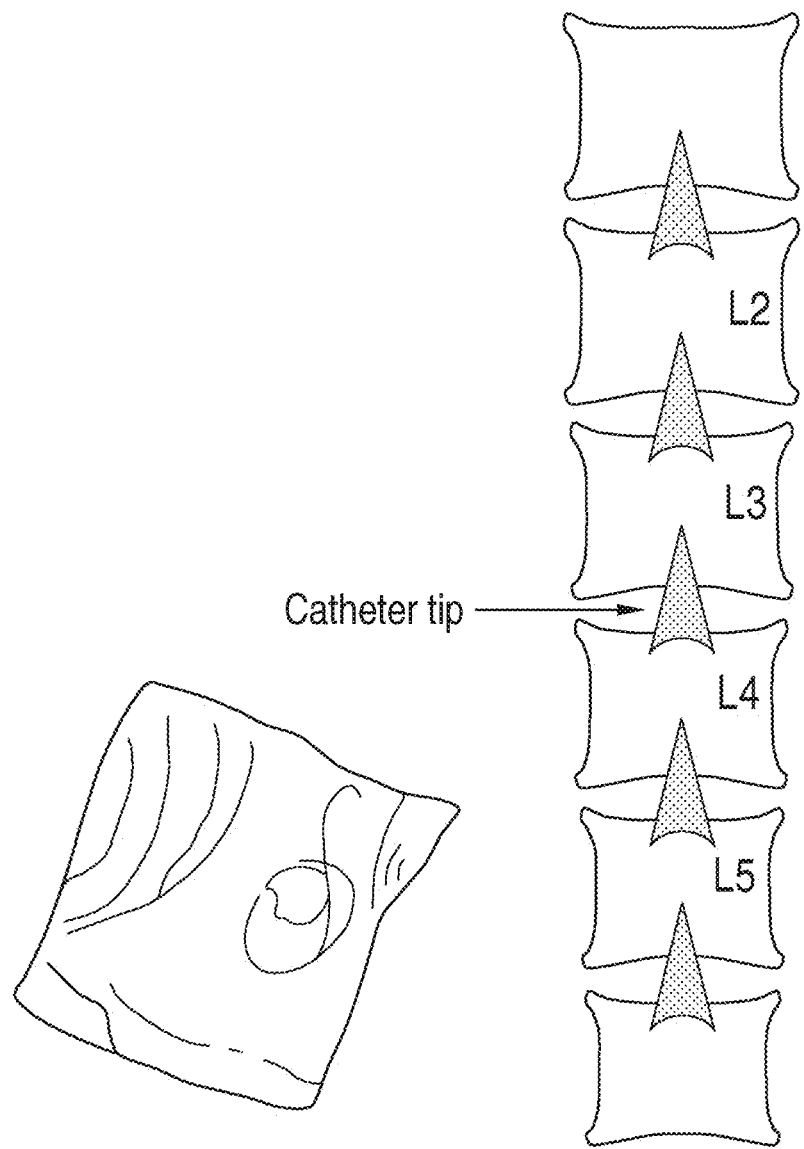
FIG. 56C depicts an exemplary insertion location within a patient's body for IT-lumbar injection.

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example shown in FIG. 55, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4) (FIG. 56C).

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before IT administration. In those cases, a suitable single dose volume may be e.g., more than about 3 ml, 4 ml, 5 ml, 6 ml, 7 ml, 8 ml, 9 ml, 10 ml, 15 ml, or 20 ml.

Various other devices may be used to effect intrathecal administration of a therapeutic composition. For example, formulations containing desired enzymes may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions or formulations to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses.

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In one embodiment of the invention, the enzyme is administered by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger. In some embodiments, injection into the third and fourth smaller ventricles can also be made.

In yet another embodiment, the pharmaceutical compositions used in the present invention are administered by injection into the cisterna magna, or lumbar area of a subject.

In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

As used herein, the term "sustained delivery" refers to continual delivery of a pharmaceutical formulation of the invention in vivo over a period of time following administration, preferably at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

Delivery to Target Tissues

As discussed above, one of the surprising and important features of the present invention is that therapeutic agents, in particular, replacement enzymes administered using inventive methods and compositions of the present invention are able to effectively and extensively diffuse across the brain surface and penetrate various layers or regions of the brain, including deep brain regions. In addition, inventive methods and compositions of the present invention effectively deliver therapeutic agents (e.g., an ASA enzyme) to various tissues, neurons or cells of spinal cord, including the lumbar region, which is hard to target by existing CNS delivery methods such as ICV injection. Furthermore, inventive methods and compositions of the present invention deliver sufficient amount of therapeutic agents (e.g., an ASA enzyme) to blood stream and various peripheral organs and tissues.

Thus, in some embodiments, a therapeutic protein (e.g., an ASA enzyme) is delivered to the central nervous system of a subject. In some embodiments, a therapeutic protein (e.g., an ASA enzyme) is delivered to one or more of target tissues of brain, spinal cord, and/or peripheral organs. As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Brain Target Tissues

In general, the brain can be divided into different regions, layers and tissues. For example, meningeal tissue is a system of membranes which envelops the central nervous system, including the brain. The meninges contain three layers, including dura matter, arachnoid matter, and pia matter. In general, the primary function of the meninges and of the cerebrospinal fluid is to protect the central nervous system.

In some embodiments, a therapeutic protein in accordance with the present invention is delivered to one or more layers of the meninges.

The brain has three primary subdivisions, including the cerebrum, cerebellum, and brain stem. The cerebral hemispheres, which are situated above most other brain structures and are covered with a cortical layer. Underneath the cerebrum lies the brainstem, which resembles a stalk on which the cerebrum is attached. At the rear of the brain, beneath the cerebrum and behind the brainstem, is the cerebellum.

The diencephalon, which is located near the midline of the brain and above the mesencephalon, contains the thalamus, metathalamus, hypothalamus, epithalamus, prethalamus, and pretectum. The mesencephalon, also called the midbrain, contains the tectum, tegumentum, ventricular mesocoelia, and cerebral peduncels, the red nucleus, and the cranial nerve III nucleus. The mesencephalon is associated with vision, hearing, motor control, sleep/wake, alertness, and temperature regulation.

Regions of tissues of the central nervous system, including the brain, can be characterized based on the depth of the tissues. For example, CNS (e.g., brain) tissues can be characterized as surface or shallow tissues, mid-depth tissues, and/or deep tissues.

According to the present invention, a therapeutic protein (e.g., a replacement enzyme) may be delivered to any appropriate brain target tissue(s) associated with a particular disease to be treated in a subject. In some embodiments, a therapeutic protein (e.g., a replacement enzyme) in accordance with the present invention is delivered to surface or shallow brain target tissue. In some embodiments, a therapeutic protein in accordance with the present invention is delivered to mid-depth brain target tissue. In some embodiments, a therapeutic protein in accordance with the present invention is delivered to deep brain target tissue. In some embodiments, a therapeutic protein in accordance with the present invention is delivered to a combination of surface or shallow brain target tissue, mid-depth brain target tissue, and/or deep brain target tissue. In some embodiments, a therapeutic protein in accordance with the present invention is delivered to a deep brain tissue at least 4 mm, 5 mm, 6 mm, 7 mm, 8 mm, 9 mm, 10 mm or more below (or internal to) the external surface of the brain.

In some embodiments, therapeutic agents (e.g., enzymes) are delivered to one or more surface or shallow tissues of cerebrum. In some embodiments, the targeted surface or shallow tissues of the cerebrum are located within 4 mm from the surface of the cerebrum. In some embodiments, the targeted surface or shallow tissues of the cerebrum are selected from pia mater tissues, cerebral cortical ribbon tissues, hippocampus, Virchow Robin space, blood vessels within the VR space, the hippocampus, portions of the hypothalamus on the inferior surface of the brain, the optic nerves and tracts, the olfactory bulb and projections, and combinations thereof.

In some embodiments, therapeutic agents (e.g., enzymes) are delivered to one or more deep tissues of the cerebrum. In some embodiments, the targeted surface or shallow tissues of the cerebrum are located 4 mm (e.g., 5 mm, 6 mm, 7 mm, 8 mm, 9 mm, or 10 mm) below (or internal to) the surface of the cerebrum. In some embodiments, targeted deep tissues of the cerebrum include the cerebral cortical ribbon. In some embodiments, targeted deep tissues of the cerebrum include one or more of the diencephalon (e.g., the hypothalamus, thalamus, prethalamus, subthalamus, etc.), metencephalon, lentiform nuclei, the basal ganglia, caudate, putamen, amygdala, globus pallidus, and combinations thereof.

In some embodiments, therapeutic agents (e.g., enzymes) are delivered to one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, therapeutic agents (e.g., enzymes) are delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In some embodiments, therapeutic agents (e.g., enzymes) are delivered to one or more tissues of the brainstem. In some embodiments, the targeted one or more tissues of the brainstem include brain stem white matter tissue and/or brain stem nuclei tissue.

In some embodiments, therapeutic agents (e.g., enzymes) are delivered to various brain tissues including, but not limited to, gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In some embodiments, therapeutic agents (e.g., enzymes) are delivered to various cells in the brain including, but not limited to, neurons, glial cells, perivascular cells and/or meningeal cells. In some embodiments, a therapeutic protein is delivered to oligodendrocytes of deep white matter.

Spinal Cord

In general, regions or tissues of the spinal cord can be characterized based on the depth of the tissues. For example, spinal cord tissues can be characterized as surface or shallow tissues, mid-depth tissues, and/or deep tissues.

In some embodiments, therapeutic agents (e.g., enzymes) are delivered to one or more surface or shallow tissues of the spinal cord. In some embodiments, a targeted surface or shallow tissue of the spinal cord is located within 4 mm from the surface of the spinal cord. In some embodiments, a targeted surface or shallow tissue of the spinal cord contains pia matter and/or the tracts of white matter.

In some embodiments, therapeutic agents (e.g., enzymes) are delivered to one or more deep tissues of the spinal cord. In some embodiments, a targeted deep tissue of the spinal cord is located internal to 4 mm from the surface of the spinal cord. In some embodiments, a targeted deep tissue of the spinal cord contains spinal cord grey matter and/or ependymal cells.

In some embodiments, therapeutic agents (e.g., enzymes) are delivered to neurons of the spinal cord.

Peripheral Target Tissues

As used herein, peripheral organs or tissues refer to any organs or tissues that are not part of the central nervous system (CNS). Peripheral target tissues may include, but are not limited to, blood system, liver, kidney, heart, endothelium, bone marrow and bone marrow derived cells, spleen, lung, lymph node, bone, cartilage, ovary and testis. In some embodiments, a therapeutic protein (e.g., a replacement enzyme) in accordance with the present invention is delivered to one or more of the peripheral target tissues.

Biodistribution and Bioavailability

In various embodiments, once delivered to the target tissue, a therapeutic agent (e.g., an ASA enzyme) is localized intracellularly. For example, a therapeutic agent (e.g., enzyme) may be localized to exons, axons, lysosomes, mitochondria or vacuoles of a target cell (e.g., neurons such as Purkinje cells). For example, in some embodiments intrathecally-administered enzymes demonstrate translocation dynamics such that the enzyme moves within the perivascular space (e.g., by pulsation-assisted convective mechanisms). In addition, active axonal transport mechanisms relating to the association of the administered protein or enzyme with neurofilaments may also contribute to or otherwise facilitate the distribution of intrathecally-administered proteins or enzymes into the deeper tissues of the central nervous system.

In some embodiments, a therapeutic agent (e.g., an ASA enzyme) delivered according to the present invention may achieve therapeutically or clinically effective levels or activities in various targets tissues described herein. As used herein, a therapeutically or clinically effective level or activity is a level or activity sufficient to confer a therapeutic effect in a target tissue. The therapeutic effect may be objective (i.e., measurable by some test or marker) or subjective (i.e., subject gives an indication of or feels an effect). For example, a therapeutically or clinically effective level or activity may be an enzymatic level or activity that is sufficient to ameliorate symptoms associated with the disease in the target tissue (e.g., GAG storage).

In some embodiments, a therapeutic agent (e.g., a replacement enzyme) delivered according to the present invention may achieve an enzymatic level or activity that is at least 5%, 10%, 20%, 30%, 40%, 50%, 60%, 70%, 80%, 90%, 95% of the normal level or activity of the corresponding lysosomal enzyme in the target tissue. In some embodiments, a therapeutic agent (e.g., a replacement enzyme) delivered according to the present invention may achieve an enzymatic level or activity that is increased by at least 1-fold, 2-fold, 3-fold, 4-fold, 5-fold, 6-fold, 7-fold, 8-fold, 9-fold or 10-fold as compared to a control (e.g., endogenous levels or activities without the treatment). In some embodiments, a therapeutic agent (e.g., a replacement enzyme) delivered according to the present invention may achieve an increased enzymatic level or activity at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg in a target tissue.

In some embodiments, inventive methods according to the present invention are particularly useful for targeting the lumbar region. In some embodiments, a therapeutic agent (e.g., a replacement enzyme) delivered according to the present invention may achieve an increased enzymatic level or activity in the lumbar region of at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In general, therapeutic agents (e.g., replacement enzymes) delivered according to the present invention have sufficiently long half time in CSF and target tissues of the brain, spinal cord, and peripheral organs. In some embodiments, a therapeutic agent (e.g., a replacement enzyme) delivered according to the present invention may have a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, up to 3 days, up to 7 days, up to 14 days, up to 21 days or up to a month. In some embodiments, In some embodiments, a therapeutic agent (e.g., a replacement enzyme) delivered according to the present invention may retain detectable level or activity in CSF or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, or a week following administration. Detectable level or activity may be determined using various methods known in the art.

In certain embodiments, a therapeutic agent (e.g., a replacement enzyme) delivered according to the present invention achieves a concentration of at least 30 µg/ml in the CNS tissues and cells of the subject following administration (e.g., one week, 3 days, 48 hours, 36 hours, 24 hours, 18 hours, 12 hours, 8 hours, 6 hours, 4 hours, 3 hours, 2 hours, 1 hour, 30 minutes, or less, following intrathecal administration of the pharmaceutical composition to the subject). In certain embodiments, a therapeutic agent (e.g., a replacement enzyme) delivered according to the present invention achieves a concentration of at least 20 µg/ml, at least 15 µg/ml, at least 10 µg/ml, at least 7.5 µg/ml, at least 5 µg/ml, at least 2.5 µg/ml, at least 1.0 µg/ml or at least 0.5 µg/ml in the targeted tissues or cells of the subject (e.g., brain tissues or neurons) following administration to such subject (e.g., one week, 3 days, 48 hours, 36 hours, 24 hours, 18 hours, 12 hours, 8 hours, 6 hours, 4 hours, 3 hours, 2 hours, 1 hour, 30 minutes, or less following intrathecal administration of such pharmaceutical compositions to the subject).

Treatment of Metachromatic Leukodystrophy Disease (MLD)

Metachromatic Leukodystrophy Disease (MLD), is an autosomal recessive disorder resulting from a deficiency of the enzyme Arylsulfatease A (ASA). ASA, which is encoded by the ARSA gene in humans, is an enzyme that breaks down cerebroside 3-sulfate or sphingolipid 3-O-sulfogalactosylceramide (sulfatide) into cerebroside and sulfate. In the absence of the enzyme, sulfatides accumulate in the nervous system (e.g., myelin sheaths, neurons and glial cells) and to a lesser extent in visceral organs. The consequence of these molecular and cellular events is progressive demyelination and axonal loss within the CNS and PNS, which is accompanied clinically by severe motor and cognitive dysfunction.

A defining clinical feature of this disorder is central nervous system (CNS) degeneration, which results in cognitive impairment (e.g., mental retardation, nervous disorders, and blindness, among others).

MLD can manifest itself in young children (Late-infantile form), where affected children typically begin showing symptoms just after the first year of life (e.g., at about 15-24 months), and generally do not survive past the age of 5 years. MLD can manifest itself in children (Juvenile form), where affected children typically show cognitive impairment by about the age of 3-10 years, and life-span can vary (e.g., in the range of 10-15 years after onset of symptoms). MLD can manifest itself in adults (Adult-onset form) and can appear in individuals of any age (e.g., typically at age 16 and later) and the progression of the disease can vary greatly.

Compositions and methods of the present invention may be used to effectively treat individuals suffering from or susceptible to MLD. The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease. Exemplary symptoms include, but are not limited to, intracranial pressure, hydrocephalus ex vacuo, accumulated sulfated glycolipids in the myelin sheaths in the central and peripheral nervous system and in visceral organs, progressive demyelination and axonal loss within the CNS and PNS, and/or motor and cognitive dysfunction.

In some embodiments, treatment refers to partially or complete alleviation, amelioration, relief, inhibition, delaying onset, reducing severity and/or incidence of neurological impairment in an MLD patient. As used herein, the term "neurological impairment" includes various symptoms associated with impairment of the central nervous system (e.g., the brain and spinal cord). In some embodiments, various symptoms of MLD are associated with impairment of the peripheral nervous system (PNS). In some embodiments, neurological impairment in an MLD patient is characterized by decline in gross motor function. It will be appreciated that gross motor function may be assessed by any appropriate method. For example, in some embodiments, gross motor function is measured as the change from a baseline in motor function using the Gross Motor Function Measure-88 (GMFM-88) total raw score.

In some embodiments, treatment refers to decreased sulfatide accumulation in various tissues. In some embodiments, treatment refers to decreased sulfatide accumulation in brain target tissues, spinal cord neurons, and/or peripheral target tissues. In certain embodiments, sulfatide accumulation is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, sulfatide accumulation is decreased by at least 1-fold, 2-fold, 3-fold, 4-fold, 5-fold, 6-fold, 7-fold, 8-fold, 9-fold or 10-fold as compared to a control. It will be appreciated that sulfatide storage may be assessed by any appropriate method. For example, in some embodiments, sulfatide storage is measured by alcian blue staining. In some embodiments, sulfatide storage is measured by LAMP-1 staining.

In some embodiments, treatment refers to reduced vacuolization in neurons (e.g., neurons containing Purkinje cells). In certain embodiments, vacuolization in neurons is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, vacuolization is decreased by at least 1-fold, 2-fold, 3-fold, 4-fold, 5-fold, 6-fold, 7-fold, 8-fold, 9-fold or 10-fold as compared to a control.

In some embodiments, treatment refers to increased ASA enzyme activity in various tissues. In some embodiments, treatment refers to increased ASA enzyme activity in brain target tissues, spinal cord neurons and/or peripheral target tissues. In some embodiments, ASA enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900% 1000% or more as compared to a control. In some embodiments, ASA enzyme activity is increased by at least 1-fold, 2-fold, 3-fold, 4-fold, 5-fold, 6-fold, 7-fold, 8-fold, 9-fold or 10-fold as compared to a control. In some embodiments, increased ASA enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In some embodiments, ASA enzymatic activity is increased in the lumbar region. In some embodiments, increased ASA enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, 10,000 nmol/hr/mg, or more.

In some embodiments, treatment refers to decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%. 85%, 90%, 95%, 100% or more as compared to a control. In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with the same form MLD (e.g., late-infantile, juvenile, or adult-onset form), who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having MLD or having the potential to develop MLD. The individual can have residual endogenous ASA expression and/or activity, or no measurable activity. For example, the individual having MLD may have ASA expression levels that are less than about 30-50%, less than about 25-30%, less than about 20-25%, less than about 15-20%, less than about 10-15%, less than about 5-10%, less than about 0.1-5% of normal ASA expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

Immune Tolerance

Generally, intrathecal administration of a therapeutic agent (e.g., a replacement enzyme) according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

In some embodiments, intrathecal administration of therapeutic agents can mount an immune response against these agents. Thus, in some embodiments, it may be useful to render the subject receiving the replacement enzyme tolerant to the enzyme replacement therapy. Immune tolerance may be induced using various methods known in the art. For example, an initial 30-60 day regimen of a T-cell immunosuppressive agent such as cyclosporin A (CsA) and an antiproliferative agent, such as, azathioprine (Aza), combined with weekly intrathecal infusions of low doses of a desired replacement enzyme may be used.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Administration

Inventive methods of the present invention contemplate single as well as multiple administrations of a therapeutically effective amount of the therapeutic agents (e.g., replacement enzymes) described herein. Therapeutic agents (e.g., replacement enzymes) can be administered at regular intervals, depending on the nature, severity and extent of the subject's condition (e.g., a lysosomal storage disease). In some embodiments, a therapeutically effective amount of the therapeutic agents (e.g., replacement enzymes) of the present invention may be administered intrathecally periodically at regular intervals (e.g., once every year, once every six months, once every five months, once every three months, bimonthly (once every two months), monthly (once every month), biweekly (once every two weeks), weekly).

In some embodiments, intrathecal administration may be used in conjunction with other routes of administration (e.g., intravenous, subcutaneously, intramuscularly, parenterally, transdermally, or transmucosally (e.g., orally or nasally)). In some embodiments, those other routes of administration (e.g., intravenous administration) may be performed no more frequent than biweekly, monthly, once every two months, once every three months, once every four months, once every five months, once every six months, annually administration.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

In some embodiments, the therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, the therapeutically effective dose is greater than about 0.1 mg/kg brain weight, greater than about 0.5 mg/kg brain weight, greater than about 1.0 mg/kg brain weight, greater than about 3 mg/kg brain weight, greater than about 5 mg/kg brain weight, greater than about 10 mg/kg brain weight, greater than about 15 mg/kg brain weight, greater than about 20 mg/kg brain weight, greater than about 30 mg/kg brain weight, greater than about 40 mg/kg brain weight, greater than about 50 mg/kg brain weight, greater than about 60 mg/kg brain weight, greater than about 70 mg/kg brain weight, greater than about 80 mg/kg brain weight, greater than about 90 mg/kg brain weight, greater than about 100 mg/kg brain weight, greater than about 150 mg/kg brain weight, greater than about 200 mg/kg brain weight, greater than about 250 mg/kg brain weight, greater than about 300 mg/kg brain weight, greater than about 350 mg/kg brain weight, greater than about 400 mg/kg brain weight, greater than about 450 mg/kg brain weight, greater than about 500 mg/kg brain weight.

In some embodiments, the therapeutically effective dose may also be defined by mg/kg body weight. As one skilled in the art would appreciate, the brain weights and body weights can be correlated. Dekaban A S. "Changes in brain weights during the span of human life: relation of brain weights to body heights and body weights," Ann Neurol 1978; 4:345-56. Thus, in some embodiments, the dosages can be converted as shown in Table 5.

TABLE 5

Correlation between Brain Weights, body weights and ages of males

| Age (year) | Brain weight (kg) | Body weight (kg) |
| --- | --- | --- |
| 3 (31-43 months) | 1.27 | 15.55 |
| 4-5 | 1.30 | 19.46 |

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5:10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

Kits

The present invention further provides kits or other articles of manufacture which contains the formulation of the present invention and provides instructions for its reconstitution (if lyophilized) and/or use. Kits or other articles of manufacture may include a container, an IDDD, a catheter and any other articles, devices or equipment useful in interthecal administration and associated surgery. Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to protein concentrations as described above. The label may further indicate that the formulation is useful or intended for, for example, IT administration. In some embodiments, a container may contain a single dose of a stable formulation containing a therapeutic agent (e.g., a replacement enzyme). In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 25 mg/ml, at least 50 mg/ml, at least 75 mg/ml, at least 100 mg/ml). Kits or other articles of manufacture may further include other materials desirable from a commercial and user standpoint, including other buffers, diluents, filters, needles, IDDDs, catheters, syringes, and package inserts with instructions for use.

The invention will be more fully understood by reference to the following examples. They should not, however, be construed as limiting the scope of the invention. All literature citations are incorporated by reference.

EXAMPLES

Example 1: Toxicology of it Administered Arylsulfatase A

To assess the ability of other intrathecally-administered recombinant enzymes to distribute into the cells and tissues of the CNS, GLP study was conducted to evaluate repeat dose intrathecal (IT) administration of recombinantly-prepared human arylsulfatase A (rhASA) from a toxicology and safety pharmacology perspective over a one-month period in juvenile (less than 12 months of age) cynomolgus monkeys. The formulation of rhASA was prepared and formulated in a vehicle of 154 mM NaCl, 0.005% polysorbate 20 at a pH of 6.0.

To achieve this, nine male and nine female juvenile cynomolgus monkeys were randomly assigned by body weight to one of three treatment groups as shown in the following Table 6. The animals (with the exception of 1 male animal for Dose 1) received 0.6 mL short-term IT infusion of 0, 3 or 31 mg/mL of rhASA (total dose of 0, 1.8 or 18.6 mg) every other week for a total of three doses per animal. Body weights, clinical observations, neurological and physical examinations, clinical pathology, ophthalmologic examinations, and toxicokinetic sampling were monitored. All of the animals were necropsied on Day 29, 30 or 31 (~24 hours after the last IT dose). Selected tissues were harvested, saved and examined microscopically.

TABLE 6

| Group | Number of Animals | Nominal Dose Concentration (mg/mL) | Dose Volume (mL) | Administered Dose (mg) |
|---|---|---|---|---|
| 1 | 3M, 3F | 0 | 0.6 | 0 |
| 2 | 3M, 3F | 3 | 0.6 | 1.8 |
| 3 | 3M, 3F | 31 | 0.6 | 18.6 |

Figure 24:
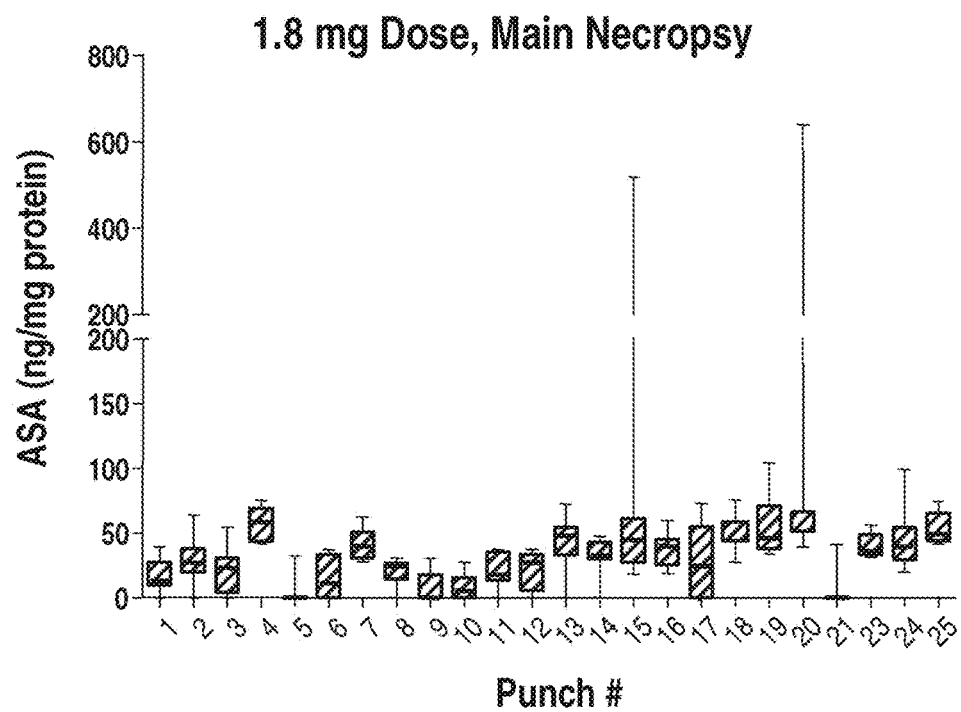
FIG. 24 illustrates exemplary concentration of rhASA in brain punches of juvenile cynomolgus monkeys following EOW IT dosing of rhASA at 1.8 mg/dose for 6-months—main necropsy.
Figure 25:
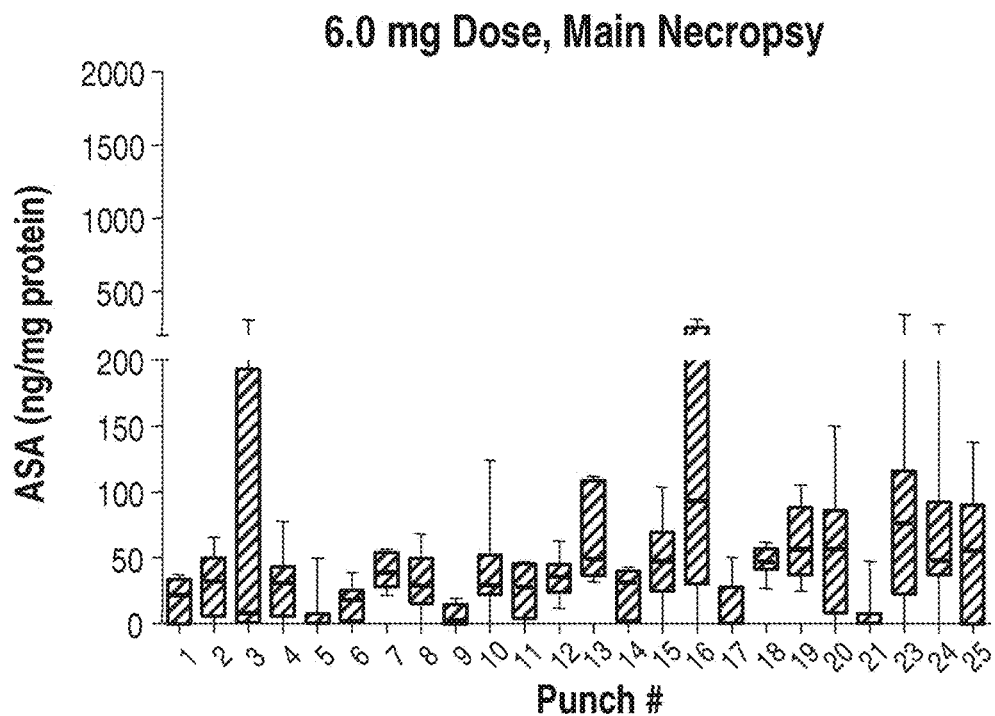
FIG. 25 illustrates exemplary concentration of rhASA in brain punches of juvenile cynomolgus monkeys following EOW IT Dosing of rhASA at 6.0 mg/dose for 6-months—main necropsy.

The concentrations of rhASA detected in the CNS tissues of the cynomolgus monkeys were analyzed by ELISA and compared to a therapeutic target of 10% of normal human rhASA concentrations, corresponding to approximately 2.5 ng/mg of tissue. Tissue samples or punches were extracted from different areas of the brains of the cynomolgus monkeys and further analyzed for the presence of rhASA. FIG. 24 illustrates the tissues from which the punches were extracted. The punched tissue samples reflected an increase in the concentrations of rhASA, as reflected in FIGS. 25A-G, with a deposition gradient from the cerebral cortex to the deep white matter and deep gray matter.

Figure 26:
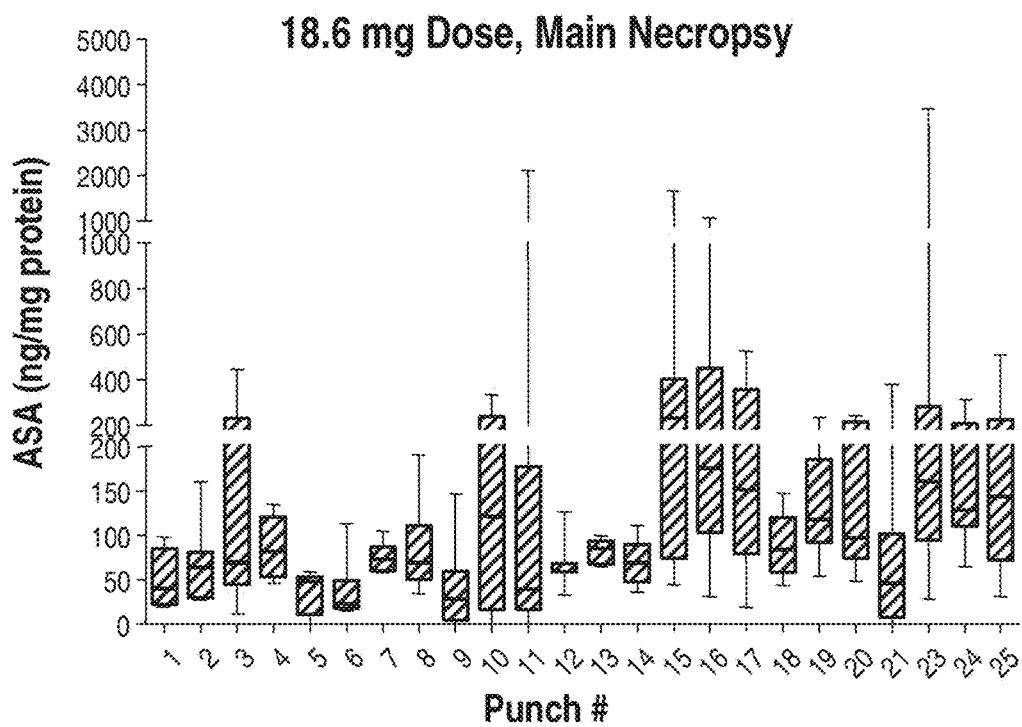
FIG. 26 illustrates exemplary concentration of rhASA in brain punches of juvenile cynomolgus monkeys following EOW IT dosing of rhASA at 18.6 mg/dose for 6-months—main necropsy.

Concentrations of rhASA detected using the same punch from both the IT and ICV routes of administration for six monkeys administered the 18.6 mg dose of rhASA, are illustrated in FIGS. 26A-B. The concentrations of rhASA detected in the deep white matter (FIG. 25A) and in the deep grey matter (FIG. 26B) brain tissues of adult and juvenile cynomolgus monkeys intrathecally-(IT) or intracerebroventricularly-(ICV) administered rhASA were comparable.

Figure 27:
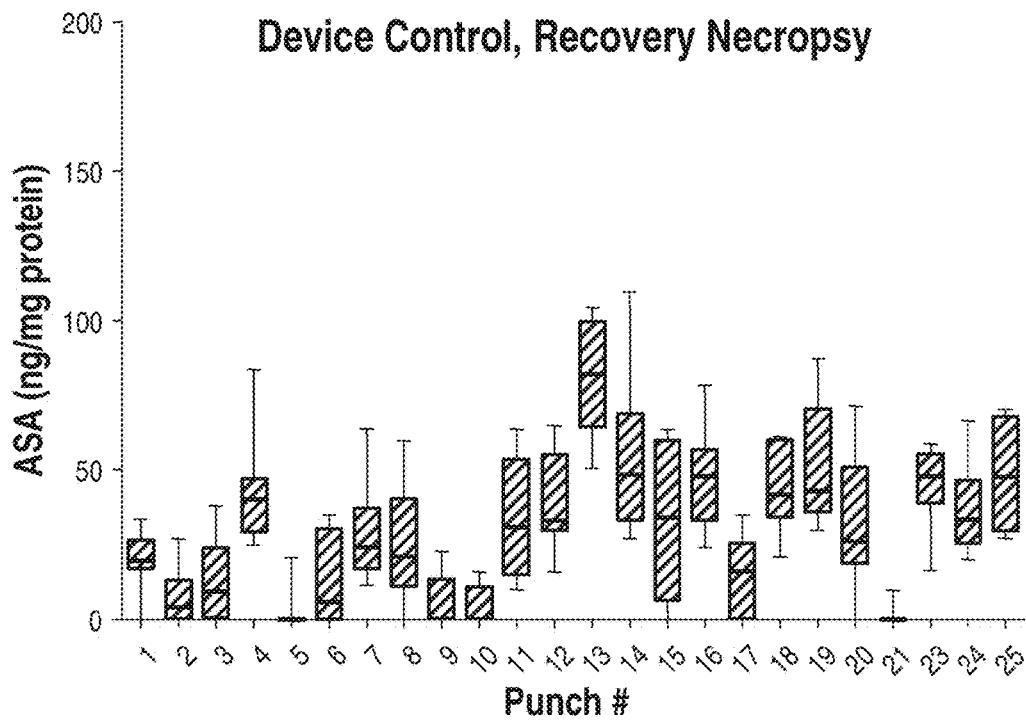
FIG. 27 illustrates exemplary concentration of ASA in brain punches of juvenile cynomolgus monkeys following EOW IT dosing (PBS-control) for 6-months—recovery necropsy.

The punched tissue samples extracted from the brains of adult and juvenile cynomolgus monkeys were then analyzed to determine the concentrations of rhASA deposited in the extracted tissue sample, and to compare such concentrations to the therapeutic target concentration of 2.5 ng rhASA per mg protein (corresponding to 10% of the normal concentration of rhASA in a healthy subject). As illustrated in FIG. 27A, in each tissue sample punch analyzed the 18.6 mg dose of IT-administered rhASA resulted in an rhASA concentration which exceeded the target therapeutic concentration of 2.5 ng/mg of protein. Similarly, when a 1.8 mg dose of rhASA was IT-administered to juvenile cynomolgus monkeys, each tissue sample punch analyzed demonstrated a concentration of rhASA either within or exceeding the therapeutic concentration of 2.5 ng/mg of protein and the median rhASA concentrations were above the therapeutic target for all tissue punches tested (FIG. 27B).

Figure 28:
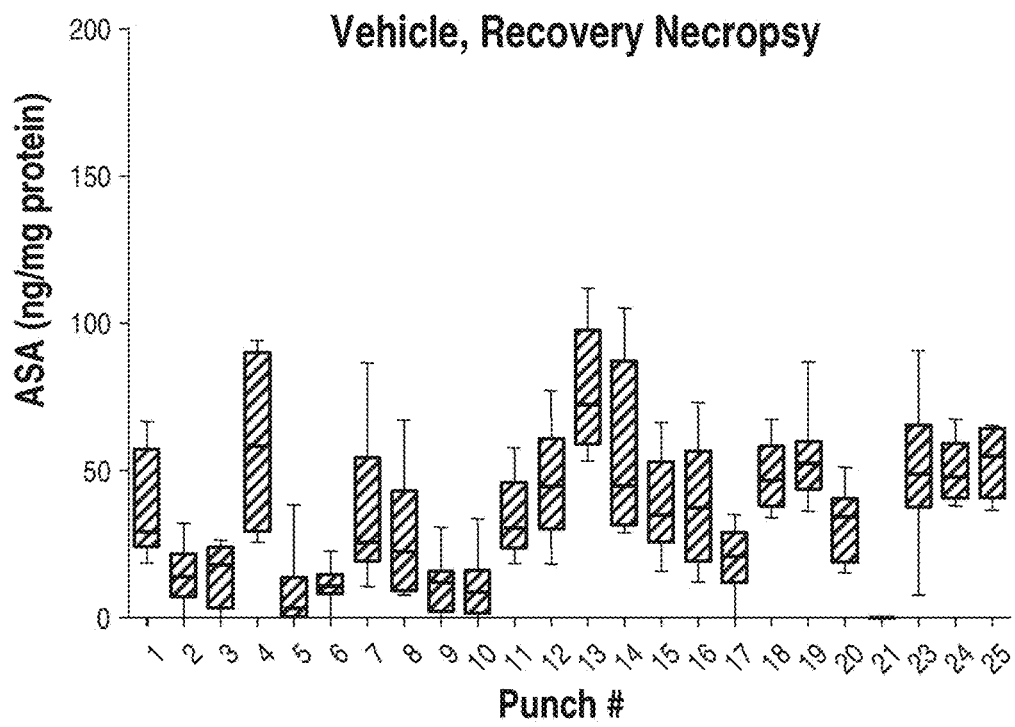
FIG. 28 illustrates exemplary concentration of rhASA in brain punches of juvenile cynomolgus monkeys following EOW IT dosing of vehicle for 6-months—recovery necropsy.

To determine whether IT-administered rhASA was distributing to the relevant cells, tissue was analyzed from the deep white matter of a cynomolgus monkey IT-administered 1.8 mg of ASA, from the area illustrated in FIG. 28A. Immunostaining of the deep white matter tissue revealed distribution of rhASA in the cynomolgus monkey in oligodendrocyte cells, as illustrated by FIG. 28B. Similarly, FIG. 28C illustrates that the IT-administered rhrASA demonstrated co-localization in the deep white matter tissues of the cynomolgus monkey. In particular, under staining co-localization in target organelles, such as the lysosome, is evident (FIG. 28C), supporting the conclusion that IT-administered rhASA is capable of distributing to the relevant cells, tissues and organelles of the CNS, including the lysosomes of oligodendrocytes. The foregoing supports the conclusion that the difference between ICV and IT delivery was also found to be minimal for rhASA delivery.

Example 2: Biodistribution with Radio-Labeled Protein rhASA labeled with the positron emitter $^{124}$I was prepared and formulated in a vehicle of 154 mM NaCl, 0.005% polysorbate 20 at a pH of 6.0. A volume of the formulation equivalent to 3 mg of rhASA (corresponding to approximately 38 mg/kg of brain) was administered to adult cynomolgus monkeys via intracerebroventricular (ICV) and intrathecal (IT) routes of administration. The cynomolgus monkeys were subject to high-resolution PET scan imaging studies (microPET P4) to determine distribution of the administered $^{124}$I-labeled rhASA.

Figure 29:
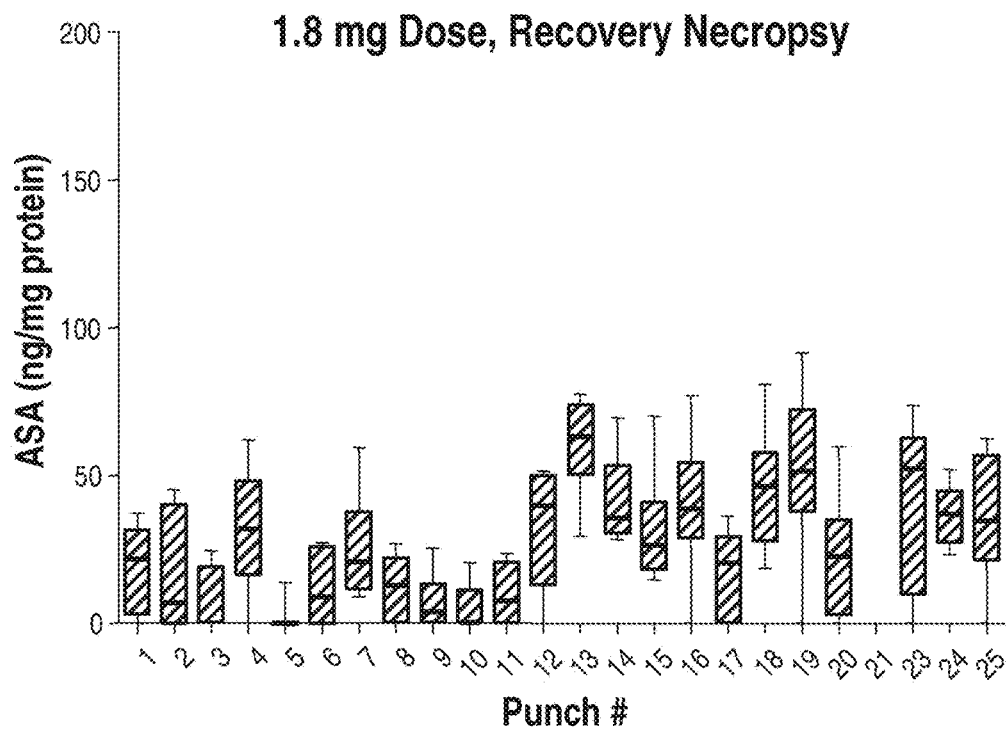
FIG. 29 illustrates exemplary concentration of rhASA in brain punches of juvenile cynomolgus monkeys following EOW IT dosing of rhASA at 1.8 mg/dose for 6-months—recovery necropsy

PET imaging data (FIG. 29) illustrates that both the ICV- and IT-administered $^{124}$I-labeled rhASA effectively distributed to the tissues of the CNS, and in particular the $^{124}$I-labeled rhASA administered through the IT-lumbar catheter immediately and uniformly spread in the cerebrospinal fluid (CSF) over the length of the spine. In particular, as depicted in FIG. 29, following ICV- and IT-administration, therapeutic concentrations of $^{124}$I-labeled rhASA were detected in the CNS tissues of the subject cynomolgus monkey, including the brain, spinal cord and CSF. The concentrations of rhASA detected in such CNS tissues, and in particular in the tissues of the brain, exceeded the therapeutic target concentration of 2.5 ng/mg of protein.

While the distribution of rhASA protein was comparable for both IT and ICV routes of administration, ICV resulted in notably less deposition within the spinal column, as evidence by FIG. 29.

Twenty four hours following administration of the formulation, both the ICV- and IT-administered $^{124}$I-labeled ASA effectively distributed to the tissues of the CNS. In particular, twenty four hours following IT-administration 12.4% of the administered dose was in the cranial region, compared to 16.7% of the ICV-administered dose. Accordingly, the concentrations of rhASA detected in such CNS tissues, and in particular in the tissues of the brain, when rhASA was administered IT approached those concentrations detected following ICV-administration of the same dose.

Figure 30:
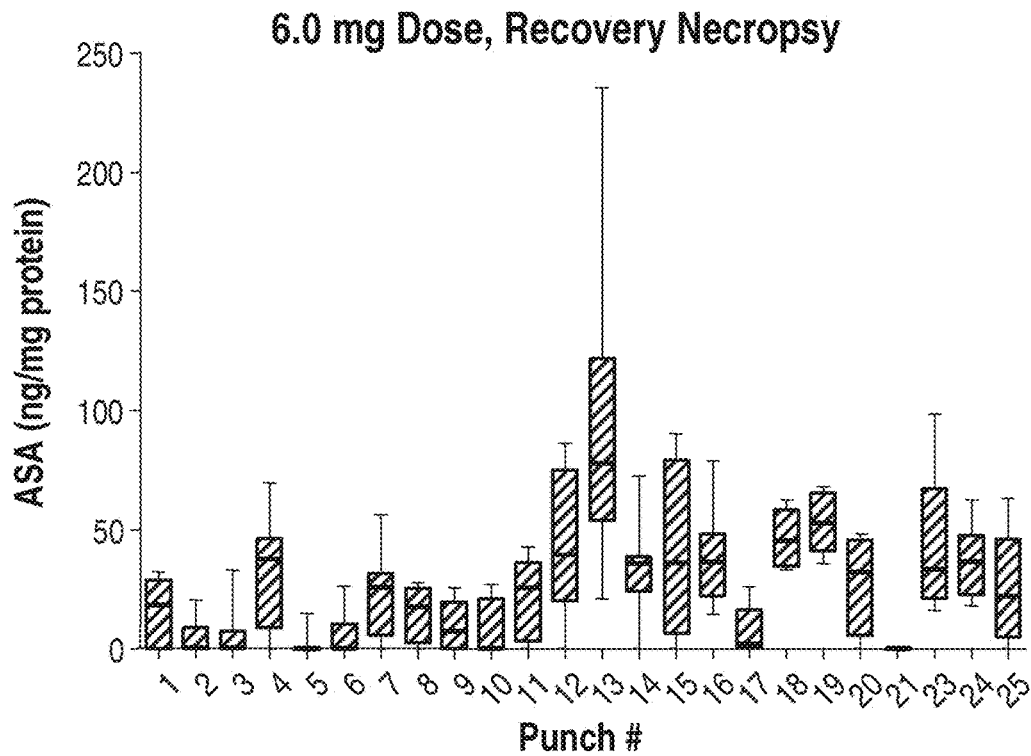
FIG. 30 illustrates exemplary concentration of rhASA in brain punches of juvenile cynomolgus monkeys following EOW IT dosing of rhASA at 6.0 mg/dose for 6 months—recovery necropsy
Figure 31:
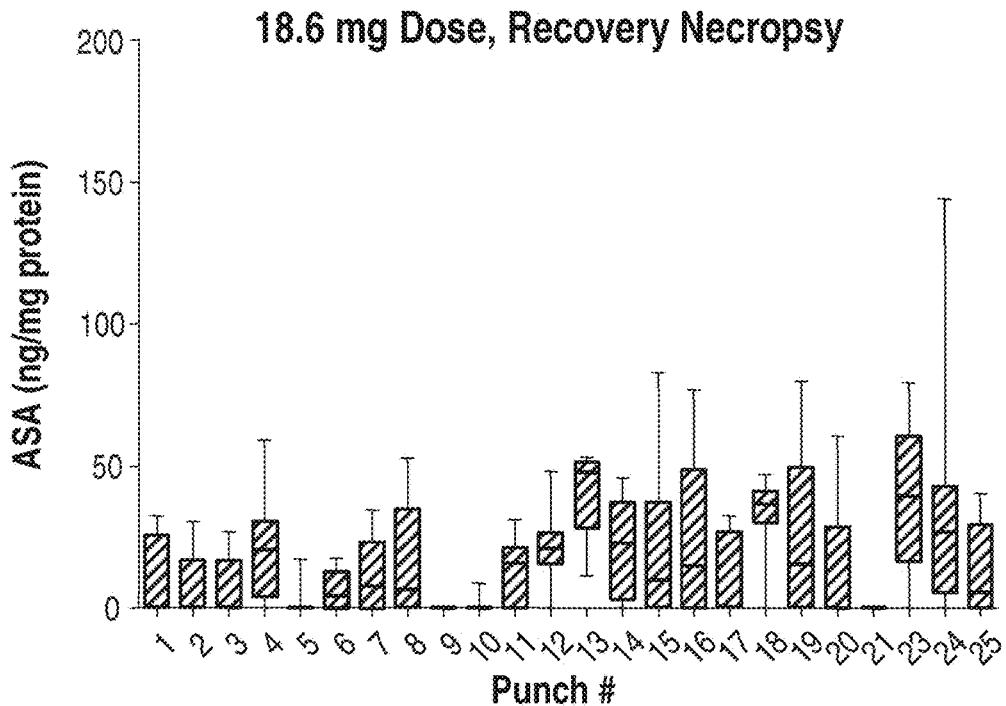
FIG. 31 illustrates exemplary concentration of rhASA in brain punches of juvenile cynomolgus following EOW IT dosing of rhASA at 18.6 mg/dose for 6-months—recovery necropsy

ICV injection of the $^{124}$I-labeled rhASA results ICV injection results in the immediate transfer of the injected volume to the cisterna magna, cisterna pontis, cisterna interpeduncularis and proximal spine, as illustrated in FIG. 30. As also illustrated in FIG. 30, within 2-5 hr IT administration delivered the $^{124}$I-labeled rhASA to the same initial compartments (cisternae and proximal spine) as shown for the ICV administration. Twenty four hours following both ICV- and IT-administration distribution of the $^{124}$I-labeled rhASA was comparable, as illustrated in FIG. 31. Accordingly, unlike small molecules drugs, the foregoing results suggest that ICV-administration offers minimal advantages over IT-administration of rhASA.

These results confirm that rhASA can be delivered to a subject using the less invasive IT route of administration and thereby achieve therapeutic concentrations in target cells and tissues.

The lysosomal storage diseases represent a family of genetic disorders caused by missing or defective enzymes which result in abnormal substrate accumulation. While the peripheral symptoms associated with several of these diseases can be effectively mitigated by intravenous administration of recombinant enzymes, intravenous administration of such recombinant enzymes are not expected to significantly impact the CNS manifestations associated with a majority of the lysosomal storage disease. For example, recombinant human iduronate-2-sulfatase (Idursulfase, Elaprase®; Shire Human Genetic Therapies, Inc. Lexington, Mass.) is approved for treatment of the somatic symptoms of Hunter syndrome but there is no pharmacologic therapy for the treatment of the neurologic manifestations which can include delayed development and progressive mental impairment. This is in part due to the nature of I2S, which is a large, highly-glycosylated enzyme with a molecular weight of approximately 76 kD and that does not traverse the blood brain barrier following intravenous administration.

The present inventors have therefore undertaken a program to investigate the intrathecal (IT) delivery of intrathecal formulations of recombinant human enzymes, such as, for example, iduronate-2-sulfatase (I2S), arylsulfatase A (rhASA) and alpha-N-acetylglucosaminidase (Naglu). The results presented herein represent the first to demonstrate that IT-lumbar administration of a recombinant lysosomal proteins result in the delivery of a significant fraction of the administered protein to the brain and in particular result in the widespread deposition of such proteins in neurons of the brain and spinal cord in both cynomolgus monkeys and dogs. Immunohistochemical analyses of the CNS tissues demonstrated that the protein is targeted to the lysosome, the site of pathologic glycosaminoglycan accumulation in the lysosomal storage disorders. Furthermore, the morphologic improvements demonstrated in the IKO mouse model of Hunter syndrome, the Naglu-deficient mouse model of Sanfilippo syndrome type B, and the ASA knockout mouse model of metachromatic leukodystrohpy (MLD) reinforces the observation that IT-administered enzyme is distributed to the appropriate tissues and transported to the appropriate cellular compartments and organelles.

The similarities observed in brain distribution patterns detected after IT-lumbar and ICV administration of I2S is suggestive of bulk flow and active remixing of the CSF. Thus in a clinical setting, both the IT and the ICV administration routes are potentially feasible, however, the observed deposition of I2S in the spinal cord following IT administration provides a clear advantage in addressing spinal sequelae and components of lysosomal storage diseases such as Hunter syndrome. Moreover, spinal injection ports are less invasive and expected to be more suitable for chronic use, especially in pediatric subjects.

Evidence from perivascular cell staining and protein translocation dynamics observed by the foregoing PET imaging studies indicate that enzyme moves within the perivascular space, presumably by pulsation-assisted convective mechanisms. An additional mechanism of transport is suggested by the observed association of I2S with neurofilaments, indicative of active axonal transport. The latter presumably begins with protein interaction with neuronal mannose-6-phosphate (M6P) receptors, which are widely expressed on cells of the spinal cord and brain and which upon direct administration to the brain parenchyma may cause I2S enzyme to be readily absorbed by target cells. (Begley, et al., Curr Pharm Des (2008) 14: 1566-1580).

While axonal transport of lysosomal enzymes have previously been implied by indirect methods in vivo and by imaging in vitro, the current studies provide the first direct evidence of axonal transport of non-virally or expressed enzymes delivered via the CSF. Thus, protein delivery from the CSF to the brain surface and deeper into the brain tissues seems to depend on active transfer processes, none of which have been previously described or elucidate for protein or enzyme delivery to the cells, tissues and organelles of the brain.

Contrary to the prevailing viewpoint that the flow dynamics of the parenchyma interstitium and CSF would prevent the distribution of IT-lumbar administered proteins to the white matter of the brain, the instant studies clearly demonstrate that IT delivery of a lysosomal enzyme results in protein distribution and accumulation in all brain tissues and deposition in the lysosomal compartment of target cells which are the site of pathologic glycosaminoglycan accumulation. (See, e.g., Fenstermacher et al., Ann N Y Acad Sci (1988) 531:29-39 and DiChiro et al., Neurology (1976) 26:1-8.) Together with the less invasive nature of IT-lumbar delivery, this route offers a clinically relevant means of delivering biologic therapeutics to the brain, particularly in children.

Example 3: Formulations of Arylsulfatase A for it Administration

This example summarizes the work to establish a high concentration liquid dosage form of rhASA (arylsulfase A) and the formulation of drug substance and drug product for treatment of Metachromatoc Leukodystrophy (MLD) via the intrathecal (IT) route of administration.

The stability data demonstrate that the saline formulation of drug substance and drug product (without PBS 20) is stable after 18 months at <−65 degrees C. and 18 months at 2-8 degrees C. During the pharmaceutical development of this protein, the solubility and stability of rhASA was investigated under limited buffer and excipient conditions due to its intended delivery to the CNS. Previously, formulation development studies had been conducted to develop an intravenous (IV) formulation. Based on the results of these experiments, a formulation containing 30 mg/ml of rhASA in 10 mM citrate-phosphate buffer, pH 5.5 with 137 mM NaCl and 0.15% poloxomer 188 was selected as the lead IV formulation. rhASA was also formulated for IT delivery in three formulations and stability data for this protein was investigated under these conditions. rhASA lots derived from upstream material product at one site were utilized. The results demonstrated that rhASA was stable in 154 mM sodium chloride solution with 0.005% polysorbate 20 (P20), pH 6.0 for at least 18 months at 2-8 degrees C. In addition, studies have been performed to demonstrate stability toward freeze-thaw and agitation-induced degradation.

Development lots were purified, ultrafiltered and diafiltered (UF/DF) into 10 mM citrate/phosphate, 137 mM NaCl, pH 5.5 with subsequent UF/DF into final saline solution at a concentration of approximately 40 mg/mL. The UF/DF operations are summarized in Table 7.

TABLE 7

Selected Formulations for UF/DF Operations from Xcellerex-Derived

| Formulation | Initial Buffer and UF/DF into Saline | Additive |
|---|---|---|
| A | 10 mM citrate/phosphate, 137 mM NaCl, pH 5.5. Subsequent UF/DF into 154 mM NaCl. Final pH 5.9 | 0.005% polysorbate 20* |
| B | 10 mM citrate/phosphate, 137 mM NaCl, pH 5.5. Subsequent UF/DF into 5 mM sodium phosphate, n145 mM NaCl, pH 6.0. Final pH 6.0 | 0.005% polysorbate 20* |
| C | 10 mM citrate/phosphate, 137 mM NaCl, pH 5.5. Subsequent UF/DF into 10 mM citrate/phosphate, 137 mM NaCl, pH 7.0, and a second UF/DF into 154 mM NaCl. Final pH 6.5 | 0.005% polysorbate 20* | rhASA rhASA formulated at 40 mg/mL rhASA in 10 mM citrate sodium phosphate with 137 mM NaCl, at pH 5.6 was dialyzed into five formulations which were utilized for IT preformulation studies (Table 8).

TABLE 8

Selected Buffers for IT Compatible Formulation Screening

| Formulation Number | Buffer Species | pH |
|---|---|---|
| 1 | 154 mM NaCl * | 5.9 |
| 2 | 154 mM NaCl ** | 7.0 |
| 3 | 5 mM phosphate buffer with 145 mM NaCl | 6.0 |
| 4 | 5 mM phosphate buffer with 145 mM NaCl | 7.0 |
| 5 | 1 mM phosphate buffer with 2 mM $CaCl_2$ and 137 mM NaCl | 7.0 |

Methods

For melting temperature (Tm) determination by Differential Scanning calorimetry (DSC), a capillary DSC microcalorimeter (MicroCal) was employed at a scan rate of 60° C./hr and a temperature range of 10-110° C. Buffer baselines were subtracted from the protein scans. The scans were normalized for the protein concentration of each sample (measured by ultraviolet absorbance at 280 nm and using an extinction coefficient of 0.69 (mg/mL)-1.cm-1). For initial short-term stability experiments, rhASA drug substance was subjected to either two weeks at 40° C. or one month at 40° C. Additional samples were placed on short term stability at 2-8° C. for 3 months. Samples were filtered (Millipore, P/N SLGV033RS) and aliquots of 0.5 mL were dispensed into 2 mL with 13 mm Flurotec stoppers.

Figure 5:
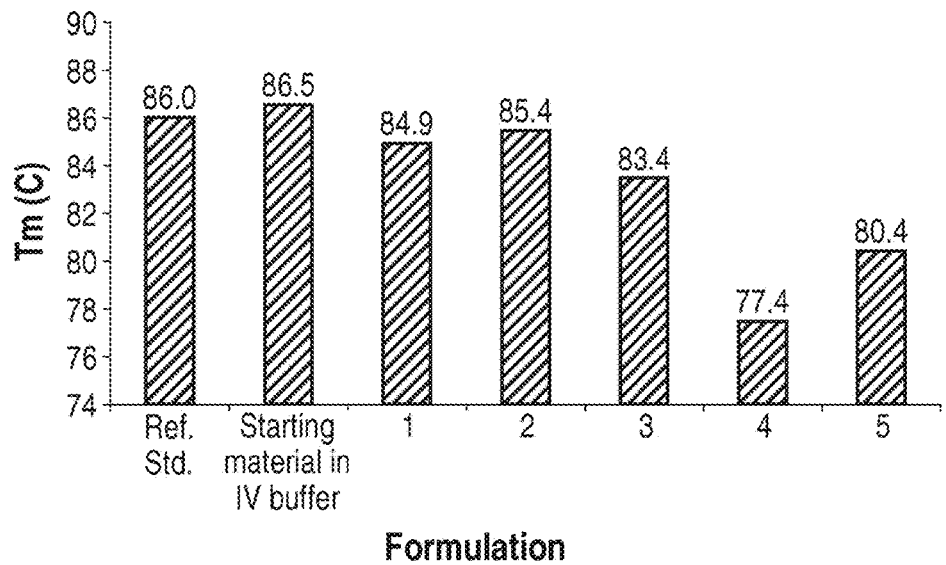
FIG. 5 illustrates exemplary analysis of the effect of buffer and pH on the thermal stability of rhASA.

The effect of formulation composition (Table 8) on the Tm (temperature midpoint of the thermally induces denaturation) was investigated using DSC. The Tm values for different formulation compositions are shown in FIG. 5. The Tm values exhibited similar unfolding temperatures for most of the formulations, except low Tm values were observed for rhASA formulated in either 5 mM sodium phosphate with 154 mM NaCl at pH 7.0 or 1 mM sodium phosphate with 2 mM $CaCl_2$ and 137 mM NaCl at pH 7.0.

Figure 6:
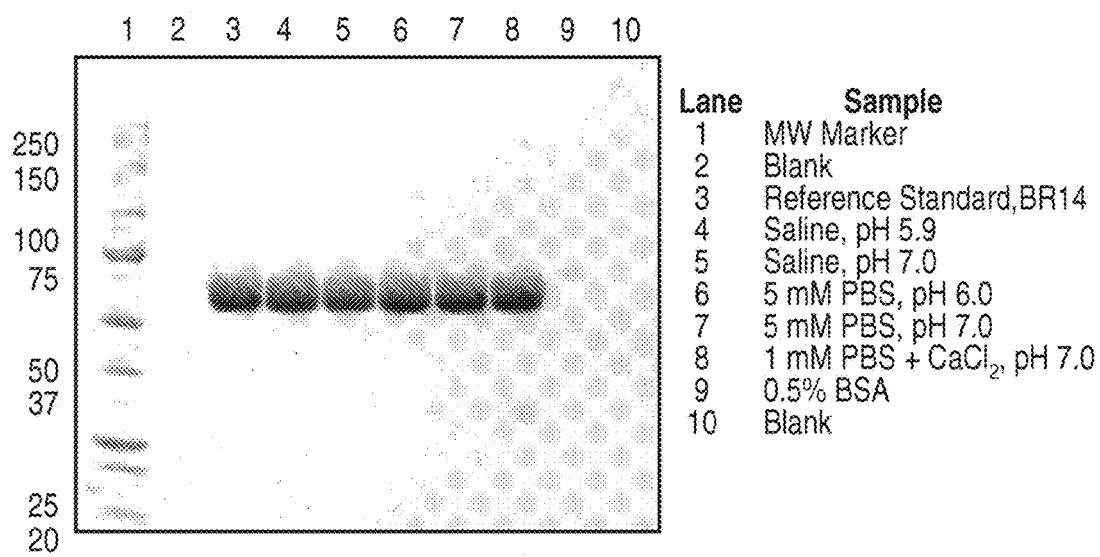
FIG. 6 illustrates exemplary SDS-PAGE (Coomassie) analysis of rhASA after two weeks at 40±2° C.

The effect of thermal induced degradation of rhASA in the five selected formulations (Table 8) was also investigated. Samples were stored either for 2 weeks or one month at 40° C. or for 3 months at 2-8° C. SDS-PAGE (Coomassie) analysis of samples stored for 2 weeks at 40° C. detected fragmentation of rhASA formulated in 5 mM sodium phosphate with 154 mM NaCl at pH 7.0 as well as in 1 mM sodium phosphate with 2 mM CaCl$_2$ and 137 mM NaCl at pH 7.0 (FIG. 6). No such degradation was observed for the other formulations.

The presence of breakdown products is consistent with the lower percent main peak observed by RP-HPLC for the same time points (Table 10). It was also observed that rhASA formulated in 1 mM PBS with 2 mM CaCl$_2$ at pH 7.0 did not maintain its pH at the onset and following the short term exposure to thermal stress conditions.

Waters HPLC systems were used for size exclusion and reversed phase HPLC analyses. For initial SEC-HPLC analysis, 50 μs of rhASA was injected on to an Agilent Zorbax GF-250 column (4.6 mm×250 mm) and run isocratically at 0.24 mL/min using a mobile phase of 100 mM sodium citrate pH 5.5 (octomer detection) with a detection wavelength of 280 nm. The analyses were repeated using mobile phase conditions of 100 mM sodium citrate, pH 7.0 (dimer detection).

All buffer exchange and concentration studies were performed using Centricon-Plus 20 (Millipore, 10 kDa MWCO).

Preformulation Screening Studies—Effect of Buffer Species and pH

Due to the limited number of approved solution compositions used for CNS administration, only five isotonic solution compositions, as listed in Table 8, were selected for screening.

pH Memory

Prior to the selection of buffers for long term stability, two "pH memory" experiments were performed to investigate if the protein buffer-exchanged into saline solution was capable of maintaining the pH of the original buffer. In the initial experiment, rhASA at approximately 8 mg/mL, was first dialyzed into 10 mM citrate-phosphate with 137 mM NaCl, at either a pH value of 5.5 or 7.0, followed by a second dialysis into saline solution. In the second experiment, rhASA was dialyzed into 10 mM citrate-phosphate with 137 mM NaCl, at either pH values of 5.5 or 7.0 and subsequently buffer exchanged and concentrated into saline solutions to approximately 35 mg/mL.

When rhASA formulated in 10 mM citrate-phosphate with 137 mM NaCl at either pH values of 5.5 or 7.0 was dialyzed into saline solution, no increased turbidity was observed. The pH of the final saline solution was similar to the pH of the previous citrate-phosphate buffer to which it was exposed. When rhASA formulated in citrate-phosphate based buffers at either pH values of 5.5 or pH 7.0 were dialyzed into saline and then concentrated to approximately 35 mg/mL using a Centricon, the pH of the protein saline solutions shifted from pH 5.5 to 5.8 or from pH 7.0 to 6.8, respectively. Both concentrated rhASA solutions in saline were slightly opalescent and had OD320 values in the range of 0.064 (pH 6.8) to 0.080 (pH 5.5).

Excipient Selection

Polysorbate 20 (P20) was included in all five selected solution compositions at a final concentration of 0.005%. The surfactant choice was made based on prior experience of the in vivo tolerability of P20 at 0.005% for CNS delivery of other Shire proteins. A solution of 5% P20 (v/v) was prepared and the appropriate volume was added to each protein formulation to obtain a final concentration of 0.005%.

Formulation Robustness Studies—Stability Study

Based on the initial results obtained from screening of different buffers and pH values, three solution compositions were selected for long term stability studies (sample preparation as in Table 8. A one year study was initiated in the proposed formulations (Table 9). The stability samples at each time point were analyzed by SEC-HPLC, RP-HPLC, OD320, protein concentration, pH, specific activity, SDS-PAGE (Coomassie), and appearance.

TABLE 9

Formulations for Long Term Stability Studies

| Formulation | Formulation Composition with 0.005% Polysorbate 20 | Study Conditions |
|---|---|---|
| A | 154 mM NaCl, pH 5.9 | 5° C., 25° C., |
| B | 5 mM sodium phosphate, 145 mM NaCl, pH 6.0 | 40° C., and frozen baseline |
| C | 154 mM NaCl, pH 6.5 | at ≤−65° C. |

TABLE 10

STABILITY OF SELECTED FORMULATIONS AFTER 2 WEEKS AT 40 ± 2° C.

| Formulation | Appearance | Protein Conc. (mg/mL) | OD320 | SEC-HPLC (% main peak) at pH 5.5 | SEC-HPLC (% main peak) at pH 7.0 | RP-HPLC (% main peak) | pH | Specific Activity (U/mg) |
|---|---|---|---|---|---|---|---|---|
| Saline, pH 5.9 | | | | | | | | |
| Baseline | Clear to slightly opalescent | 29.9 | 0.044 | >99.9 | 99.7 | 99.8 | 5.6 | 74 |
| Stressed | Clear to slightly opalescent | 31.1 | 0.062 | 99.8 | 99.6 | 99.9 | 5.7 | 88 |
| Saline, pH 7.0 | | | | | | | | |
| Baseline | Clear to slightly opalescent | 29.0 | 0.038 | >99.9 | 99.6 | >99.9 | 6.7 | 83 |
| Stressed | Clear to slightly opalescent | 32.1 | 0.041 | 99.1 | 99.7 | 97.0 | 6.5 | 66 |
| 5 mM PBS, pH 6.0 | | | | | | | | |
| Baseline | Clear to slightly opalescent | 29.8 | 0.058 | >99.9 | 99.7 | 99.9 | 5.9 | 102 |

TABLE 10-continued

STABILITY OF SELECTED FORMULATIONS AFTER 2 WEEKS AT 40 ± 2° C.

| Formulation | Appearance | Protein Conc. (mg/mL) | OD320 | SEC-HPLC (% main peak) at pH 5.5 | SEC-HPLC (% main peak) at pH 7.0 | RP-HPLC (% main peak) | pH | Specific Activity (U/mg) |
|---|---|---|---|---|---|---|---|---|
| Stressed | Clear to slightly opalescent | 30.5 | 0.076 | 98.8 | 99.7 | 99.7 | 5.9 | 95 |
| | | | 5 mM PBS, pH 7.0 | | | | | |
| Baseline | Clear to slightly opalescent | 29.7 | 0.035 | >99.9 | 99.7 | >99.7 | 6.9 | 86 |
| Stressed | Slightly opalescent to opalescent | 30.5 | 0.041 | 95.4 | 99.4 | 98.0 | 6.8 | 94 |
| | | | 1 mM PBS, pH 7.0 with 2 mM CaCl₂, pH 7.0 | | | | | |
| Baseline | Clear to slightly opalescent | 27.5 | 0.040 | >99.9 | 99.7 | >99.9 | 5.6 | 90 |
| Stressed | Slightly opalescent to opalescent | 27.7 | 0.042 | 94.8 | 99.8 | 99.0 | 6.6 | 93 |

No significant change in specific activity was observed for the stress samples (Table 10). Analysis by size exclusion HPLC detected some degradation for the 2 week thermal stressed sample formulated in 5 mM sodium phosphate with 154 mM NaCl at pH 7.0. The degradation was more evident by SEC-HPLC using a pH 5.5 mobile phase condition which induces association of rhASA to an octamer. Under these mobile phase conditions, rhASA formulated at pH 7.0 in 1 mM PBS with 2 mM CaCl₂ also exhibited significant degradation.

Following exposure to 1 month at 40° C., samples formulated in 5 mM PBS, pH 7.0 and 1 mM PBS, pH 7.0 with 2 mM CaCl₂ demonstrated fragmentation by SDS-PAGE (data not shown). Consistent with this observation, a reduction in the percent main peak was also observed by RP-HPLC and SEC-HPLC for samples stored in these two pH 7 formulations (Table 11). A decrease in specific activity, however, was only observed for rhASA formulated in 5 mM PBS, pH 7.0.

TABLE 11

Stability of Selected IT Formulations after 1 Month at 40 ± 2° C.

| Formulation | Appearance | Protein Conc. (mg/mL) | OD320 | SEC-HPLC (% main peak) at pH 5.5 | SEC-HPLC (% main peak) at pH 7.0 | RP-HPLC (% main peak) | pH | Specific Activity (U/mg) |
|---|---|---|---|---|---|---|---|---|
| | | | Saline, pH 5.9 | | | | | |
| Baseline | Clear to slightly opalescent | 29.9 | 0.044 | >99.9 | 99.7 | 99.8 | 5.6 | 74 |
| Stressed | Clear to slightly opalescent | 28.3 | 0.061 | >99.9 | 99.5 | 99.9 | 5.7 | 107 |
| | | | Saline, pH 7.0 | | | | | |
| Baseline | Clear to slightly opalescent | 29.0 | 0.038 | >99.9 | 99.6 | >99.9 | 6.7 | 83 |
| Stressed | Clear to slightly opalescent | 25.7 | 0.189 | 95.7 | 99.8 | 99.5 | 6.6 | 100 |
| | | | 5 mM PBS, pH 6.0 | | | | | |
| Baseline | Clear to slightly opalescent | 29.8 | 0.058 | >99.9 | 99.7 | 99.9 | 5.9 | 102 |
| Stressed | Clear to slightly opalescent | 28.0 | 0.059 | >99.9 | 99.6 | 99.9 | 6.0 | 94 |
| | | | 5 mM PBS, pH 7.0 | | | | | |
| Baseline | Clear to slightly opalescent | 29.7 | 0.035 | >99.9 | 99.7 | >99.9 | 6.9 | 86 |

TABLE 11-continued

Stability of Selected IT Formulations after 1 Month at 40 ± 2° C.

| Formulation | Appearance | Protein Conc. (mg/mL) | OD320 | SEC-HPLC (% main peak) at pH 5.5 | SEC-HPLC (% main peak) at pH 7.0 | RP-HPLC (% main peak) | pH | Specific Activity (U/mg) |
|---|---|---|---|---|---|---|---|---|
| Stressed | Slightly opalescent to opalescent | 27.3 | 0.142 | 91.8 | 89.6 | 97.1 | 6.9 | 48 |
| 1 mM PBS, pH 7.0 with 2 mM CaCl₂ | | | | | | | | |
| Baseline | Clear to slightly opalescent | 27.5 | 0.040 | >99.9 | 99.7 | >99.9 | 5.6 | 90 |
| Stressed | Slightly opalescent to opalescent | 28.3 | 0.053 | 90.6 | 88.7 | 97.9 | 6.7 | 133 |

After 3 months storage at 2-8° C., rhASA retained its activity in all formulations (Table 12). Additionally, rhASA maintained >99.8% of its main peak area as assessed by SEC-HPLC under both mobile phase conditions. The stability data for 3 months at 2-8° C. are summarized in Table 12.

TABLE 12

STABILITY OF SELECTED IT BUFFERS AFTER 3 MONTH AT 2-8° C.

| Formulation | Appearance | Protein Conc. (mg/mL) | OD320 | SEC-HPLC (% main peak) at pH 5.5 | SEC-HPLC (% main peak) at pH 7.0 | RP-HPLC (% main peak) | pH | Specific Activity (U/mg) |
|---|---|---|---|---|---|---|---|---|
| Saline, pH 5.9 | | | | | | | | |
| Baseline | Clear to slightly opalescent | 29.9 | 0.044 | >99.9 | 99.7 | 99.8 | 5.6 | 74 |
| Stressed | Clear to slightly opalescent | 29.4 | 0.056 | 99.8 | >99.9 | 99.9 | 5.6 | 97 |
| Saline, pH 7.0 | | | | | | | | |
| Baseline | Clear to slightly opalescent | 29.0 | 0.038 | >99.9 | 99.6 | >99.9 | 6.7 | 83 |
| Stressed | Clear to slightly opalescent | 25.5 | 0.040 | 99.8 | >99.9 | >99.9 | 6.6 | 127 |
| 5 mM PBS, pH 6.0 | | | | | | | | |
| Baseline | Clear to slightly opalescent | 29.8 | 0.058 | >99.9 | 99.7 | 99.9 | 5.9 | 102 |
| Stressed | Clear to slightly opalescent | 29.9 | 0.045 | 99.8 | >99.9 | >99.9 | 5.9 | 109 |
| 5 mM PBS, pH 7.0 | | | | | | | | |
| Baseline | Clear to slightly opalescent | 29.7 | 0.035 | >99.9 | 99.7 | >99.9 | 6.9 | 86 |
| Stressed | Clear to slightly opalescent | 29.0 | 0.038 | 99.8 | >99.9 | >99.9 | 6.9 | 110 |
| 1 mM PBS, pH 7.0 with 2 mM CaCl₂ | | | | | | | | |
| Baseline | Clear to slightly opalescent | 27.5 | 0.040 | >99.9 | 99.7 | ?99.9 | 5.6 | 90 |
| Stressed | Clear to slightly opalescent | 28.0 | 0.042 | 99.8 | 99.9 | >99.9 | 6.6 | 105 |

Figure 7:
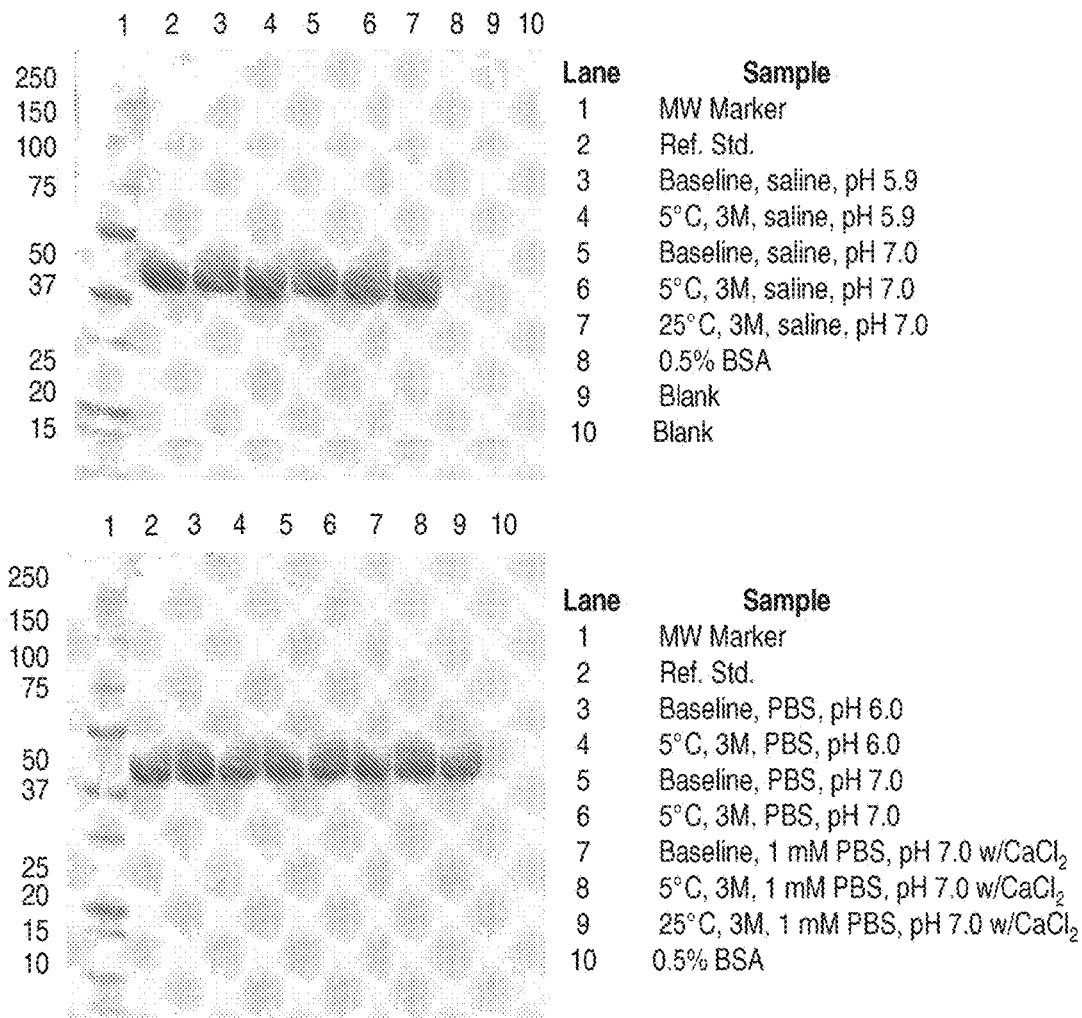
FIG. 7 illustrates exemplary SDS-PAGE (Coomassie) analysis of rhASA in IT formulations after 3 months at 5 and 25° C.

RhASA formulated in saline, pH 7.0 and 1 mM PBS, pH 7.0 with 2 mM $CaCl_2$ were also evaluated after 3 months storage at the accelerated condition of 25° C. As shown in FIG. 7, rhASA undergoes a slight amount of fragmentation in these formulations (with intensity approximately that of the 0.5% BSA impurity spike).

Collectively, the preformulation studies demonstrated that the stability of rhASA is maintained at pH values in the range of 5.5 to 6.0. In all studies using formulation solutions at pH 7.0, rhASA demonstrated fragmentation as one of its degradation pathways. The thermal stress results obtained for the IT formulation candidates at pH 7.0 were similar to the thermal stress results obtained for the IV formulations (10 mM sodium citrate-phosphate with 137 mM NaCl) at pH 7.0, where fragmentation was also observed. Based on these studies, three following formulations, as in Table 9, were selected for long term stability studies.

Freeze-Thaw Studies

Freeze-thaw experiments were conducted by performing three cycles of controlled freeze-thaw, from ambient to −50° C. at 0.1° C./min on the shelves of a Vertis Genesis 35EL lyophilizer. One mL aliquots of drug substance formulated at 30 mg/mL in each of the five solution compositions (Table 8) were dispensed into 3 mL glass vials for this study.

Drug substance (38±4 mg/mL) was used for all freeze-thaw studies. For small scale controlled rate freeze-thaw experiments, 2 mL aliquots of drug substance were dispensed into 5 mL glass vials with 20 mm Flurotec stoppers. Freeze-thaw stress experiments were conducted either on the shelves of a Virtis Genesis 35EL lyophilizer or on the shelves of a controlled rate freezer (Tenney Jr Upright Test Chamber, Model: TUJR-A-VERV). Three cycles of freezing to −50° C. and thawing to 25° C. were performed at either a freeze and thaw rate of 0.1° C./min (using a controlled rate freezer) or a freeze rate of 0.1° C./min and thaw rate of 0.03° C./min (using lyophilizer). For bulk freeze-thaw studies, 90 mL of drug substance was dispensed into 250 mL polycarbonate bottles. For freeze-thaw studies on dry ice, 3 mL of drug substance was dispensed into 5 mL polycarbonate (Biotainer P/N 3500-05) vials with and without polypropylene screwcaps. The samples were frozen overnight at ≤−65° C. and then placed on dry ice in a closed bucket. For these experiments, stoppered glass vials containing the same sample volume were used as a study control. For freeze-thaw studies of the diluted drug substance, 1 mL aliquots of 1 and 5 mg/mL were dispensed into 2 mL polypropylene tubes and were frozen at ≤−65° C. The frozen samples were subsequently thawed on the bench top. The cycle was repeated up to 10 times to mimic any potential stress which may occur with handling of the reference standard aliquots.

The effect of freeze-thaw on the quality of rhASA in the proposed formulations with 0.005% P20 was determined after 3 cycles of controlled rate freezing and thawing (0.1° C./min). No change in the appearance of rhASA was observed and no soluble aggregates or degradants were identified using either SEC or RP-HPLC methods. Additionally, no fragmentation or aggregation bands were observed in the reduced SDS-PAGE analysis (data not shown). Table 13 summarizes the results of these studies.

TABLE 13

Effect of Small Scale Freeze-Thaw on the Quality of rhASA Drug Substance

| Formulation | Appearance | Protein Conc. (mg/mL) | SEC-HPLC (% main peak) at pH 5.5 | SEC-HPLC (% main peak) at pH 7.0 | RP-HPLC (% main peak) | pH | Specific Activity (U/mg) |
|---|---|---|---|---|---|---|---|
| Saline, pH 5.9 | | | | | | | |
| Baseline | Clear to slightly opalescent | 29.9 | NT* | NT | NT | 5.6 | 102 |
| Stressed | Clear to slightly opalescent | 29.4 | >99.9 | 99.6 | 99.4 | 5.5 | 86 |
| Saline, pH 7.0 | | | | | | | |
| Baseline | Clear to slightly opalescent | 29.0 | NT | NT | NT | 6.7 | 94 |
| Stressed | Clear to slightly opalescent | 25.0 | >99.9 | 99.6 | 99.2 | 6.6 | 96 |
| 5 mM PBS, pH 6.0 | | | | | | | |
| Baseline | Clear to slightly opalescent | 29.8 | NT | NT | NT | 5.9 | 92 |
| Stressed | Clear to slightly opalescent | 31.1 | >99.9 | 99.7 | 99.5 | 5.9 | 95 |
| 5 mM PBS, pH 7.0 | | | | | | | |
| Baseline | Clear to slightly opalescent | 29.7 | NT | NT | NT | 6.9 | 99 |
| Stressed | Clear to slightly opalescent | 29.9 | >99.9 | 99.6 | 99.0 | 6.9 | 112 |

TABLE 13-continued

Effect of Small Scale Freeze-Thaw on the Quality of rhASA Drug Substance

| Formulation | Appearance | Protein Conc. (mg/mL) | SEC-HPLC (% main peak) at pH 5.5 | SEC-HPLC (% main peak) at pH 7.0 | RP-HPLC (% main peak) | pH | Specific Activity (U/mg) |
|---|---|---|---|---|---|---|---|
| 1 mM PBS, pH 7.0 with 2 mM CaCl$_2$ | | | | | | | |
| Baseline | Clear to slightly opalescent | 27.5 | NT | NT | NT | 5.6 | 90 |
| Stressed | Clear to slightly opalescent | 27.3 | >99.9 | 99.6 | 99.3 | 6.7 | 103 |

*Not tested

The results of the small scale controlled rate freeze-thaw studies performed in triplicate on 2 mL aliquots of drug substance are summarized in Table 14. No change in the quality of the drug substance was observed. The appearance of the frozen and thawed drug substance was comparable to the appearance of the baseline sample. No reduction in protein concentration or the purity of material was observed.

TABLE 14

EFFECT OF SMALL SCALE FREEZE-THAW ON THE QUALITY OF RHASA DRUG SUBSTANCE

| Freeze/Thaw Rate | Baseline | 0.1° C./min Freeze- 0.1° C./min Thaw Using Controlled Rate Freezer | 0.1° C./min Freeze- 0.03° C./min Thaw Using Lyophilizer |
|---|---|---|---|
| Appearance | Slightly opalescent to opalescent | Slightly opalescent to opalescent | Slightly opalescent to opalescent |
| Protein Conc. (mg/mL) | 42 | 37 | 36 |
| Optical Density at 320 nm | 0.044 | 0.045 | 0.043 |
| SEC-HPLC (% main peak) | 99.6% | 99.7% | 99.7% |
| RP-HPLC (% main peak) | >99.9% | >99.9% | >99.9% |
| pH | 5.9 | 5.9 | 5.9 |
| Specific Activity (U/mg) | 65 | 69 | 71 |

All experiments demonstrated that rhASA maintains its quality attributes after freeze-thaw. It should be noted that a small decreasing trend was observed in the activity and the reversed phase percent main peak for 1 mg/mL rhASA samples after ten cycles of freeze-thaw as shown in Table 15.

TABLE 15

EFFECT OF SMALL SCALE FREEZE-THAW ON RHASA DRUG SUBSTANCE DILUTED TO 1 MG/ML

| Sample | Baseline | 1 F/T cycle | 3 F/T cycles | 5 F/T cycles | 10 F/T cycles |
|---|---|---|---|---|---|
| Protein Conc. (mg/mL) | 1.0 | 1.0 | 1.0 | 1.0 | 1.0 |
| Optical Density at 320 nm | 0.013 | 0.005 | 0.010 | 0.006 | 0.017 |
| SEC-HPLC (% main peak) | 99.5% | 99.5% | 99.5% | 99.5% | 99.6% |
| RP-HPLC (% main peak) | 99.2% | 99.2% | 99.1% | 99.0% | 98.9% |
| pH | 5.8 | 5.8 | 5.8 | 5.8 | 5.8 |
| Specific Activity (U/mg) | 78 | 76 | 75 | 69 | 65 |

Agitation Studies

Aliquots of 1.0 mL of sterile filtered protein formulated at 30 mg/mL in each of five selected solution compositions (Table 8) with P20 were dispensed into 3 mL glass vials with 13 mm Flurotec stoppers. Vials were placed on their side on a Labline Orbital Shaker and shaken for 24 hours at 100 rpm. The setting was then increased to 200 rpm for the next 24 hours of shaking period.

In order to assess the susceptibility of rhASA to agitation, shaking and stirring studies were performed for both drug substance and drug product at concentrations of 35.4 and 30 mg/mL, respectively. For these studies, 1.0 mL aliquots of drug substance were dispensed into 3 mL glass vials with 13 mm Flurotec stopper. The agitated vials were inspected every other hour for the first 8 hours and thereafter at 24 and 48 hours. The vials were removed at the first sign of cloudiness and analyzed. The appearance of samples was documented and the samples were assayed using pH, SEC-HPLC, specific activity, and OD320. Drug product agitation studies were conducted in triplicate (in 154 mM NaCl, pH 6.0 with 0.005% P20) and compared with one replicate of drug substance (in 154 mM NaCl, pH 6.0). Shaking studies were also repeated without inclusion of P20 in saline formulation. For these studies, either 1 mL or 3 mL aliquots of drug product at 30 mg/mL were dispensed into 3 mL vials to investigate the effect of shaking as well as the headspace volume on quality of rhASA. For these shaking studies, a speed of 220 rpm was used.

Initial shaking studies of rhASA for IV formulation development studies performed demonstrated the potential advantage for the presence of a surfactant. For IT formulation development, 0.005% P20 was selected and included in formulations for the shaking studies. After 15-24 hours of shaking at 100 rpm, no visual changes were observed for any of the formulations and the shaking speed was increased to 200 rpm. No change in the appearance of the shaken samples in the proposed candidate formulations was observed after a total of 48 hours of shaking at 100 and 200 rpm. The samples were analyzed after this period and the results are summarized in Table 16. No changes were observed by any of the assays. SDS-PAGE Coomassie also exhibited no additional high or low molecular weight bands for the shaken samples (data not shown).

TABLE 16

RESULTS OF SHAKING STUDIES OF SELECTED IT FORMULATIONS

| Formulation | Appearance | Protein Conc. (mg/mL) | OD320 | SEC-HPLC (% main peak) at pH 5.5* | RP-HPLC (% main peak) | Specific Activity (U/mg) |
|---|---|---|---|---|---|---|
| Saline, pH 5.9 | | | | | | |
| Baseline | Clear to slightly opalescent | 29.9 | 0.044 | NT** | NT | 111 |
| Stressed | Clear to slightly opalescent | 28.5 | 0.041 | >99.9 | 99.9 | 111 |
| Saline, pH 7.0 | | | | | | |
| Baseline | Clear to slightly opalescent | 29.0 | 0.038 | NT | NT | 115 |
| Stressed | Clear to slightly opalescent | 24.7 | 0.032 | >99.9 | >99.9 | 110 |
| 5 mM PBS, pH 6.0 | | | | | | |
| Baseline | Clear to slightly opalescent | 29.8 | 0.058 | NT | NT | 103 |
| Stressed | Clear to slightly opalescent | 30.4 | 0.047 | >99.9 | 99.9 | 116 |
| 5 mM PBS, pH 7.0 | | | | | | |
| Stressed | Clear to slightly opalescent | 29.7 | 0.035 | NT | NT | 92 |
| Baseline | Clear to slightly opalescent | 26.5 | 0.029 | >99.9 | 99.9 | 110 |
| 1 mM PBS, pH 7.0 with 2 mM CaCl$_2$ | | | | | | |
| Baseline | Clear to slightly opalescent | 27.5 | 0.040 | NT | NT | 147 |
| Stressed | Clear to slightly opalescent | 27.0 | 0.038 | >99.9 | 99.9 | 107 |

Figure 8A:
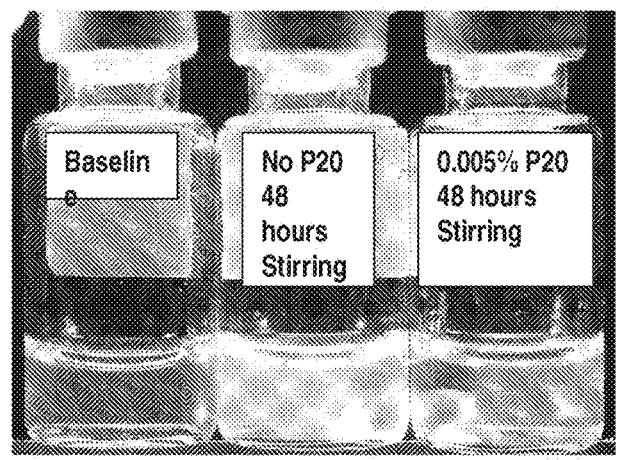
FIG. 8 depicts exemplary rhASA drug substance and drug product appearance after 48 hours of stirring (Panel A) and shaking (Panel B).
Figure 8B:
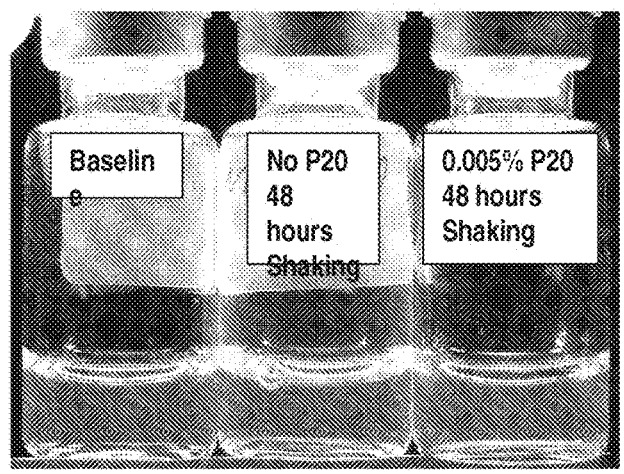

*Due to column problems the SEC profile of dimeric form, at mobile phase pH of 7.0, was not obtained.
**Not tested No change in the appearance of drug substance (in 154 mM NaCl at pH 6.0) or drug product (in 154 mM NaCl, pH 6.0, with 0.005% P20) was observed for the first 4 hours of stirring. After 6 hours of stirring, both drug substance and drug product became slightly cloudy (data not shown). The cloudiness was more pronounced after 48 hours of stirring when no P20 was present in the formulation. Additionally, drug substance and drug product exposed to shaking became cloudy after 24 hours. FIG. 8 demonstrates the agitation observations after 48 hours.

Table 17 and Table 18 summarize the agitation study observations.

TABLE 17

APPEARANCE OF RHASA DRUG SUBSTANCE AND DRUG PRODUCT (WITH P20) AFTER STIRRING

| Hours | Stirred Drug Substance | Stirred Drug Product |
|---|---|---|
| Baseline | Colorless, opalescent, free of particles | Colorless, opalescent, free of particles |
| 2 | No Change | No Change |

TABLE 17-continued

APPEARANCE OF RHASA DRUG SUBSTANCE AND DRUG PRODUCT (WITH P20) AFTER STIRRING

| Hours | Stirred Drug Substance | Stirred Drug Product |
|---|---|---|
| 4 | No Change | No Change |
| 6 | 1-2 flakes, slightly cloudy | Fibrous material, slightly cloudy |
| 8 | 1-2 flakes, slightly cloudy | Fibrous material, slightly cloudy |
| 24 | 1-2 flakes, very cloudy | Fibrous material, cloudy |
| 48 | 1-2 flakes, very cloudy | Fibrous material, very cloudy |

TABLE 18

APPEARANCE OF RHASA DRUG SUBSTANCE AND
DRUG PRODUCT (WITH P20) AFTER SHAKING

| Hours | Shaken Drug Substance | Shaken Drug Product |
|---|---|---|
| Baseline | Colorless, opalescent, free of particles | Colorless, opalescent, free of particles |
| 2 | No Change | No Change |
| 4 | No Change | No Change |
| 6 | No Change | No Change |
| 8 | No Change | No Change |
| 24 | 1-2 flakes | 1-2 fibers |
| 48 | Fibrous material | 1-2 fibers |

The agitated samples were also analyzed by OD320, pH, specific activity, RP-HPLC, and SEC-HPLC. The results are presented in Table 19 and Table 20. Overall, no significant change was observed in the quality of rhASA after stirring and shaking, with the exception of the appearance.

TABLE 19

EFFECT OF 48 HOURS OF SHAKING ON DRUG SUBSTANCE
AND DRUG PRODUCT

| Freeze/Thaw Rate | Baseline | Shaken Drug Substance for 48 hrs (n = 1) | Shaken Drug Product for 48 hrs (n = 3) |
|---|---|---|---|
| Optical Density at 320 nm | 0.080 | 0.053 | 0.048 |
| SEC-HPLC (% main peak) | 99.7% | 99.7% | 99.7% |
| RP-HPLC (% main peak) | >99.9% | >99.9% | >99.9% |
| pH | 6.0 | 6.0 | 5.9 |
| Specific Activity (U/mg) | 96 | 71 | 72 |

Upon stirring drug product after 6 hours, with 0.005% P20, one of the three replicate became turbid. This sample was removed and the other two samples were stirred up to 48 hours. Table 20 demonstrates the averaged data for duplicate samples.

TABLE 20

EFFECT OF 48 HOURS OF STIRRING ON DRUG SUBSTANCE
AND DRUG PRODUCT

| Freeze/Thaw Rate | Baseline | Stirred Drug Substance for 6 hrs (n = 1) | Stirred Drug Product for 48 hrs (n = 2) |
|---|---|---|---|
| Optical Density at 320 nm | 0.080 | 0.244 | 0.103 |
| SEC-HPLC (% main peak) | 99.7% | 99.7% | 99.7% |
| RP-HPLC (% main peak) | >99.9% | >99.9% | >99.9% |
| pH | 6.0 | 6.0 | 6.0 |
| Specific Activity (U/mg) | 69 | 73 | 73 |

Based on the results and the visual observations, drug substance and drug product are not readily susceptible to agitation-induced degradation since it took ~4 hours of continuous stirring (at setting number 5) and 8 hours of continuous vigorous shaking (at 220 rpm) for a change in appearance to occur.

Figure 9:
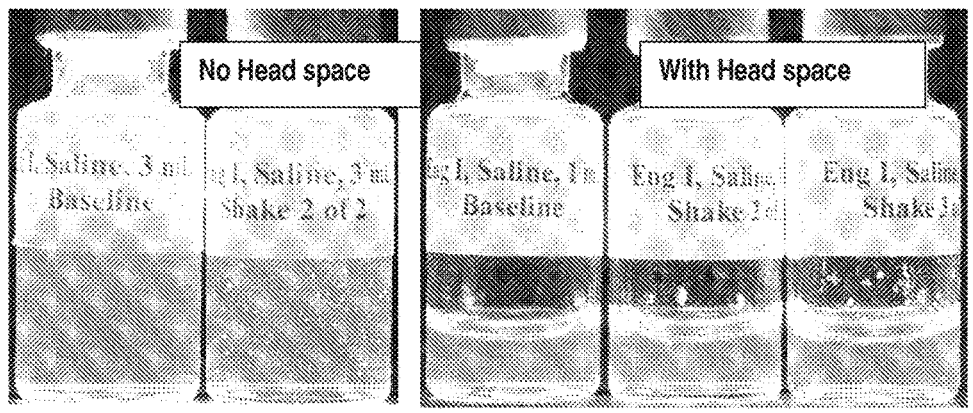
FIG. 9 depicts exemplary rhASA drug product appearance (w/o P20) with (n=2) and without headspace (n=1) after stirring for 48 hours.

The shaking studies were repeated with drug product in the absence of P20. For these studies, each vial was filled with either 1 mL or 3 mL of drug product in order to investigate the effect of shaking as well as the headspace volume on the quality of rhASA. For 1 mL fill in 3 mL vials, no change in the appearance of drug product was observed through 8 hours of shaking at 220 rpm (n=2, data not shown). Vials with no headspace (n=1) demonstrated the formation of small flakes, a few fibers and flocculent matter at a faster rate when compared to the vials with a larger headspace. The 48 hour observations are presented in FIG. 9.

The visual results are also summarized in Table 21 and Table 22.

TABLE 21

APPEARANCE OF DRUG PRODUCT IN THE ABSENCE OF
POLYSORBATE 20 AFTER 48 HOURS OF SHAKING WITH
1 ML FILL IN 3 ML VIAL

| Hours | Shaken Drug Product MLD-200L-001 without P20 | Shaken Drug Product MLD-200L-003 without P20 | Control_Shaken Drug Product MLD-200L-001 with P20 |
|---|---|---|---|
| Baseline | Colorless, slightly opalescent, essentially free of particles | | |
| 2 | No Change | No Change | No Change |
| 4 | No Change | No Change | No Change |
| 6 | No Change | No Change | No Change |
| 8 | No Change | No Change | No Change |
| 24 | Flocculent | Significant flocculent | No Change |
| 48 | Flocculent | Significant flocculent | No Change |

TABLE 22

APPEARANCE OF DRUG PRODUCT IN THE ABSENCE OF
POLYSORBATE 20 AFTER 48 HOURS OF SHAKING WITH
3 ML FILL IN 3 ML VIAL

| Hours | Shaken Drug Product MLD-200L-001 without P20 | Control_Shaken Drug Product MLD-200L-001 with P20 |
|---|---|---|
| Baseline | Colorless, slightly opalescent, essentially free of particles | |
| 2 | No Change | No Change |
| 4 | Small flakes, few fibers and flocculent | No Change |
| 6 | Small flakes, few fibers and flocculent | No Change |
| 8 | Small flakes, few fibers and flocculent | No Change |
| 24 | Small flakes, few fibers and flocculent | No Change |
| 48 | Small flakes, few fibers and flocculent | No Change |

No change in the protein concentration was observed. Additionally, no soluble aggregates were detected using SEC-HPLC for either the 1 mL or 3 mL fill volumes (Table 23 and Table 24). Reduced SDS-PAGE (Coomassie) assay did not detect any high or low molecular weight bands (data not shown).

TABLE 23

RESULTS OF 48 HOURS OF SHAKING ON DRUG
PRODUCT IN THE ABSENCE OF
POLYSORBATE 20 WITH 1 ML FILL IN 3 ML VIAL

| Assay | Baseline | Shaken Drug Product after 24 hrs (n = 2) without P20 | Shaken Drug Product after 48 hrs (n = 2) without P20 | Control (n = 1) with P20 |
|---|---|---|---|---|
| Concentration (mg/mL) | 32.3 | 32.9 | 33.8 | 31.8 |
| Optical Density at 320 nm | 0.164 | 0.160 | 0.163 | 0.169 |
| SEC-HPLC (% main peak) | 99.5 | 99.5 | 99.5 | 99.6 |
| pH | 6.1 | 6.1 | 6.0 | 6.0 |
| Specific Activity (U/mg) | 64 | 63 | 62 | 72 |

TABLE 24

RESULTS OF 48 HOURS OF SHAKING ON DRUG
PRODUCT IN THE ABSENCE OF
POLYSORBATE 20 WITH 3 ML FILL IN 3 ML VIAL

| Assay | Baseline | Shaken Drug Product after 4 hrs (n = 1) without P20 | Shaken Drug Product after 48 hrs (n = 1) without P20 | Control (n = 1) with P20 |
|---|---|---|---|---|
| Concentration (mg/mL) | 31.02 | 34.4 | 32.1 | 32.6 |
| Optical Density at 320 nm | 0.152 | 0.163 | 0.166 | 0.151 |
| SEC-HPLC (% main peak) | 99.6 | 99.6 | 99.6 | 99.6 |
| pH | 6.0 | 6.0 | 5.9 | 6.0 |
| Specific Activity (U/mg) | 70 | 64 | 65 | 71 |

Buffering Capacity Studies

For determination of the buffering capacity of rhASA, product was titrated in triplicate, with either dilute acid or dilute base. Aliquots of 10 mL of drug substance at either 38 or 30 mg/mL (the latter to mimic drug product) were placed in a 20 mL glass vial to which a micro stir bar was added. Aliquots of 1 µL of 1N hydrochloric acid (HCl) were added to the protein solution, the contents mixed, and the pH was recorded. The experiment continued with addition of 1 uL HCl spikes, without rinsing the pH probe in between the measurements to avoid any dilution, until an approximate pH of 5.5 was achieved. The experiment was performed in triplicate and 5 mM phosphate buffer containing 150 mM sodium chloride, pH 6.0, was titrated side-by-side for comparison. Similarly, drug substance at both concentrations was titrated with 1M sodium hydroxide (NaOH) until a final pH of approximately 6.5 was achieved. In order to investigate the presence of any residual phosphate in rhASA, drug substance was analyzed by inductively coupling plasma mass spectroscopy (ICP-MS). The buffering capacity of diluted rhASA drug substance was also investigated to ensure that the pH value of solution did not change upon dilution of protein solution. Diluted samples ranging from 30 mg/mL to 1 mg/mL were prepared in 1.5 mL eppendorf tubes and the pH values were measured at the onset of dilution and after one week of storage at 2-8° C.

Figure 10:
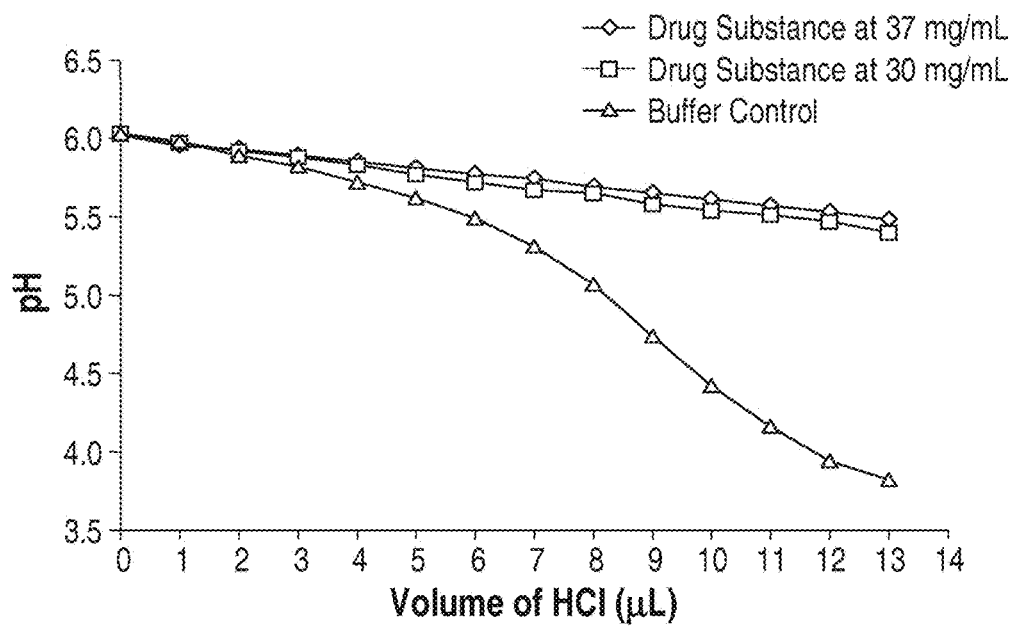
FIG. 10 illustrates exemplary data demonstrating the buffering capacity of rhASA drug substance compared to buffer control when titrated with hydrochloric acid.

The results of dilute acid and dilute base titration studies demonstrated adequate buffering capacity of rhASA solutions. For titration studies using HCl, initially the addition of approximately 2 µL of 1 M acid did not alter the pH of either drug substance or the buffer control. Increasing volumes of acid, however, demonstrated a dramatic decline on the pH of buffer compared to rhASA drug substance. After addition of 13 µL of 19 M HCl, the pH of the buffer control was more than 2 pH units lower than the pH of drug substance. A drug substance concentration of 30 mg/mL was also included in this experiment to mimic the drug product concentration. FIG. 10 illustrates the buffering capacity of rhASA drug substance compared to 5 mM sodium phosphate buffer, pH 6.3 with 150 mM sodium chloride when titrated with acid.

Figure 11:
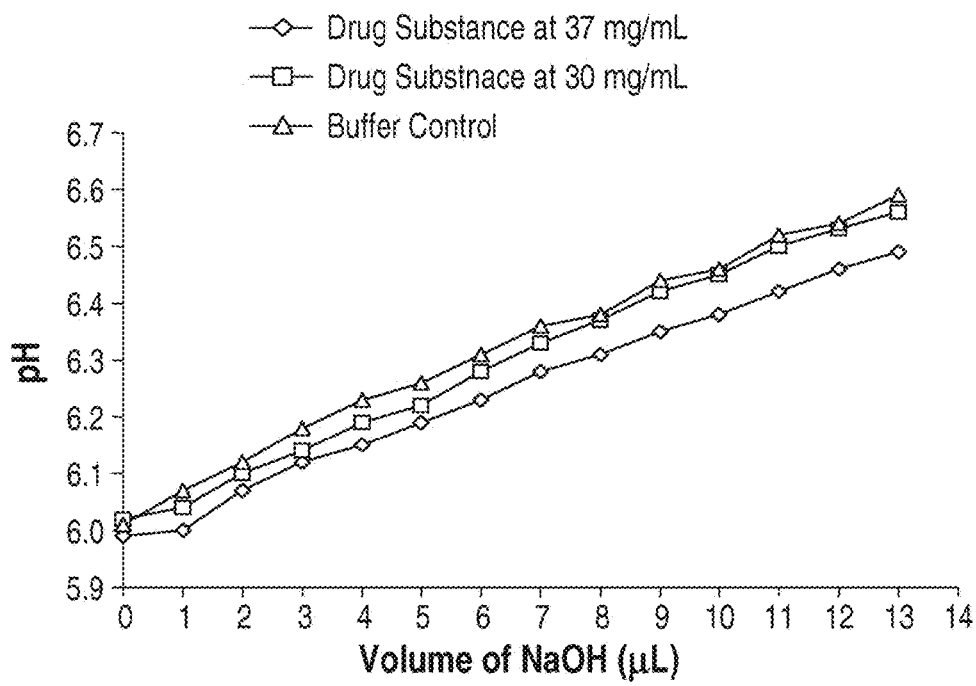
FIG. 11 illustrates exemplary data demonstrating the buffering capacity of rhASA drug substance compared to a buffer control when titrated with 1M sodium hydroxide.

The titration of rhASA drug substance with sodium hydroxide demonstrated relatively different results (FIG. 11) with respect to maintaining the pH. The rate of pH change did not differ substantially between drug substance and the buffer control.

Based on the observed results, and without wishing to be bound by any theory, it is likely that rhASA is contributing to the buffering capacity of the solution since aspartic acid, glutamic acid, and histidine side chains have the ability to act as proton acceptors and/or donors in order to maintain the solution pH. The buffering capacity of this protein was also previously observed during preformulation studies when the "pH memory" effect was discovered. The retention of pH has been demonstrated several times both at the laboratory scale and at the large scale operations. Collectively, the results of these two experiments suggest that the buffering capacity of rhASA in saline is more predominant in the acidic direction. According to the literature, the buffering capacity for the lower pH values is a direct indication of larger numbers of aspartic acid and glutamic acid residues within a given protein compared to histidine residues. While not wishing to be bound by any theory, this can indeed be the case for arylsulfatase A where there are a total of 45 glutamic as well as aspartic acid residues compared to 18 histidine residues.

The buffering capacity of drug substance may also be attributable to residual bound phosphate which was shown to be present in drug substance using ICP-MS. Table 25 demonstrates the amount of residual phosphate present in three different LSDL drug substance lots. This data also confirms the consistency of the ultrafiltration and diafiltration steps for the pilot scale process.

TABLE 25

RESIDUAL AMOUNT OF PHOSPHATE IN DRUG
SUBSTANCE PRODUCED IN LSDL

| rhASA Lot No. | Phosphate Concentration (ppm) |
|---|---|
| 001 | 27 |
| 002 | 31 |
| 003 | 31 |

In order to further understand the buffering capacity of this protein, the effect of dilution on pH was also investigated. Upon dilution of rhASA drug substance with saline to lower protein concentrations, no change in the pH values of drug substance was observed. Subsequently, the diluted drug substances were stored at 2-8° C. for one week, after which the pH measurements were recorded. Table 26 summarizes the data. The results demonstrate that dilution and storage at 2-8° C. have no effect on the pH values of the diluted drug substance. These observations further support the conclusion of the acid and base titration studies which demonstrated adequate buffering capacity of rhASA drug substance formulated in saline.

TABLE 26

PH VALUES OF DILUTED RHASA DRUG SUBSTANCE

| Drug Substance Target Concentration (mg/mL) | Drug Substance Measured Concentration Using A280 (mg/mL) | Onset pH Value | pH Value after One Week of Storage at 2-8° C. |
|---|---|---|---|
| 37.0 | 38.8 | 6.00 | 6.20 |
| 30.0 | 33.4 | 6.07 | 6.10 |
| 25.0 | 28.3 | 6.04 | 6.09 |
| 20.0 | 20.1 | 6.02 | 6.12 |
| 10.0 | 9.2 | 6.04 | 6.10 |
| 5.0 | 4.5 | 6.03 | 6.11 |
| 1.0 | 1.0 | 6.00 | 6.07 |

Figure 12:
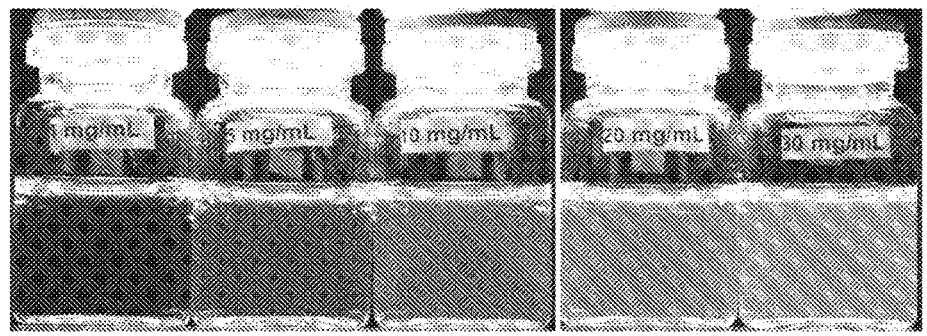
FIG. 12 depicts exemplary rhASA samples in saline, pH 6.0 varying by concentration.

During investigation of rhASA dilution and pH, it was observed that the appearance of diluted samples demonstrated a concentration dependent decrease in opalescence, i.e. rhASA samples with higher concentrations were more opalescent compared to the samples at lower concentrations which had an almost clear appearance. FIG. 12 exhibits the observed appearance of diluted rhASA. The 1 mg/mL rhASA solution demonstrated an appearance similar to water while the 30 mg/mL appearance was assessed to be between either Reference Suspensions II and III or III and IV.

Stability Studies

For stability studies, drug substance was formulated at 38±4 mg/mL in 154 mM NaCl, pH 6.0 and drug product was formulated at 30±3 mg/mL in 154 mM NaCl, pH 6.0 in the presence and absence of 0.005% polysorbate 20. Aliquots of 1 mL of drug substance were dispensed into 5 mL polycarbonate bottles with polypropylene screw closures and stored at ≤−65° C., −15° C. to −25° C., and 2-8° C. Aliquots of 1.0 to 1.1 mL of drug product were dispensed into 3 mL glass vials with 13 mm Flurotec stoppers and stored at 2-8° C., 25±2° C., and 40±2° C. Drug product vials were stored in the upright orientation for initial stability studies and changed to the inverted orientation for the latter studies using drug product without P20. At each time point, stability samples were tested by SEC-HPLC, RP-HPLC, OD320, protein concentrations, pH, specific activity, SDS-PAGE (Coomassie), and appearance. Peptide map, glycan map, and percent formylglycine were performed annually. Additionally, the latter assays were also performed for the stressed and accelerated conditions.

Collectively, the results of preformulation, freeze-thaw, and agitation studies suggest that only three formulations were suitable for further development. Long term stability studies were initiated in these three formulations in the presence of 0.005% P20. Table 27, Table 28, and Table 29 summarize the stability data for three formulations at selected time points.

TABLE 27

LONG TERM STABILITY AT 2-8° C. FOR RHASA IN 154 MM NACL, PH 5.9

| Test | Baseline | 3 m | 6 m | 11 m |
|---|---|---|---|---|
| Appearance | Clear to slightly opalescent | Clear to slightly opalescent | Clear to slightly opalescent | Clear to slightly opalescent |
| Protein Conc. (mg/mL) | 25.6 | 24.3 | 26.5 | 27.3 |
| SEC-HPLC (% main peak) at pH 5.5 | >99.9 | 99.8 | 99.9 | 99.8 |
| SEC-HPLC (% main peak) at pH 7.0 | 99.1 | 99.0 | 99.4 | 99.7 |
| RP-HPLC (% main peak) | 99.6 | 99.7 | 99.8 | >99.9 |
| pH | 5.9 | 6.0 | 6.0 | 6.0 |
| Specific Activity (U/mg) | 95 | 79 | 90 | 87 |
| SDS-Page (Coomassie) | Conforms to reference standard with no new bands with intensity greater than the 1% assay control | Conforms | Conforms | Conforms |

TABLE 28

LONG TERM STABILITY AT 2-8° C. FOR RHASA IN 154 MM NACL, PH 7.0

| Test | Baseline | 3 m | 6 m | 11 m |
|---|---|---|---|---|
| Appearance | Clear to slightly opalescent | Clear to slightly opalescent | Clear to slightly opalescent | Clear to slightly opalescent |
| Protein Conc. (mg/mL) | 27.3 | 26.9 | 28.1 | 29.2 |
| SEC-HPLC (% main peak) at pH 5.5 | 99.9 | 97.5 | 99.8 | >99.9 |
| SEC-HPLC (% main peak) at pH 7.0 | 99.4 | 99.0 | 99.2 | 99.8 |
| RP-HPLC (% main peak) | 99.6 | 99.7 | 99.9 | >99.9 |
| pH | 6.5 | 6.6 | 6.7 | 6.5 |
| Specific Activity (U/mg) | 112 | 88 | 98 | 86 |
| SDS-Page (Coomassie) | Conforms to reference standard with no new bands with intensity greater than the 1% assay control | Conforms | Conforms | Conforms |

TABLE 29

LONG TERM STABILITY AT 2-8° C. FOR RHASA IN 5 MM PHOSPHATE BUFFER WITH 145 MM NACL, PH 6.0

| Test | Baseline | 3 m | 6 m | 11 m |
|---|---|---|---|---|
| Appearance | Clear to slightly opalescent | Clear to slightly opalescent | Clear to slightly opalescent | Clear to slightly opalescent |
| Protein Conc. (mg/mL) | 27.9 | 27.4 | 27.1 | 29.3 |
| SEC-HPLC (% main peak) at pH 5.5 | 99.9 | 97.8 | 99.8 | 99.9 |
| SEC-HPLC (% main peak) at pH 7.0 | 98.9 | 98.9 | 99.2 | 99.9 |
| RP-HPLC (% main peak) | 99.7 | 99.6 | 99.8 | >99.9 |
| pH | 5.9 | 6.0 | 6.0 | 5.9 |
| Specific Activity (U/mg) | 87 | 88 | 95 | 90 |
| SDS-Page (Coomassie) | Conforms to reference standard with no new bands with intensity greater than the 1% assay control | Conforms | Conforms | Conforms |

Figure 13:
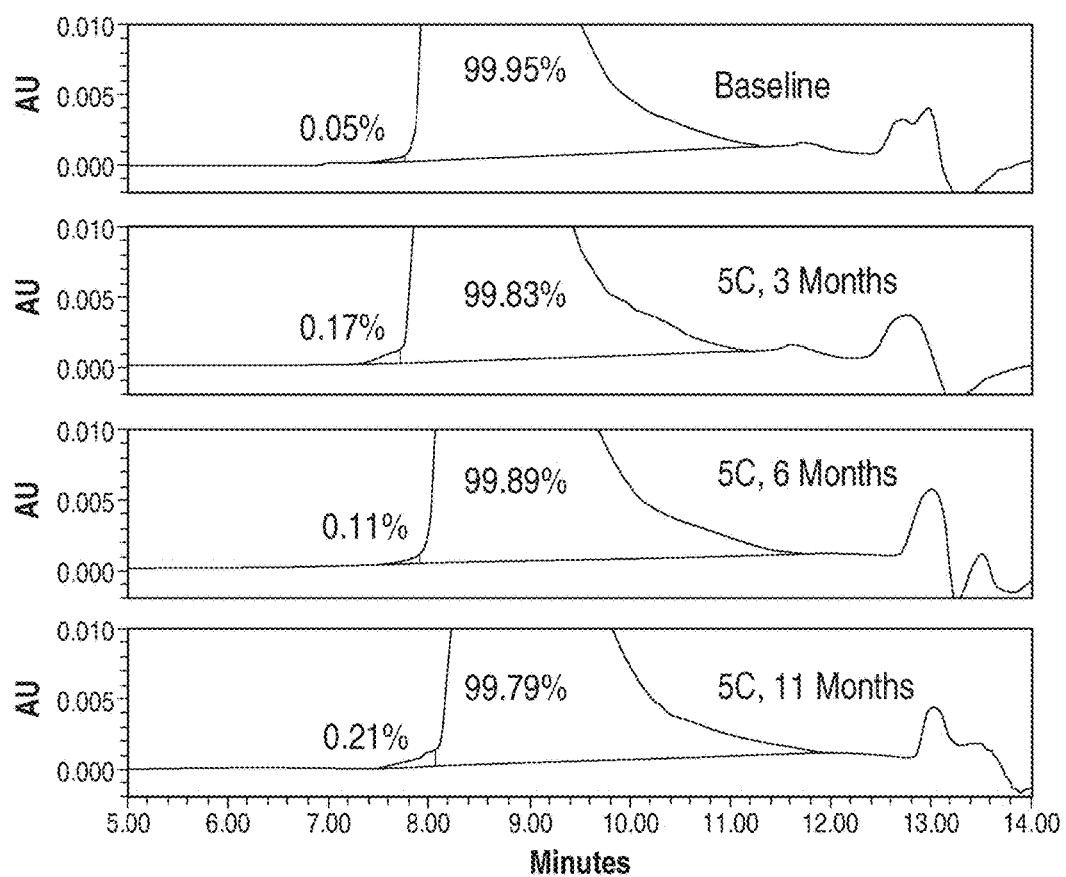
FIG. 13 illustrates exemplary SEC-HPLC analysis of rhASA (pH 5.5 mobile phase) in 154 mM NaCl, pH 5.9.
Figure 14:
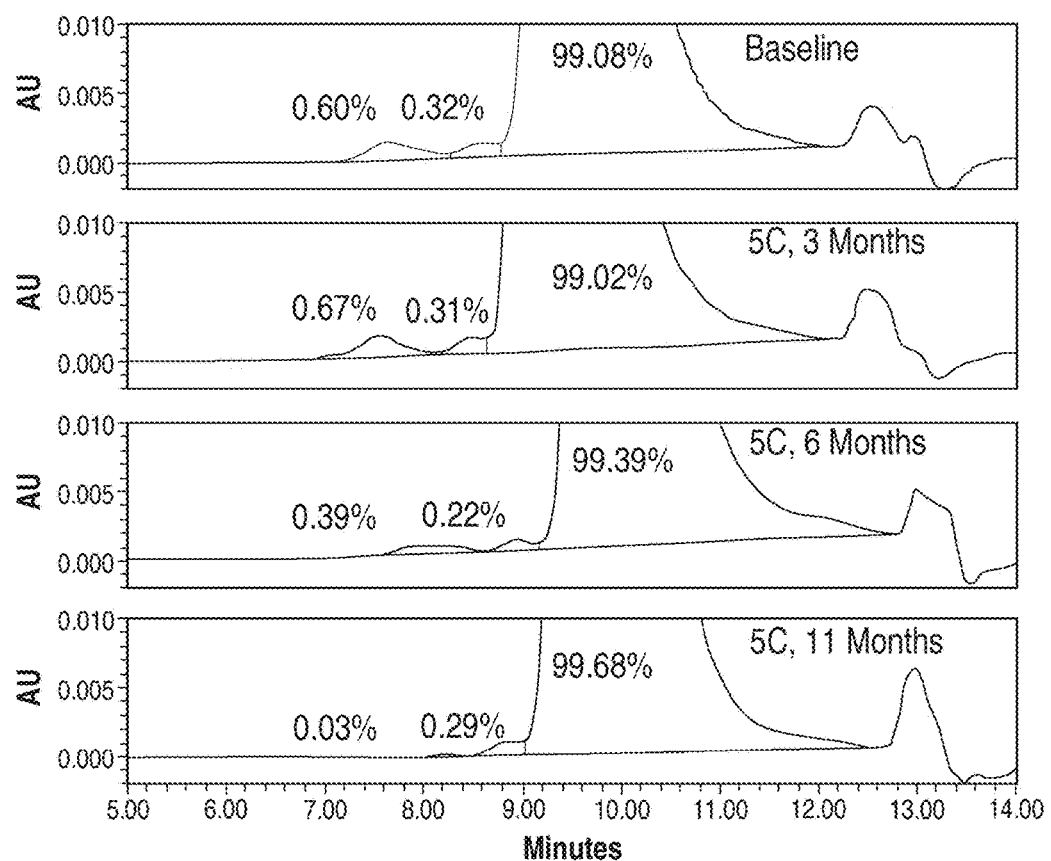
FIG. 14 illustrates exemplary SEC-HPLC analysis of rhASA (pH 7.0 mobile phase) in 154 mM NaCl, pH 5.9.
Figure 15:
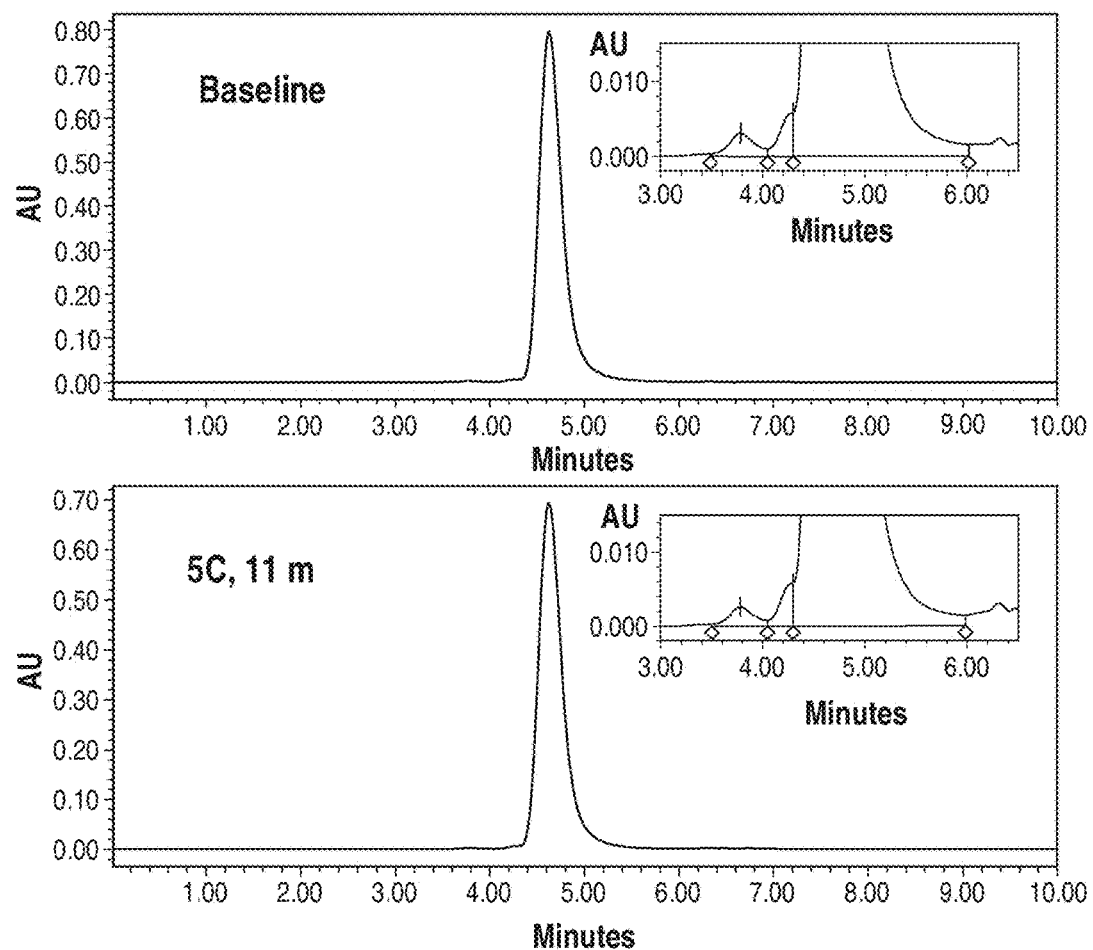
FIG. 15 illustrates exemplary size exclusion profiles of baseline and 11 month stability samples for rhASA in 154 mM NaCl, pH 5.

Stability studies, performed for up to 11 months at 2-8° C., suggested that the quality of rhASA is maintained in the prototype formulations. Representative size exclusion HPLC profiles of rhASA in saline, pH 5.9 are shown in FIGS. 13 and 14. Size exclusion HPLC did not detect any significant changes in the association state of rhASA after 11 months storage at 2-8° C.

Overall, the quality of drug product in all three candidate formulations was maintained after 11 months storage at 2-8° C.

Example 4—Toxicology

This example illustrates repeat dose intrathecal (IT) administration of rhASA from a toxicology and safety pharmacology perspective over a six-month period. The IT test article for this study was rhASA. Thirty-six male and 36 female cynomolgus monkeys were randomly assigned to five treatment groups. The animals in Group 1 were untreated implant device control (port & catheter) and were not dosed with the vehicle or test article; however, these animals were dosed with 0.6 mL of PBS on a schedule matching the test article dosing schedule. The animals in Groups 2-5 received 0.6 mL IT infusion of 0, 3, 10 or 31 mg/mL of rhASA (total dose of 0, 1.8, 6.0, or 18.6 mg) every other week (i.e. a total of 12 doses). Animals were necropsied at 6 months (24 hours post last IT dose), and the remaining 4 animals/sex/group were necropsied at the end of a 4-week recovery period. Selected tissues were harvested, saved and examined microscopically.

In general, the test article related changes could be categorized into two major types and were present at all dose levels (1.8, 6.0 and 18.6 mg/dose). Increase of infiltrates (of white blood cells, usually with a prominent eosinophilic component) in the meninges, the brain parenchyma, the spinal cord parenchyma, trigeminal ganglion, and occasionally the spinal nerve roots/ganglia (or the epineurium surrounding those structures). Without wishing to be bound by any theory, this increase was interpreted to be due to the presence of the test article (a protein) in the intrathecal space and in the nervous system tissues. Slight, focal increase of microglial cells in the spinal cord and brain in occasional animals (microgliosis was not observed in any high dose animals). Without wishing to be bound by any theory, both categories of morphologic changes were interpreted to be a response to the presence of the test article. There was no evidence of neuronal necrosis in any animal. None of the test article related changes were related to any biologically adverse reactions in the brain, spinal cord, spinal nerve roots or ganglia. Specifically, there was no evidence of neuronal necrosis or a biologically important glial response. There were no test article related lesions in the non-nervous system tissues.

Following a one-month recovery period (a dosing free period), the test article related changes had either entirely resolved or were limited to remnants of the prior increase in the inflammatory response associated with the presence of the test article. There were no adverse morphologic effects in the recovery animals. As based on a blinded microscopic examination assigning a semi-quantitative staining score, immunohistochemical staining for Arylsulfatase A (rhASA; the test article) was increased in the brain and spinal cord in various cell types, except neurons, for all test article treated groups at the terminal sacrifice. This increase was also apparent in the Kupffer cells of the liver. Following the 1-month recovery period, rhASA staining in the test article treated animals (all dose groups) had returned to control (device and/or vehicle control) levels. In one low dose recovery male, there were multiple foci of astrocytosis and neuronal loss, indicating multiple areas of prior ischemia, in the cerebral cortex. Although the exact pathogenesis of these lesions in this animal was not apparent, the lack of similar lesions in any other test article treated animals, including the high dose animals that received 10× the dose, indicated these lesions were not related to the test article.

The IT test article for this study was rhASA. Thirty-six male and 36 female cynomolgus monkeys were randomly assigned to five treatment groups. The animals in Group 1 were untreated implant device control (port & catheter) and were not dosed with the vehicle or test article; however, these animals were dosed with 0.6 mL of PBS on a schedule matching the test article dosing schedule. The animals in Groups 2-5 received 0.6 mL IT infusion of 0, 3, 10 or 31 mg/mL of rhASA (total dose of 0, 1.8, 6.0, or 18.6 mg) every other week (i.e. a total of 12 doses). Animals were necropsied at 6 months (24 hours post last IT dose), and the remaining 4 animals/sex/group were necropsied at the end of a 4-week recovery period. Selected tissues were harvested, saved and examined microscopically. The table below reflects the study design as it pertained to the pathology aspect of this study.

At the time of sacrifice, the brain was cut in a brain matrix at approximately 3 mm coronal slice thickness. The first slice and every second slice thereafter were fixed in formalin for histopathological evaluation and immunohistochemical analysis. The brain was processed as full coronal sections. These sections included at a minimum the following brain regions.

Neocortex (including frontal, parietal, temporal and occipital cortex): brain sections 1 to 8 (and slice 9 when present)

Paleocortex (olfactory bulbs and/or piriform lobe): brain sections 1 to 3

Basal ganglia (including caudate and putamen): brain sections 3 and 4

Limbic system (including hippocampus and cingulate gyri): brain sections 4 and 5

Thalamus/hypothalamus and midbrain regions including substantia nigra: brain sections 4 and 5.

Cerebellum, pons and medulla oblongata: brain sections 6 to 8 (and slice 9 when present).

The brain sections are listed in the data tables as sections 1 to 8/9 (a section 9 was provided by the testing facility for some animals). Sectioning varied slightly between animals. The brain sections (1 through 8/9) provided above were the approximate location of the various anatomic areas. The brain sections are listed in the data tables as individual sections, with diagnoses pertinent to that section, to facilitate potential, future additional slide review (if any). During data interpretation, individual brain anatomic sites (as listed above) were compared in order to identify any unique test article effects (i.e. unique to a particular brain region). At TPS, all brain sections from all animals were embedded in paraffin, sectioned at 5 microns, stained with hematoxylin and eosin (H&E) and examined microscopically. In addition, brains from the control and high dose animals were stained with Fluoro-Jade B (a stain increasing the sensitivity of evaluating the brain for neuronal degeneration) and a Bielschowsky's silver stain (a procedure that allows for direct visualization of axons, dendrites and neuronal filaments) and examined.

The spinal cord (cervical, thoracic and lumber) was cut into one centimeter sections. The first slice and every other slice thereafter were fixed in formalin for histopathological evaluation and immunohistochemical analysis. The spinal cord sections (cervical, thoracic (including the catheter tip) and lumbar) from all animals were sectioned at approximately 5 microns, stained with H&E and examined with transverse and oblique sections taken at each level. Serial spinal cord sections from the control and high dose groups were additionally stained with Bielschowsky's silver stain and anti-GFAP (an immunohistochemical stain that allows for the direct visualization of astrocytes and their processes).

Dorsal spinal nerve roots and ganglion (taken at mid-cervical, mid-thoracic, and mid-lumbar) were embedded in paraffin, with serial sections stained with H&E. In addition, serial sections from the control and high dose groups were stained with Bielschowsky's silver stain.

For the sciatic, tibial and sural nerve sections from all animals: A longitudinal section of each nerve was embedded in paraffin, sectioned at approximately 5 microns and stained with H&E. A cross section of each nerve was post-fixed in osmium, embedded in Spurr's resin, sectioned at approximately 1 to 2 microns and stained with toluidine blue. Osmium post-fixation and resin embedding provides for superior preservation of the myelin in peripheral nerves and thus a more detailed examination of the nerve.

All tissues collected and gross lesions harvested at necropsy from all animals were also embedded in paraffin, stained with H&E, and examined microscopically. Histopathological processing and evaluations and immunohistochemical analyses were performed by TPS.

Arylsulfatase A (rhASA) Staining

Positive control slides were supplied by the study sponsor. The slides were liver sections from mice injected with rhASA. The positive control slides all showed ample evidence of rhASA in Kupffer cells (sinusoidal macrophages) in the liver. The positive control slides are stored with the other slides from this study. All evaluations of the rhASA stained sections were initially conducted blinded to the treatment group of the animal. This was accomplished by having the pathologist initially read the rhASA stained slides with the animal number on the label obscured (by an assistant with knowledge of the actual animal being evaluated), dictating the score (severity grade) during evaluation, and having the same assistant immediately record the staining score (severity grade) into the data tables. The animal ID was then verified by both the study neuropathologist and the assistant to guarantee accurate data entry. This procedure was conducted so as to not introduce any bias into the judging of the overall intensity of staining with the immunohistochemical stain for the detection of intracellular rhASA. The relative degree of staining of neurons, meningeal macrophages, perivascular macrophages and glial cells (astrocytes and microglial cells but likely predominantly microglial cells) was graded in all the brain and spinal cord sections. The average severity scores at each brain and spinal cord level for each group was totaled (by group) and recorded as a total under the tissue heading Brain, General, rhASA Staining and Spinal Cord, General, rhASA Staining.

In general, rhASA staining in neurons of the brain was a measure of the neurons in the cerebral cortex and other nuclear areas in the brain. rhASA staining in meningeal macrophages was evidence of uptake of the test article by meningeal macrophages and/or endogenous rhASA in meningeal macrophages. rhASA staining of perivascular macrophages was a measure of uptake of rhASA by macrophages in the brain/spinal cord (or endogenous rhASA), although it should be noted that the perivascular space in the brain and spinal cord (the Virchow-Robins space) is continuous with the meninges. In general, the grading of rhASA staining in the glial cells was predominantly a measure of uptake of the test article/penetration of the test article into the gray and/or white matter, especially of the cerebral cortex (the corona radiata is the white matter beneath the cerebral cortex). The rhASA staining in the white matter appeared to be in astrocytes and microglial cells.

The following grading scheme was used to score the degree of rhASA staining the various cell types (neurons, glial cells, macrophages).

Grade Explanation (% of the Possible Cells Stained)
1 Less than 10%
2 Greater than 10 to 25%
3 Greater than 25 to 50%
4 Greater than 50 to 75%
5 Greater than 75%

Note this scheme is not strictly quantitative. It was used as an efficient, semi-quantitative method to assess the brain and spinal cord for the degree of staining with rhASA. It was noted by the Study Neuropathologist that not all neuronal areas had equal rhASA staining. It was also noted that there was endogenous neuronal staining in some control animals and that cells of the choroid plexus and neurons of the dorsal root ganglia tended to stain strongly for rhASA even in control animals. Staining of the choroid plexus and dorsal root ganglia was not graded but was noted by the study neuropathologist to be prominent, even in control animals.

Note: All dose groups: Low Dose=1.8 mg/dose; Mid dose=6.0 mg/dose; High dose=18.6 mg/dose. There were no test article related lesions in the non-nervous system tissues except for increased rhASA staining in the liver of all dose groups (male and female; see below).

Terminal Sacrifice Animals (6 Months EOW Dosing): rhASA Stained Sections

There was an increase of rhASA staining in the following tissues/cell types. When considering a test article effect on the degree of rhASA staining in a particular cell type in a particular dose group, the staining levels in the concurrent vehicle control and the device control (sacrificed with the recovery sacrifice animals) were considered for comparison.

Brain, Meninges, Macrophages (all dose groups, males and females)
Brain, Perivascular, Macrophages (all dose groups, males and females)
Brain, Glial Cells (all dose groups, males and females)
Spinal Cord, Meninges, Macrophages (all dose groups, males and females)
Spinal Cord, Perivascular, Macrophages (all dose groups, males and females)
Spinal Cord, Glial Cells (mid and high dose males and females)
Liver, Kupffer Cells (all dose groups, males and females)

Because of endogenous staining, rhASA staining levels in the neurons of the brain and spinal cord were the most difficult to specifically define. The rhASA staining demonstrated consistently increased levels of rhASA in the meningeal and brain/spinal cord perivascular macrophages and also within glial cells. There were no detectable differences of rhASA staining in neurons between the control and test article treated animals.

Recovery Sacrifice Animals (6 Months EOW Dosing Followed by 1 Month without Dosing)

In general, test article related changes were either totally resolved or were notably diminished in those animals allowed a one-month period without dosing prior to necropsy. The following microscopic changes were present at an incidence and/or severity that indicated a possible relationship to the test article.

Figure 16:
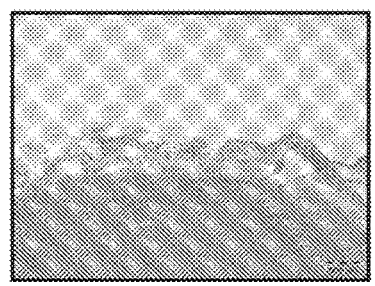
FIG. 16 depicts exemplary photo-micrographs of brain tissue, meninges, infiltrates (mid and high dose groups, both sexes) after treatment.
Figure 17:
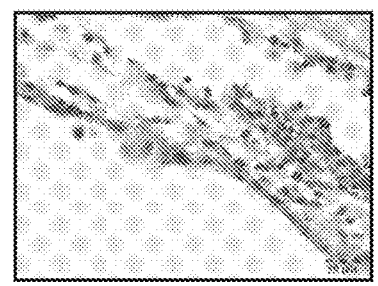
FIG. 17 depicts exemplary photo-micrographs of brain tissue, meninges, infiltrates (mid and high dose groups, both sexes) after treatment.
Figure 18:
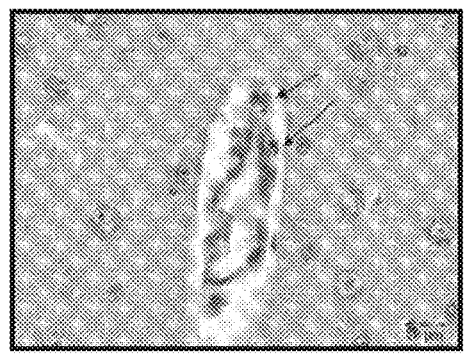
FIG. 18 depicts exemplary photo-micrographs of brain tissue, perivascular, infiltrates (mid dose males; high dose females) after treatment.

Test Article Related Microscopic Changes (Recovery Animals)
Brain, Meninges, Infiltrates (mid and high dose groups, both sexes) (FIGS. 16 and 17)
Brain, Meninges, Infiltrates, % Eosinophils (mid dose males; high dose females)
Brain, Perivascular, Infiltrates (mid dose males; high dose females) (FIG. 18)
Brain, Perivascular, Infiltrates, % Eosinophils (mid dose males; high dose females)
Brain, Gray Matter, Infiltrates (all dose groups, both sexes)
Brain, Gray Matter Infiltrates, % Eosinophils (low dose males)
Brain, Gray Matter, Eosinophils, Necrosis (low dose males)

Spinal Cord, Meninges, Infiltrates (mid and high dose males; low and high dose females)

Spinal Cord, Meninges, Infiltrates, % Eosinophils (mid dose males; low dose females)

Spinal Cord, Gray Matter, Infiltrates (low dose females)

Spinal Cord, Gray Matter, Infiltrates, % Eosinophils (low dose females)

Dorsal Root Ganglion and Roots, Epineurium, Infiltrates (mid dose females)

Spinal Nerve Roots and Ganglia, Infiltrates, Eosinophils (mid and high dose males; all doses, females)

Trigeminal Ganglion, Infiltrates, Eosinophils (mid dose males and females)

All these changes were interpreted to represent remnants of the increased inflammatory changes noted in the terminal sacrifice animals. As in the terminal sacrifice animals, there was no evidence the increase of inflammatory cell infiltrates still present in some recovery animals represented morphologic changes that were causing any adverse effects. There were no test article related lesions in the non-nervous system tissues.

Recovery Sacrifice Animals (6 Months EOW Dosing Followed by 1 Month without Dosing): rhASA Staining There was no indication of increased rhASA staining in the recovery males or females as compared to the device and/or vehicle controls. In the brain of the low, mid and high dose recovery males, there was actually an indication of decreased rhASA staining in some cell types (this varied among the treatment groups) as compared to the device and/or vehicle controls. The reason for this, including whether or not this was an actual effect, was not apparent. One possible explanation would be that administration of exogenous rhASA may cause some decrease in endogenous rhASA production. A similar finding was not present in the spinal cord of the males. In the recovery males and females, staining in the liver was similar to that noted in controls.

In general, the test article related changes could be categorized into two major types and were present at all dose levels (1.8, 6.0 and 18.6 mg/dose).

Increase of infiltrates (of white blood cells, usually with a prominent eosinophilic component) in the meninges, the brain parenchyma, the spinal cord parenchyma, trigeminal ganglion, and occasionally the spinal nerve roots/ganglia (or the epineurium surrounding those structures). This increase was interpreted to be due to the presence of the test article (a protein) in the intrathecal space and in the nervous system tissues.

Slight, focal increase of microglial cells in the spinal cord and brain in occasional animals (microgliosis was not observed in any high dose animals). Both categories of morphologic changes were interpreted to be a response to the presence of the test article. There was no evidence of neuronal necrosis in any animal. None of the test article related changes were related to any biologically adverse reactions in the brain, spinal cord, spinal nerve roots or ganglia. Specifically, there was no evidence of neuronal necrosis or a biologically important glial response. There were no test article related lesions in the non-nervous system tissues. Following a one-month recovery period (a dosing free period), the test article related changes had either entirely resolved or were limited to remnants of the prior increase in the inflammatory response associated with the presence of the test article. There were no adverse morphologic effects in the recovery animals.

As based on a blinded microscopic examination assigning a semi-quantitative staining score, immunohistochemical staining for Arylsulfatase A (rhASA; the test article) was increased in the brain and spinal cord in various cell types, except neurons, for all test article treated groups. This increase was also apparent in the Kupffer cells of the liver. Following the 1-month recovery period, rhASA staining in the test article treated animals (all dose groups) had returned to control (device and/or vehicle control) levels. In one low dose recovery male, there were multiple foci of astrocytosis and neuronal loss, indicating multiple areas of prior ischemia, in the cerebral cortex. Although the exact pathogenesis of these lesions in this animal was not apparent, the lack of similar lesions in any other test article treated animals, including the high dose animals that received 10× the dose, indicated these lesions were not related to the test article. Based strictly on the gross and microscopic findings (on the paraffin embedded, hematoxylin and eosin stained sections) in this study, the no observed adverse effect level (NOAEL) was 18.6 mg.

Example 5—Pharmakinetic Data

6 Month Animal Data

This example provides interpretive analysis for serum and CSF concentrations of rhASA and anti-rhASA serum antibodies from Northern Biomedical Research, Inc.

The objective of the example was to evaluate repeat dose intrathecal (IT) administration of rhASA from a toxicology and safety pharmacology perspective in juvenile (<12 months of age) cynomolgus monkeys. A total of 12 doses were given in a six month period. Animals were necropsied 24 hours or one-month after the last dose. The study design is shown in Table 30.

TABLE 30

Study Design

| Group | No. of Animals | Nominal Dose Concentration (mg/mL) | Administered Dose (mg) | No. of Animals, 6 Month Sacrifice | No. of Animals, 1 Month Recovery Sacrifice |
|---|---|---|---|---|---|
| 1 | 4 M, 4 F | DC | 0 | — | 4 M, 4 F |
| 2 | 8 M, 8 F | 0 | 0 | 4 M, 3 F[a] | 4 M, 4 F |
| 3 | 8 M, 8 F | 3 | 1.8 | 4 M, 4 F | 4 M, 4 F |
| 4 | 8 M, 8 F | 10 | 6.0 | 4 M, 4 F | 4 M, 4 F |
| 5 | 8 M, 8 F | 31 | 18.6 | 4 M, 4 F | 4 M, 4 F |

DC = Device Control; Animals in Group 1 were not dosed with vehicle or test article.
[a]Vehicle Control Animal No. 044 was sacrificed early on Day 50 due to a leaking catheter Assay Methods—Antibody Analysis Quantitation of anti-rhASA antibodies in the serum and CSF from cynomolgus monkeys was conducted using a validated method. Briefly, the assay begins by blocking a MSD streptavidin coated plate, followed by incubation with biotin-labeled rhASA. After a washing step, diluted samples, calibrators, and QCs are added to the plate and incubated. After an additional wash step, SULFO TAG-labelled drug is added and incubated. A final wash step is performed and MSD read buffer is added. Plates are read immediately. The signal data in relative luminescence units (RLU) are analyzed using SOFTMax Pro templates.

Serum and CSF Concentration

Quantitation of rhASA in the serum and CSF from cynomolgus monkeys was conducted using a validated method. The method is based on Enzyme-Linked Immunosorbent Assay (ELISA) technology. Briefly, a microtiter plate is coated with a rabbit polyclonal antibody (SH040)

raised against recombinant human Arylsulfatase A (ASA). After incubation with ASA reference standards and test samples, bound ASA protein is detected by horseradish peroxidase (HRP)-conjugated anti-ASA monoclonal antibody (clone 19-16-3). The plate is then incubated with a substrate for HRP, TMB peroxidase. This enzyme-substrate reaction is stopped by the addition of 2N sulfuric acid ($H_2SO_4$) and the absorbance of each well is measured at the absorbance wavelength 450 nm with a reference wavelength 655 nm. The concentrations of ASA in samples are calculated using the rhASA calibration curve in the same plate.

Summaries of serum concentrations of rhASA, CSF concentrations of rhASA, anti-rhASA serum antibody concentrations, anti-rhASA CSF antibody concentrations, and incidence of antibodies by group and sex are presented in Table 33-39 below.

TABLE 33

Summary of Serum Concentration of rhASA in Cynomolgus Monkeys

| Time point | Male Mean ng/mL | SD ng/mL | n | Female Mean ng/mL | SD ng/mL | n |
|---|---|---|---|---|---|---|
| Group 1: Vehicle control ||||||| 
| Prior to Dose 2 | 0 | 0 | 4 | 0 | 0 | 4 |
| Post Dose 2 | 0 | 0 | 4 | 0 | 0 | 4 |
| Prior to Dose 4 | 0 | 0 | 4 | 0 | 0 | 4 |
| Post Dose 4 | 0 | 0 | 4 | 0 | 0 | 4 |
| Prior to Dose 6 | 0 | 0 | 4 | 0 | 0 | 4 |
| Post Dose 6 | 0 | 0 | 4 | 0 | 0 | 4 |
| Prior to Dose 8 | 0 | 0 | 4 | 0 | 0 | 4 |
| Post Dose 8 | 0 | 0 | 4 | 0 | 0 | 4 |
| Prior to Dose 10 | 0 | 0 | 4 | 0 | 0 | 4 |
| Post Dose 10 | 0 | 0 | 4 | 0 | 0 | 4 |
| Prior to Dose 12 | 0 | 0 | 4 | 0 | 0 | 4 |
| Post Dose 12 | 0 | 0 | 4 | 0 | 0 | 4 |
| Mid Recovery | 0 | 0 | 4 | 0 | 0 | 4 |
| Recovery Necropsy | 0 | 0 | 4 | 0 | 0 | 4 |
| Group 2: 0 mg |||||||
| Prior to Dose 2 | 0 | 0 | 8 | 0 | 0 | 7 |
| Post Dose 2 | 0 | 0 | 8 | 0 | 0 | 7 |
| Prior to Dose 4 | 0 | 0 | 8 | 0 | 0 | 7 |
| Post Dose 4 | 0 | 0 | 8 | 0 | 0 | 7 |
| Prior to Dose 6 | 0 | 0 | 8 | 0 | 0 | 8 |
| Post Dose 6 | 0 | 0 | 8 | 0 | 0 | 8 |
| Prior to Dose 8 | 0 | 0 | 8 | 0 | 0 | 8 |
| Post Dose 8 | 0 | 0 | 8 | 0 | 0 | 8 |
| Prior to Dose 10 | 0 | 0 | 8 | 0 | 0 | 7 |
| Post Dose 10 | 0 | 0 | 8 | 0 | 0 | 7 |
| Prior to Dose 12 | 0 | 0 | 8 | 0 | 0 | 7 |
| Post Dose 12 (Prior to 6-month Necropsy) | 0 | 0 | 8 | 0 | 0 | 8 |
| Mid Recovery | 0 | 0 | 4 | 0 | 0 | 4 |
| Recovery Necropsy | 0 | 0 | 4 | 0 | 0 | 4 |
| Group 3: 1.8 mg |||||||
| Prior to Dose 2 | 0 | 0 | 8 | 0 | 0 | 8 |
| Post Dose 2 | 49.2 | 46.8 | 8 | 40.3 | 27.3 | 8 |
| Prior to Dose 4 | 0 | 0 | 8 | 0 | 0 | 8 |
| Post Dose 4 | 0 | 0 | 8 | 0 | 0 | 8 |
| Prior to Dose 6 | 0 | 0 | 8 | 0 | 0 | 8 |
| Post Dose 6 | 0 | 0 | 8 | 0 | 0 | 8 |
| Prior to Dose 8 | 0 | 0 | 8 | 0 | 0 | 8 |
| Post Dose 8 | 0 | 0 | 8 | 0 | 0 | 8 |
| Prior to Dose 10 | 0 | 0 | 8 | 0 | 0 | 8 |
| Post Dose 10 | 0 | 0 | 8 | 0 | 0 | 8 |
| Prior to Dose 12 | 0 | 0 | 8 | 0 | 0 | 8 |
| Post Dose 12 (Prior to 6-month Necropsy) | 0 | 0 | 8 | 0 | 0 | 8 |
| Mid Recovery | 0 | 0 | 4 | 0 | 0 | 4 |
| Recovery Necropsy | 0 | 0 | 4 | 0 | 0 | 4 |
| Group 4: 6.0 mg |||||||
| Prior to Dose 2 | 0 | 0 | 8 | 0 | 0 | 8 |
| Post Dose 2 | 173.6 | 69.5 | 8 | 143.2 | 89.0 | 8 |
| Prior to Dose 4 | 0 | 0 | 8 | 0 | 0 | 8 |
| Post Dose 4 | 17 | 49 | 8 | 63.8 | 119.9 | 8 |
| Prior to Dose 6 | 0 | 0 | 8 | 0 | 0 | 8 |
| Post Dose 6 | 0 | 0 | 8 | 0 | 0 | 8 |
| Prior to Dose 8 | 0 | 0 | 8 | 0 | 0 | 8 |
| Post Dose 8 | 0 | 0 | 8 | 0 | 0 | 8 |
| Prior to Dose 10 | 0 | 0 | 8 | 0 | 0 | 8 |
| Post Dose 10 | 0 | 0 | 8 | 0 | 0 | 8 |
| Prior to Dose 12 | 0 | 0 | 8 | 0 | 0 | 8 |
| Post Dose 12 (Prior to 6-month Necropsy) | 0 | 0 | 8 | 0 | 0 | 8 |
| Mid Recovery | 0 | 0 | 4 | 0 | 0 | 4 |
| Recovery Necropsy | 0 | 0 | 4 | 0 | 0 | 4 |
| Group 5: 18.6 mg |||||||
| Prior to Dose 2 | 0 | 0 | 8 | 0 | 0 | 8 |
| Post Dose 2 | 348.0 | 272.9 | 8 | 562.3 | 204.3 | 8 |
| Prior to Dose 4 | 0 | 0 | 8 | 0 | 0 | 8 |
| Post Dose 4 | 105.7 | 274.6 | 8 | 172.0 | 141.3 | 8 |
| Prior to Dose 6 | 0 | 0 | 8 | 0 | 0 | 8 |
| Post Dose 6 | 20.4 | 38.4 | 8 | 88.6 | 121.4 | 8 |
| Prior to Dose 8 | 0 | 0 | 8 | 0 | 0 | 8 |
| Post Dose 8 | 0 | 0 | 8 | 54.0 | 89.4 | 8 |
| Prior to Dose 10 | 0 | 0 | 8 | 0 | 0 | 8 |
| Post Dose 10 | 0 | 0 | 8 | 6 | 18 | 8 |
| Prior to Dose 12 | 0 | 0 | 8 | 0 | 0 | 8 |
| Post Dose 12 (Prior to 6-month Necropsy) | 0 | 0 | 8 | 0 | 0 | 8 |
| Mid Recovery | 0 | 0 | 4 | 0 | 0 | 4 |
| Recovery Necropsy | 0 | 0 | 4 | 0 | 0 | 4 |

TABLE 34

Summary of CSF Concentrations in Cynomolgus Monkeys

| Time point | Male Mean ng/mL | SD ng/mL | n | Female Mean ng/mL | SD ng/mL | n |
|---|---|---|---|---|---|---|
| Group 1: Vehicle Control |||||||
| Prior to Dose 2 | 0 | 0 | 4 | 0 | 0 | 4 |
| Post Dose 2 | 0 | 0 | 4 | 0 | 0 | 4 |
| Prior to Dose 4 | 0 | 0 | 4 | 0 | 0 | 4 |
| Post Dose 4 | 0 | 0 | 4 | 0 | 0 | 4 |
| Prior to Dose 6 | 0 | 0 | 4 | 0 | 0 | 4 |
| Post Dose 6 | 0 | 0 | 4 | 0 | 0 | 4 |
| Prior to Dose 8 | 0 | 0 | 4 | 0 | 0 | 4 |
| Post Dose 8 | 0 | 0 | 4 | 0 | 0 | 4 |
| Prior to Dose 10 | 0 | 0 | 4 | 0 | 0 | 4 |
| Post Dose 10 | 0 | 0 | 3 | 0 | 0 | 4 |
| Prior to Dose 12 | 0 | 0 | 3 | 0 | 0 | 4 |
| Post Dose 12 | 0 | 0 | 3 | 0 | 0 | 4 |
| Mid Recovery | 0 | 0 | 3 | 0 | 0 | 4 |
| Recovery Necropsy | 0 | 0 | 4 | 0 | 0 | 4 |
| Group 2: 0 mg |||||||
| Prior to Dose 2 | 0 | 0 | 6 | 0 | 0 | 7 |
| Post Dose 2 | 0 | 0 | 5 | 0 | 0 | 7 |
| Prior to Dose 4 | 0 | 0 | 5 | 0 | 0 | 6 |

TABLE 34-continued

Summary of CSF Concentrations in Cynomolgus Monkeys

| Time point | Male Mean ng/mL | SD ng/mL | n | Female Mean ng/mL | SD ng/mL | n |
|---|---|---|---|---|---|---|
| Post Dose 4 | 0 | 0 | 5 | 0 | 0 | 5 |
| Prior to Dose 6 | 0 | 0 | 5 | 0 | 0 | 5 |
| Post Dose 6 | 0 | 0 | 5 | 0 | 0 | 5 |
| Prior to Dose 8 | 0 | 0 | 5 | 0 | 0 | 5 |
| Post Dose 8 | 0 | 0 | 5 | 0 | 0 | 5 |
| Prior to Dose 10 | 0 | 0 | 4 | 0 | 0 | 5 |
| Post Dose 10 | 0 | 0 | 4 | 0 | 0 | 5 |
| Prior to Dose 12 | 0 | 0 | 4 | 0 | 0 | 5 |
| Post Dose 12 (Prior to 6-month Necropsy) | 0 | 0 | 5 | 0 | 0 | 5 |
| Mid Recovery | 0 | 0 | 2 | 0 | 0 | 3 |
| Recovery Necropsy | 0 | 0 | 4 | 0 | 0 | 4 |
| Group 3: 1.8 mg | | | | | | |
| Prior to Dose 2 | 42491 | 59255 | 7 | 42217 | 47300 | 6 |
| Post Dose 2 | 95886 | 22626 | 7 | 125717 | 61723 | 6 |
| Prior to Dose 4 | 17664 | 24372 | 6 | 50829 | 41891 | 6 |
| Post Dose 4 | 106783 | 42823 | 6 | 138400 | 49908 | 6 |
| Prior to Dose 6 | 39400 | 50105 | 4 | 45817 | 38404 | 6 |
| Post Dose 6 | 95275 | 12836 | 4 | 104080 | 37423 | 5 |
| Prior to Dose 8 | 25799 | 31589 | 4 | 58086 | 43821 | 5 |
| Post Dose 8 | 148750 | 34664 | 4 | 119200 | 66556 | 5 |
| Prior to Dose 10 | 25927 | 31380 | 4 | 30380 | 30328 | 5 |
| Post Dose 10 | 89975 | 29494 | 4 | 105200 | 44603 | 5 |
| Prior to Dose 12 | 29746 | 34267 | 4 | 82780 | 65906 | 5 |
| Post Dose 12 (Prior to 6-month Necropsy) | 32030 | 39155 | 7 | 47331 | 49015 | 6 |
| Mid Recovery | 0 | 0 | 3 | 0 | 0 | 2 |
| Recovery Necropsy | 0 | 0 | 4 | 0 | 0 | 4 |
| Group 4: 6.0 mg | | | | | | |
| Prior to Dose 2 | 75203 | 67002 | 8 | 146979 | 233673 | 6 |
| Post Dose 2 | 360000 | 179276 | 8 | 267667 | 103369 | 6 |
| Prior to Dose 4 | 58064 | 77210 | 8 | 53285 | 73340 | 5 |
| Post Dose 4 | 369250 | 241251 | 8 | 305517 | 152232 | 6 |
| Prior to Dose 6 | 77253 | 91407 | 8 | 97987 | 146762 | 6 |
| Post Dose 6 | 418600 | 200098 | 5 | 369000 | 232238 | 5 |
| Prior to Dose 8 | 66342 | 80374 | 5 | 11592 | 23072 | 4 |
| Post Dose 8 | 329400 | 209841 | 5 | 340500 | 135128 | 4 |
| Prior to Dose 10 | 119420 | 148408 | 5 | 74031 | 104609 | 2 |
| Post Dose 10 | 412000 | 149278 | 5 | 245500 | 161927 | 2 |
| Prior to Dose 12 | 68651 | 92902 | 5 | 74577 | 105251 | 2 |
| Post Dose 12 (Prior to 6-month Necropsy) | 141833 | 173933 | 7 | 58986 | 99016 | 4 |
| Mid Recovery | 0 | 0 | 3 | 0 | NA | 1 |
| Recovery Necropsy | 0 | 0 | 4 | 0 | 0 | 4 |
| Group 5: 18.6 mg | | | | | | |
| Prior to Dose 2 | 289917 | 291188 | 7 | 201339 | 250774 | 8 |
| Post Dose 2 | 734429 | 298352 | 7 | 920143 | 448409 | 7 |
| Prior to Dose 4 | 150238 | 210302 | 7 | 169895 | 185675 | 6 |
| Post Dose 4 | 984857 | 570039 | 7 | 965167 | 425924 | 6 |
| Prior to Dose 6 | 265479 | 252067 | 7 | 288879 | 226889 | 6 |
| Post Dose 6 | 758143 | 102009 | 7 | 1270000 | 558533 | 6 |
| Prior to Dose 8 | 190529 | 240081 | 7 | 196021 | 199396 | 6 |
| Post Dose 8 | 1003429 | 538271 | 7 | 989800 | 585072 | 5 |
| Prior to Dose 10 | 176297 | 272500 | 7 | 168864 | 191087 | 6 |
| Post Dose 10 | 1013000 | 390673 | 7 | 773400 | 103717 | 5 |
| Prior to Dose 12 | 142334 | 196793 | 5 | 430542 | 436534 | 6 |
| Post Dose 12 (Prior to 6-month Necropsy) | 291525 | 350251 | 7 | 252142 | 381200 | 6 |
| Mid Recovery | 0 | 0 | 3 | 0 | 0 | 2 |
| Recovery Necropsy | 0 | 0 | 4 | 0 | 0 | 4 |

TABLE 35

Summary of Anti-rhASA Antibody Concentration in Serum

| Time point | Male Mean ng/mL | SD ng/Ml | n | Female Mean ng/mL | SD ng/mL | n |
|---|---|---|---|---|---|---|
| Group 1: Vehicle control | | | | | | |
| Predose 2 | 0 | 0 | 4 | 0 | 0 | 4 |
| Predose 4 | 0 | 0 | 4 | 0 | 0 | 4 |
| Predose 6 | 0 | 0 | 4 | 0 | 0 | 4 |
| Predose 8 | 0 | 0 | 4 | 0 | 0 | 4 |
| Predose 10 | 0 | 0 | 4 | 0 | 0 | 4 |
| Predose 12 | 0 | 0 | 4 | 0 | 0 | 4 |
| Mid Recovery | 0 | 0 | 4 | 0 | 0 | 4 |
| Recovery Necropsy | 0 | 0 | 4 | 0 | 0 | 4 |
| Group 2: 0 mg | | | | | | |
| Predose 2 | 0 | 0 | 8 | 0 | 0 | 8 |
| Predose 4 | 0 | 0 | 8 | 0 | 0 | 8 |
| Predose 6 | 0 | 0 | 8 | 0 | 0 | 7 |
| Predose 8 | 0 | 0 | 8 | 0 | 0 | 7 |
| Predose 10 | 0 | 0 | 8 | 0 | 0 | 7 |
| Predose 12 | 0 | 0 | 8 | 0 | 0 | 7 |
| Necropsy (24 hr after last dose) | 0 | 0 | 4 | 0 | 0 | 4 |
| Mid Recovery | 0 | 0 | 4 | 0 | 0 | 4 |
| Recovery Necropsy | 0 | 0 | 4 | 0 | 0 | 4 |
| Group 3: 1.8 mg | | | | | | |
| Predose 2 | 0 | 0 | 8 | 0 | 0 | 8 |
| Predose 4 | 18409 | 21371 | 8 | 27648 | 37504 | 8 |
| Predose 6 | 75913 | 64863 | 8 | 85625 | 79871 | 8 |
| Predose 8 | 132163 | 95576 | 8 | 151900 | 97818 | 8 |
| Predose 10 | 392338 | 606626 | 8 | 290675 | 186213 | 8 |
| Predose 12 | 499438 | 735028 | 8 | 524438 | 569523 | 8 |
| Necropsy (24 hr after last dose) | 261625 | 157865 | 4 | 733550 | 928411 | 4 |
| Mid Recovery | 339250 | 265888 | 4 | 377175 | 218955 | 4 |
| Recovery Necropsy | 712500 | 1107129 | 4 | 295525 | 174718 | 4 |
| Group 4: 6.0 mg | | | | | | |
| Predose 2 | 0 | 0 | 8 | 0 | 0 | 8 |
| Predose 4 | 30419 | 30561 | 8 | 64000 | 89510 | 8 |
| Predose 6 | 143693 | 128094 | 8 | 191750 | 150511 | 8 |
| Predose 8 | 325750 | 190651 | 8 | 305850 | 224707 | 8 |
| Predose 10 | 669125 | 515458 | 8 | 832188 | 846241 | 8 |
| Predose 12 | 946125 | 651530 | 8 | 1060775 | 1088889 | 8 |
| Necropsy (24 hr after last dose) | 713500 | 598812 | 4 | 1047568 | 1132048 | 4 |
| Mid Recovery | 1566000 | 708132 | 4 | 975500 | 1149734 | 4 |
| Recovery Necropsy | 1113250 | 554510 | 4 | 793000 | 991450 | 4 |
| Group 5: 18.6 mg | | | | | | |
| Predose 2 | 0 | 0 | 8 | 0 | 0 | 8 |
| Predose 4 | 56873 | 39107 | 8 | 39994 | 53411 | 8 |
| Predose 6 | 311638 | 237796 | 8 | 193263 | 208952 | 8 |
| Predose 8 | 482875 | 270130 | 8 | 399363 | 360425 | 8 |
| Predose 10 | 1006750 | 857916 | 8 | 866875 | 894776 | 8 |
| Predose 12 | 1419000 | 1382276 | 8 | 1341500 | 1373771 | 8 |
| Necropsy (24 hr after last dose) | 165000 | 147463 | 4 | 407300 | 268570 | 4 |
| Mid Recovery | 2884250 | 1363128 | 4 | 2101500 | 2090420 | 4 |
| Recovery Necropsy | 2504250 | 1118042 | 4 | 1506000 | 1524682 | 4 |

TABLE 36

Summary of Anti-rhASA Antibody Concentration in CSF

| | Male | | | Female | | |
|---|---|---|---|---|---|---|
| Time point | Mean ng/mL | SD ng/mL | n | Mean ng/mL | SD ng/mL | n |
| Group 1: Vehicle control | | | | | | |
| Surgery | 0 | 0 | 4 | 0 | 0 | 4 |
| Predose 2 | 0 | 0 | 4 | 0 | 0 | 4 |
| Predose 4 | 0 | 0 | 4 | 0 | 0 | 4 |
| Predose 6 | 0 | 0 | 4 | 0 | 0 | 4 |
| Predose 8 | 0 | 0 | 4 | 0 | 0 | 4 |
| Predose 10 | 0 | 0 | 4 | 0 | 0 | 4 |
| Predose 12 | 0 | 0 | 3 | 0 | 0 | 4 |
| Mid Recovery | 0 | 0 | 3 | 0 | 0 | 4 |
| Recovery Necropsy | 0 | 0 | 4 | 0 | 0 | 4 |
| Group 2: 0 mg | | | | | | |
| Surgery | 0 | 0 | 7 | 0 | 0 | 6 |
| Predose 2 | 0 | 0 | 6 | 0 | 0 | 7 |
| Predose 4 | 0 | 0 | 5 | 0 | 0 | 6 |
| Predose 6 | 0 | 0 | 5 | 0 | 0 | 5 |
| Predose 8 | 0 | 0 | 5 | 0 | 0 | 5 |
| Predose 10 | 0 | 0 | 4 | 0 | 0 | 5 |
| Predose 12 | 0 | 0 | 4 | 0 | 0 | 5 |
| Necropsy (24 hr after last dose) | 0 | 0 | 3 | 0 | 0 | 2 |
| Mid Recovery | 0 | NA | 1 | 0 | 0 | 3 |
| Recovery Necropsy | 0 | 0 | 4 | 0 | 0 | 4 |
| Group 3: 1.8 mg | | | | | | |
| Surgery | 0 | 0 | 7 | 0 | 0 | 8 |
| Predose 2 | 0 | 0 | 7 | 0 | 0 | 6 |
| Predose 4 | 0 | 0 | 6 | 41 | 101 | 6 |
| Predose 6 | 685 | 1317 | 4 | 632 | 1413 | 5 |
| Predose 8 | 2238 | 2596 | 4 | 2180 | 4875 | 5 |
| Predose 10 | 3393 | 5038 | 4 | 5560 | 12433 | 5 |
| Predose 12 | 6436 | 8266 | 4 | 12700 | 28398 | 5 |
| Necropsy (24 hr after last dose) | 14848 | 12401 | 4 | 21442 | 32382 | 4 |
| Mid Recovery | 29307 | 40617 | 3 | 18700 | 283 | 2 |
| Recovery Necropsy | 21060 | 30010 | 3 | 13078 | 7181 | 4 |
| Group 4: 6.0 mg | | | | | | |
| Surgery | 0 | 0 | 7 | 0 | 0 | 8 |
| Predose 2 | 0 | 0 | 7 | 0 | 0 | 6 |
| Predose 4 | 99 | 172 | 7 | 84 | 187 | 5 |
| Predose 6 | 1117 | 1862 | 8 | 1473 | 2775 | 6 |
| Predose 8 | 3987 | 5580 | 5 | 20824 | 27320 | 4 |
| Predose 10 | 6600 | 9679 | 5 | 2715 | 1237 | 2 |
| Predose 12 | 5285 | 7279 | 5 | 955 | 1237 | 2 |
| Necropsy (24 hr after last dose) | 16870 | 16350 | 4 | 63000 | 63000 | 3 |
| Mid Recovery | 66233 | 42238 | 3 | 16800 | NA | 1 |
| Recovery Necropsy | 53600 | 14388 | 3 | 28880 | 29890 | 4 |
| Group 5: 18.6 mg | | | | | | |
| Surgery | 0 | 0 | 7 | 0 | 0 | 6 |
| Predose 2 | 0 | 0 | 7 | 0 | 0 | 8 |
| Predose 4 | 102 | 192 | 7 | 0 | 0 | 6 |
| Predose 6 | 233 | 351 | 7 | 1506 | 3234 | 6 |
| Predose 8 | 3378 | 5931 | 7 | 6367 | 9865 | 6 |
| Predose 10 | 16327 | 24035 | 7 | 19567 | 27542 | 6 |
| Predose 12 | 11596 | 16406 | 5 | 15143 | 24351 | 6 |
| Necropsy (24 hr after last dose) | 5168 | 7427 | 4 | 12135 | 10341 | 4 |
| Mid Recovery | 54700 | 26439 | 3 | 46315 | 62770 | 2 |
| Recovery Necropsy | 50725 | 29217 | 4 | 37790 | 35967 | 4 |

TABLE 37

Serum and CSF Concentrations of rhASA, Male and Female Combined (ng/mL)

| | Serum rhASA (ng/mL) Group in total | | | CSF rhASA (ng/mL) Group in total | | |
|---|---|---|---|---|---|---|
| Time point | Mean ng/mL | SD ng/mL | n | Mean ng/mL | SD ng/mL | n |
| Group 1: Vehicle control | | | | | | |
| Prior to Dose 2 | 0 | 0 | 8 | 0 | 0 | 8 |
| Post Dose 2 | 0 | 0 | 8 | 0 | 0 | 8 |
| Prior to Dose 4 | 0 | 0 | 8 | 0 | 0 | 8 |
| Post Dose 4 | 0 | 0 | 8 | 0 | 0 | 8 |
| Prior to Dose 6 | 0 | 0 | 8 | 0 | 0 | 8 |
| Post Dose 6 | 0 | 0 | 8 | 0 | 0 | 8 |
| Prior to Dose 8 | 0 | 0 | 8 | 0 | 0 | 8 |
| Post Dose 8 | 0 | 0 | 8 | 0 | 0 | 8 |
| Prior to Dose 10 | 0 | 0 | 8 | 0 | 0 | 8 |
| Post Dose 10 | 0 | 0 | 8 | 0 | 0 | 7 |
| Prior to Dose 12 | 0 | 0 | 8 | 0 | 0 | 7 |
| Post Dose 12 | 0 | 0 | 8 | 0 | 0 | 7 |
| Mid Recovery | 0 | 0 | 8 | 0 | 0 | 7 |
| Recovery Necropsy | 0 | 0 | 8 | 0 | 0 | 8 |
| Group 2: 0 mg | | | | | | |
| Prior to Dose 2 | 0 | 0 | 16 | 0 | 0 | 13 |
| Post Dose 2 | 0 | 0 | 16 | 0 | 0 | 12 |
| Prior to Dose 4 | 0 | 0 | 16 | 0 | 0 | 11 |
| Post Dose 4 | 0 | 0 | 16 | 0 | 0 | 10 |
| Prior to Dose 6 | 0 | 0 | 15 | 0 | 0 | 10 |
| Post Dose 6 | 0 | 0 | 15 | 0 | 0 | 10 |
| Prior to Dose 8 | 0 | 0 | 15 | 0 | 0 | 10 |
| Post Dose 8 | 0 | 0 | 15 | 0 | 0 | 10 |
| Prior to Dose 10 | 0 | 0 | 15 | 0 | 0 | 9 |
| Post Dose 10 | 0 | 0 | 15 | 0 | 0 | 9 |
| Prior to Dose 12 | 0 | 0 | 15 | 0 | 0 | 9 |
| Post Dose 12 (Prior to 6-month Necropsy) | 0 | 0 | 15 | 0 | 0 | 10 |
| Mid Recovery | 0 | 0 | 8 | 0 | 0 | 5 |
| Recovery Necropsy | 0 | 0 | 8 | 0 | 0 | 8 |
| Group 3: 1.8 mg | | | | | | |
| Prior to Dose 2 | 0 | 0 | 16 | 42365 | 51844 | 13 |
| Post Dose 2 | 44.7 | 37.3 | 16 | 109654 | 45639 | 13 |
| Prior to Dose 4 | 0 | 0 | 16 | 34247 | 36982 | 12 |
| Post Dose 4 | 0 | 0 | 16 | 122592 | 47311 | 12 |
| Prior to Dose 6 | 0 | 0 | 16 | 43250 | 40831 | 10 |
| Post Dose 6 | 0 | 0 | 16 | 100167 | 27992 | 9 |
| Prior to Dose 8 | 0 | 0 | 16 | 43736 | 40298 | 9 |
| Post Dose 8 | 0 | 0 | 16 | 132333 | 53926 | 9 |
| Prior to Dose 10 | 0 | 0 | 16 | 28401 | 28890 | 9 |
| Post Dose 10 | 0 | 0 | 16 | 98433 | 37220 | 9 |
| Prior to Dose 12 | 0 | 0 | 16 | 59209 | 58253 | 9 |
| Post Dose 12 (Prior to 6-month Necropsy) | 0 | 0 | 16 | 39092 | 42786 | 13 |
| Mid Recovery | 0 | 0 | 8 | 0 | 0 | 5 |
| Recovery Necropsy | 0 | 0 | 8 | 0 | 0 | 8 |
| Group 4: 6.0 mg | | | | | | |
| Prior to Dose 2 | 0 | 0 | 16 | 105964 | 157408 | 14 |
| Post Dose 2 | 158.4 | 78.7 | 16 | 320429 | 153832 | 14 |
| Prior to Dose 4 | 0 | 0 | 16 | 56226 | 72638 | 13 |
| Post Dose 4 | 40.6 | 91.7 | 16 | 341936 | 203284 | 14 |
| Prior to Dose 6 | 0 | 0 | 16 | 86139 | 113563 | 14 |
| Post Dose 6 | 0 | 0 | 16 | 393800 | 206033 | 10 |
| Prior to Dose 8 | 0 | 0 | 16 | 42009 | 65286 | 9 |
| Post Dose 8 | 0 | 0 | 16 | 334333 | 169995 | 9 |
| Prior to Dose 10 | 0 | 0 | 16 | 106452 | 130375 | 7 |
| Post Dose 10 | 0 | 0 | 16 | 364429 | 160707 | 7 |
| Prior to Dose 12 | 0 | 0 | 16 | 70344 | 87227 | 7 |
| Post Dose 12 (Prior to 6-month Necropsy) | 0 | 0 | 16 | 111707 | 151129 | 11 |
| Mid Recovery | 0 | 0 | 8 | 0 | 0 | 4 |
| Recovery Necropsy | 0 | 0 | 8 | 0 | 0 | 8 |

TABLE 37-continued

Serum and CSF Concentrations of rhASA,
Male and Female Combined (ng/mL)

| Time point | Serum rhASA (ng/mL) Group in total | | | CSF rhASA (ng/mL) Group in total | | |
|---|---|---|---|---|---|---|
| | Mean ng/mL | SD ng/mL | n | Mean ng/mL | SD ng/mL | n |
| Group 5: 18.6 mg | | | | | | |
| Prior to Dose 2 | 0 | 0 | 16 | 242676 | 264338 | 15 |
| Post Dose 2 | 455.1 | 257.8 | 16 | 827286 | 378379 | 14 |
| Prior to Dose 4 | 0 | 0 | 16 | 159311 | 191264 | 13 |
| Post Dose 4 | 138.8 | 213.7 | 16 | 975769 | 488021 | 13 |
| Prior to Dose 6 | 0 | 0 | 16 | 276279 | 231010 | 13 |
| Post Dose 6 | 54.5 | 93.8 | 16 | 994385 | 453568 | 13 |
| Prior to Dose 8 | 0 | 0 | 16 | 193064 | 213058 | 13 |
| Post Dose 8 | 27.0 | 67.1 | 16 | 997750 | 531567 | 12 |
| Prior to Dose 10 | 0 | 0 | 16 | 172866 | 228817 | 13 |
| Post Dose 10 | 3.2 | 13 | 16 | 913167 | 319975 | 12 |
| Prior to Dose 12 | 0 | 0 | 16 | 299538 | 365275 | 11 |
| Post Dose 12 (Prior to 6-month Necropsy) | 0 | 0 | 16 | 273348 | 349718 | 13 |
| Mid Recovery | 0 | 0 | 8 | 0 | 0 | 5 |
| Recovery Necropsy | 0 | 0 | 8 | 0 | 0 | 8 |

TABLE 38

Serum and CSF Anti-rhASA Antibody,
Male and Female Combined (ng/mL)

| Time Point | Serum Anti-rhASA Antibody (ng/mL) Group in total | | | CSF Anti-rhASA Antibody (ng/mL) Group in total | | |
|---|---|---|---|---|---|---|
| | Mean ng/mL | SD ng/mL | n | Mean ng/mL | SD ng/mL | n |
| Group 1: Vehicle control | | | | | | |
| Surgery | | | | 0 | 0 | 8 |
| Predose 2 | 0 | 0 | 8 | 0 | 0 | 8 |
| Predose 4 | 0 | 0 | 8 | 0 | 0 | 8 |
| Predose 6 | 0 | 0 | 8 | 0 | 0 | 8 |
| Predose 8 | 0 | 0 | 8 | 0 | 0 | 8 |
| Predose 10 | 0 | 0 | 8 | 0 | 0 | 8 |
| Predose 12 | 0 | 0 | 8 | 0 | 0 | 7 |
| Mid Recovery | 0 | 0 | 8 | 0 | 0 | 7 |
| Recovery Necropsy | 0 | 0 | 8 | 0 | 0 | 8 |
| Group 2: 0 mg | | | | | | |
| Surgery | | | | 0 | 0 | 13 |
| Predose 2 | 0 | 0 | 16 | 0 | 0 | 13 |
| Predose 4 | 0 | 0 | 16 | 0 | 0 | 11 |
| Predose 6 | 0 | 0 | 15 | 0 | 0 | 10 |
| Predose 8 | 0 | 0 | 15 | 0 | 0 | 10 |
| Predose 10 | 0 | 0 | 15 | 0 | 0 | 9 |
| Predose 12 | 0 | 0 | 15 | 0 | 0 | 9 |
| Necropsy (24 hr after last dose) | 0 | 0 | 8 | 0 | 0 | 5 |
| Mid Recovery | 0 | 0 | 8 | 0 | 0 | 4 |
| Recovery Necropsy | 0 | 0 | 8 | 0 | 0 | 8 |
| Group 3: 1.8 mg | | | | | | |
| Surgery | | | | 0 | 0 | 15 |
| Predose 2 | 0 | 0 | 16 | 0 | 0 | 13 |
| Predose 4 | 23028 | 29871 | 16 | 21 | 72 | 12 |
| Predose 6 | 80769 | 70467 | 16 | 656 | 1284 | 9 |
| Predose 8 | 142031 | 93979 | 16 | 2206 | 3796 | 9 |
| Predose 10 | 341506 | 436656 | 16 | 4597 | 9386 | 9 |
| Predose 12 | 511938 | 635340 | 16 | 9916 | 20970 | 9 |
| Necropsy (24 hr after last dose) | 497588 | 666122 | 8 | 18145 | 22972 | 8 |
| Mid Recovery | 358213 | 226397 | 8 | 25064 | 29302 | 5 |
| Recovery Necropsy | 504013 | 766860 | 8 | 16499 | 18552 | 7 |
| Group 4: 6.0 mg | | | | | | |
| Surgery | | | | 0 | 0 | 15 |
| Predose 2 | 0 | 0 | 16 | 0 | 0 | 13 |
| Predose 4 | 47209 | 66899 | 16 | 93 | 170 | 12 |
| Predose 6 | 167721 | 137276 | 16 | 1269 | 2205 | 14 |
| Predose 8 | 315800 | 201572 | 16 | 11470 | 19344 | 9 |
| Predose 10 | 750656 | 682110 | 16 | 5490 | 8143 | 7 |
| Predose 12 | 1003450 | 868860 | 16 | 4048 | 6328 | 7 |
| Necropsy (24 hr after last dose) | 880534 | 857199 | 8 | 36640 | 45439 | 7 |
| Mid Recovery | 1270750 | 938646 | 8 | 53875 | 42430 | 4 |
| Recovery Necropsy | 953125 | 763122 | 8 | 39474 | 26274 | 7 |
| Group 5: 18.6 mg | | | | | | |
| Surgery | | | | 0 | 0 | 13 |
| Predose 2 | 0 | 0 | 16 | 0 | 0 | 15 |
| Predose 4 | 48433 | 46054 | 16 | 55 | 146 | 13 |
| Predose 6 | 252450 | 224723 | 16 | 821 | 2204 | 13 |
| Predose 8 | 441119 | 310702 | 16 | 4757 | 7781 | 13 |
| Predose 10 | 936813 | 849893 | 16 | 17822 | 24652 | 13 |
| Predose 12 | 1380250 | 1331905 | 16 | 13531 | 20189 | 11 |
| Necropsy (24 hr after last dose) | 286150 | 238760 | 8 | 8652 | 9129 | 8 |
| Mid Recovery | 2492875 | 1686472 | 8 | 51346 | 36819 | 5 |
| Recovery Necropsy | 2005125 | 1347857 | 8 | 44258 | 31114 | 8 |

TABLE 39

INCIDENCE OF ANTI-RHASA ANTIBODIES AT NECROPSY

| | Serum Antibody-Positive Animals (positive/total tested) | | | | CSF Antibody-Positive Animals (positive/total tested) | | | |
|---|---|---|---|---|---|---|---|---|
| | M | | F | | M | | F | |
| Group | 6-month Necropsy | Recovery Necropsy | 6-month Necropsy | Recovery Necropsy | 6-month Necropsy | Recovery Necropsy | 6-month Necropsy | Recovery Necropsy |
| 1 (DC) | NA | 0/4 | NA | 0/4 | NA | 0/4 | NA | 0/4 |
| 2 (vehicle) | 0/4 | 0/4 | 0/4 | 0/4 | 0/3 | 0/4 | 0/2 | 0/4 |

TABLE 39-continued

INCIDENCE OF ANTI-RHASA ANTIBODIES AT NECROPSY

| | Serum Antibody-Positive Animals (positive/total tested) | | | | CSF Antibody-Positive Animals (positive/total tested) | | | |
|---|---|---|---|---|---|---|---|---|
| | M | | F | | M | | F | |
| Group | 6-month Necropsy | Recovery Necropsy | 6-month Necropsy | Recovery Necropsy | 6-month Necropsy | Recovery Necropsy | 6-month Necropsy | Recovery Necropsy |
| 3 (1.8 mg IT) | 4/4 | 4/4 | 4/4 | 4/4 | 4/4 | 3/3 | 3/4 | 4/4 |
| 4 (6.0 mg IT) | 4/4 | 4/4 | 4/4 | 4/4 | 4/4 | 3/3 | 2/3 | 4/4 |
| 5 (18.6 mg IT) | 4/4 | 4/4 | 4/4 | 4/4 | 3/4 | 4/4 | 4/4 | 4/4 |

The quantitation limit for rhASA in cynomolgus monkey serum is 39.1 ng/mL, and all serum samples from Groups 1 and 2 were below quantitation limit (BQL), see Table 33. Serum levels of rhASA were tested prior to and at 24 hours after Doses 2, 4, 6, 8, 10, and 12 (6-month necropsy), midway through the recovery period, and prior to the recovery necropsy. rhASA levels were undetectable in Group 3 (1.8 mg/dose), Group 4 (6.0 mg/dose), and Group 5 (18.6 mg/dose) prior to Doses 2, 4, 6, 8, 10, and 12, After Dose 12, midway through the recovery period, and prior to the recovery necropsy. After Dose 2, the levels of rhASA in serum were dose-related. After Dose 4 (Group 3), Dose 6 (Groups 3 and 4), and Doses 8 and 10 (Groups 3 and 4 and Group 5 males), rhASA levels were undetectable. Serum levels of rhASA declined in Group 4 (6.0 mg/dose) after Dose 4 and in Group 5 (18.6 mg/dose) after Doses 4 and 6 for males and Doses 4, 6, 8, and 10 for females. This apparent decline in serum rhASA levels may be related to the increasing concentration of anti-rhASA antibodies. There were no apparent sex differences in serum levels of rhASA, given the sample variability and small group numbers in this study.

The quantitation limit for rhASA in cynomolgus monkey CSF is 19.5 ng/mL, and all CSF samples from Groups 1 and 2 were BQL, see Table 34. rhASA was detectable in CSF prior to and after Doses 2, 4, 6, 8, 10, and 12 (6-month necropsy) in all dosed groups. The levels were higher postdose (approximately 24 hours postdose) and were dose related. The levels in CSF were much greater than those in serum. There were no apparent sex differences in CSF levels of rhASA, given the sample variability and small group numbers in this study. rhASA was not detectable midway through the recovery period and prior to the recovery necropsy in all dosed groups. CSF levels at the Dose 12 (necropsy) collections for rhASA treated groups were lower than levels postdose 8 and 11. Potential reasons for lower rhASA levels at necropsy include the larger volume taken (~2.25 mL total for cell counts, chemistry, rhASA and anti-rhASA antibody) at necropsy vs. those taken at in-life dosing interval (up to 0.5 mL pre- or postdose for rhASA concentration). Additionally, some animals did not have patent catheters at necropsy, and samples were taken via a CM tap rather than via the catheter. This route consistently yielded lower rhASA concentrations as compared with sampling via the catheter. This is likely due to the limited rostrocaudal direction of CSF bulk flow that is acknowledged to occur in vertically-oriented animals like monkeys and man (e.g., it is well known that constituents of CSF exhibit marked rostrocaudal gradients throughout an individual's lifetime).

Anti-rhASA antibodies in serum were detected in every animal treated with rhASA at some time point, see Table 35. Animals are defined as positive for anti-rhASA antibodies if the level of anti-rhASA antibody was above the quantitation limit (78.1 ng/mL). Animals remained positive for anti-rhASA antibodies once they seroconverted. No animals were positive for anti-rhASA antibodies at the predose 2 timepoint. All rhASA animals except Male No. 026 (Group 4; 6.0 mg/dose) were positive for serum anti-rhASA antibodies at the predose 4 timepoint. Male No. 026 was positive for serum antiboday at the predose 6 timepoint. In Group 5 (18.6 mg/kg), the necropsy antibody samples had lower antibody levels. This apparent decrease may be due to the presence of rhASA interfering with the assay. The titer was generally higher in the mid- and high-dose groups (6.0 and 18.6 mg/dose) than the low dose animals (1.8 mg/dose). The presence of anti-rhASA antibodies is an expected result from treating cynomolgus monkeys with a recombinant human protein'. Given the variability in the results, there was no apparent sex differences.

All animals with detectable anti-rhASA antibodies in CSF had detectable rhASA antibodies in serum as well, with the exception of Female Nos. 049 (Group 3; 1.8 mg/dose) and 057 (Group 4; 6.0 mg/dose). The variability in the antibody concentration and incidence precludes determination of a dose response. Animals are defined as positive for anti-rhASA antibodies if the level of anti-rhASA antibody was above the quantitation limit (78.1 ng/mL)

Combined values for males and females for serum and CSF rhASA levels and for anti-rhASA antibodies are shown in Table 36 and Table 37. Combined male and female results are similar to the individual sexes, discussed above.

Example 6—Efficacy

In this example, 11 Wild-type control (mASA+/+ hASA −/−) mice were assigned to Group A and received no treatment. thirty-four (34) hASAC69S/ASA −/− mice were assigned to each of 5 dose groups and received vehicle (Group B) or rhASA (rhASA) at doses of 20 mg/kg (intravenous [IV]; Group C) or 0.04, 0.12, and 0.21 mg (Groups D, E, and F, respectively) on Days 1, 9, 15/16, and 22. All IV doses were administered via a tail vein. All intrathecal (IT) doses were administered as an infusion in a volume of 12 µL at an approximate range of 2 µL/20 seconds (Table 40).

TABLE 40

STUDY DESIGN

| Group | No. of Animals | Animal Type | Treatment | Dose | Route | Total No. of Injections | Sacrifice | Dose in mg/kg brain weight[a] |
|---|---|---|---|---|---|---|---|---|
| A | 11 | Wild-type control (mASA +/+ hASA −/−) | None | NA | NA | NA | NA | NA |
| B | 9 | hASAC69S/ ASA −/− | Vehicle Control | Vehicle | IT lumbar | 4 (Days 1, 9, 15/16[b], and 22) | 24 hours after the fourth dose | 0 |
| C | 5 | | rhASA | 20 mg/kg | IV (tail vein) | | | NA |
| D | 5 | | rhASA | 0.04 mg | IT lumbar | | | 100 |
| E | 5 | | rhASA | 0.12 mg | IT lumbar | | | 300 |
| F | 10 | | rhASA | 0.21 mg | IT lumbar | | | 520 |

NA = not applicable;
IT = intrathecal;
IV = intravenous.
[a]Brain weight for mice is approximately 0.0004 kg.
[b]Groups C, D, and E were dosed on Day 15; Groups B and E were dosed on Day 16.

The ASA knockout mouse hASAC69S/ASA(−/−) is an accepted model of MLD, and has been used to test potential treatments for this disease. The intrathecal route is the intended route of administration in humans. The intravenous route of administration has been tested for this compound and a similar compound in MLD mice. An intravenous control group has been added as a positive control for histological changes expected in peripheral organs. Animals received 100, 300, or 520 mg/kg of brain weight (0.04, 0.12, 0.21 mg, respectively) of rhASA. The dose levels normalized to brain weight selected for this study correspond to doses that are planned for use in humans or have been used in toxicology studies or in previous efficacy models of lysosomal storage diseases. These doses were not expected to have any toxicity.

Receipt

| | |
|---|---|
| Species | Mice (*Mus musculus*) |
| Strain | hASAC69S/ASA (−/−) mice and wild type controls |
| Age | Approximately 14-17 months at arrival |
| No. of Groups | 6 |
| No. of Animals | 34 ASA knockout mice + 11 wild type controls |

Following arrival, each animal was examined to assess health status.

Housing

Animals were group housed in high-temp polycarbonate filter-top cages, with CareFresh paper bedding and water bottles. Each cage was clearly labeled with a cage card indicating project, group and animal numbers, and sex. Each animal was uniquely identified using an ear punch system. Animals were treated in compliance with federal guidelines. The targeted conditions for animal room environment and photoperiod were as follows:

| | |
|---|---|
| Temperature | 22° C. ± 3° C. |
| Humidity | 50% ± 20% |
| Light cycle | 12 hours light and 12 hours dark |

During and following the dose administration, the photoperiod may have been temporarily interrupted for scheduled activities. Such interruptions are not considered to affect the outcome or quality of this research.

All available wild type animals (11) were assigned to Group A and were numbered 35 through 45. ASA (−/−) hASA (+/−) animals were assigned consecutive numbers (1 through 34) as they were removed from their cages, weighed, and ear punched during acclimation. Animals were then assigned to the treatment groups using Research Randomizer (www.randomizer.org) on Jan. 3, 2011. the first 9 numbers were assigned to Group B, the next 5 to Group C, the next 5 to Group D, the next 5 to Group E, and the final 10 to Group F. Animals were assigned as follows in Table 41:

TABLE 41

ANIMAL ASSIGNMENT

| Group | N | Animal Numbers |
|---|---|---|
| A | 11 | 35, 36, 37, 38, 39, 40, 41, 42, 43, 44, 45 |
| B | 9 | 7, 13, 17, 22, 23, 24, 28, 29, 30 |
| C | 5 | 6, 16, 19[a], 21, 32 |
| D | 5 | 5, 9, 14, 18, 27 |
| E | 5 | 1, 2, 4, 8, 11 |
| F | 10 | 3[b], 10, 12, 15, 20, 25, 26, 31, 33, 34 |

[a]Animal No. 19 could not be located at the time of dosing.
[b]Animal No. 3 died before dosing began.

Test Article and Vehicle

| Test Article | |
|---|---|
| Identity | rhASA |
| Description | human recombinant Arylsulfatase A (rhASA) |
| Storage Conditions | Approximately 4° C. |

| Vehicle | |
|---|---|
| Identity | rhASA Vehicle (154 mM NaCl, 0.005% polysorbate 20, pH ~6.0) |
| Storage Condition | Approximately 4° C. |

Preparation of Vehicle

The vehicle was used as provided. The vehicle was warmed on the bench top (ambient). Once the vehicle was warmed, the material was mixed by gently swirling and inverting. The bottles were not vortexed or shaken. The bottle was dried before accessing the material. Any remaining vehicle was returned to the refrigerator (1° C.-8° C.).

Dose Formulation Preparation rhASA was diluted with vehicle to achieve the necessary concentrations. The test article was warmed on the bench top (ambient). Once the test article was warmed, the material was mixed by gently swirling and inverting. The bottles were not vortexed or shaken.

Dyes to Track Injections:

An infrared dye (such as IRDye®, LI-COR Biosciences, Lincoln, Nebr.) was utilized for tracking the injections. Dyes such as this have been used in intrathecal injections as a survival procedure after intrathecal administration. The dye was mixed with the test article before administration; 1 nmole of dye in 1 μL was added to the test article. In addition to the infrared dye, 1 μL of FD&C blue #1 (0.25%) was used for tracking injections. This blue dye is a common food additive and is generally considered safe and non-toxic.

Lumbosacral IT Injection of rhASA or Vehicle

Animals in Groups B, D, E, and F received intrathecal injections on Days 1, 9, 15 or 16, and 22.

Adult mice were anesthetized using 1.25% 2,2,2 tribromoethanol (Avertin) at 200-300 μL/10 grams body weight (250-350 mg/kg) by intraperitoneal injection. Dorsal hair was removed between the base of the tail and the shoulder blades using a clippers. The shaved area was cleaned with povidine/betadine scrub followed by isopropyl alcohol. A small midline skin incision (1-2 cm) was made over the lumbosacral spine, and the intersection of the dorsal midline and the cranial aspect of the wings of the ilea (singular ileum) was identified. The muscle in the iliac fossa (gluteus medius) is a heart shaped muscle. The two sides of the top of the "heart" approximate the location of the wings of the ilea. A 32-gauge needle attached to a gas tight 10-20 μL glass Hamilton syringe was inserted until resistance was felt from the underlying bone. Injection of 10 μL of test article, 1 μL of infrared dye, and 1 μL of FD&C blue #1 (total injection volume of 12 μL) was performed at an approximate rate of 2 μL/20 seconds (12 μL/2 minutes). The skin incision was closed using wound clips. The success of the injection was judged by imaging to determine if the infrared dye had distributed throughout the CNS, as well as the visible blue dye. After imaging, the animal was allowed to recover in a recovery chamber.

Intravenous Injection of rhASA

Animals in Group C received intravenous injections on Days 1, 9, 15, and 22.

For IV injections, animals were anesthetized using isoflurane, if required, and were placed in a restrainer. The tail vein was dilated by warming by flicking the tail gently with the finger. The injection site was then wiped with 70% ethanol. Alternatively, the animal was placed in a warm chamber (40° C.) for 1-1.5 minutes. A 28- to 30-gauge needle was used to inject test material. The volume of injection was 5-10 mL/kg.

Approximately 24 hours after the fourth dose, animals in Groups B-F were euthanized. Animals were subjected to different tissue collection procedures, as detailed below. Animals in Group A were not treated; however, they were euthanized on Jan. 27 or 28, 2011 and subjected to tissue collection procedures, as detailed below.

Serum (All Animals)

A terminal blood sample (approximately 0.5 mL) was collected from all animals (Groups A-F) via retroorbital puncture under isoflurane anesthesia. A glass tube was placed in the orbit, gently penetrating the area behind the eye and thus disrupting the venous drainage located behind the eye. Blood was collected by capillary action and/or gravity flow. Following blood collection, pressure was applied to the orbit to stop the bleeding.

The whole blood samples were processed to serum and frozen at <−80° C. The serum was stored at −80° C. and analyzed for antibodies.

Tissues for Light Microscopy Investigations (Groups A-F; 5 Mice Per Group)

After blood collection, animals were euthanized via $CO_2$ asphyxiation. A tail snip was collected prior to perfusion and frozen for possible genotyping. The pericardial cavity was exposed. Three (3) mice per group were transcardially perfused with heparinized saline solution (1 U/mL sodium heparin in 0.9% NaCl, sterile-filtered) chilled ice-cold and then with 4% paraformaldehyde at approximately 4° C. The brain was removed, and the abdomen was cut to expose the internal organs further. The brain and carcass were placed in paraformaldehyde, except for the tail snip which was frozen.

Tissues for Lipid Analysis (Groups A, B, and F; 6, 4, and 5 Animals, Respectively)

After blood collection, animals were euthanized via $CO_2$ asphyxiation. A tail snip was collected prior to perfusion and frozen for possible genotyping. The pericardial cavity was exposed. For lipid analyses, 4-6 mice per group were transcardially perfused with heparinized saline solution (1 U/mL sodium heparin in 0.9% NaCl, sterile-filtered) chilled ice-cold. Exemplary tissues collected for lipid analyses are presented in Table 42.

TABLE 42

TISSUES COLLECTED FOR LIPID ANALYSIS
Tissues Collected for Lipid Analysis

| Brain (separated into left and right hemispheres and weighed) | Kidney (2) |
|---|---|
| Spinal cord (removed from spinal column) | |
| Sciatic nerve (2) (dissected free from muscle) | Tail snip (prior to perfusion) |

Upon collection, tissues were weighed and then frozen, either on dry ice or by placing in a −80° C. freezer. The brain was separated into left and right hemispheres. The right is utilized for lipid analysis by MS. The left will be analyzed for possible N-acetyl-L-aspartate (NAA) analysis. Tissues were stored at −80° C. until analysis (see Table 43).

TABLE 43

SAMPLE STORAGE CONDITIONS

Figure 19:
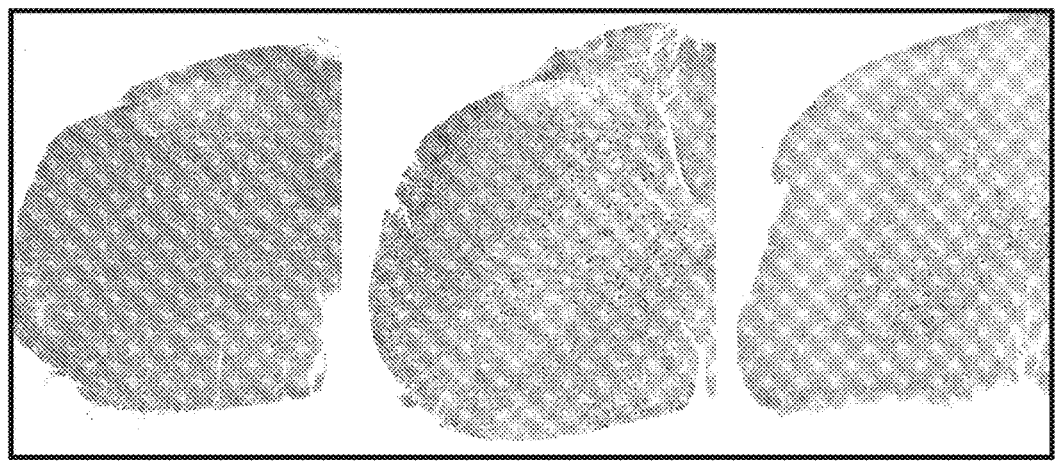
FIG. 19 depicts exemplary Alcian blue staining of spinal cord of immunotolerant MLD mice treated with rhASA depicts exemplary results illustrating sulfatide reduction as determined by Alcian blue staining of the cervical spinal cord in animals that received intrathecal injections of recombinant hASA at days 1, 8, 15 and 22 at doses of 520 mg/kg brain weight or vehicle control. As demonstrated, treatment with intrathecally injected recombinant hASA resulted in reduction of sulfatide accumulation in the cervical spinal cord.
Figure 20:
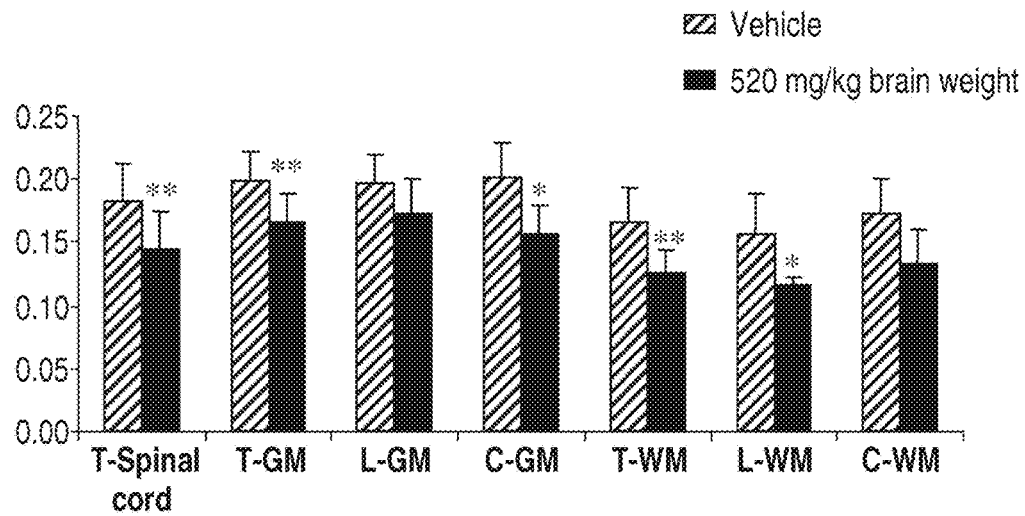
FIG. 20 illustrates exemplary morphometry analysis of Alcian blue stained spinal cord sections from immunotolerant MLD mice treated with rhASA, including exemplary results illustrating optical density of Alcian blue in total spinal cord (T-Spinal Cord), total gray matter (T-GM), lumbar gray matter (L-GM), cervical gray matter (C-GM), total white matter (T-WM), lumbar white matter (L-WM), and cervical white matter (C-WM) as determined by morphometry analysis. As demonstrated, a statistically significant reduction in Alcian blue staining was observed in animals treated with rhASA as compared to a vehicle control.
Figure 21:
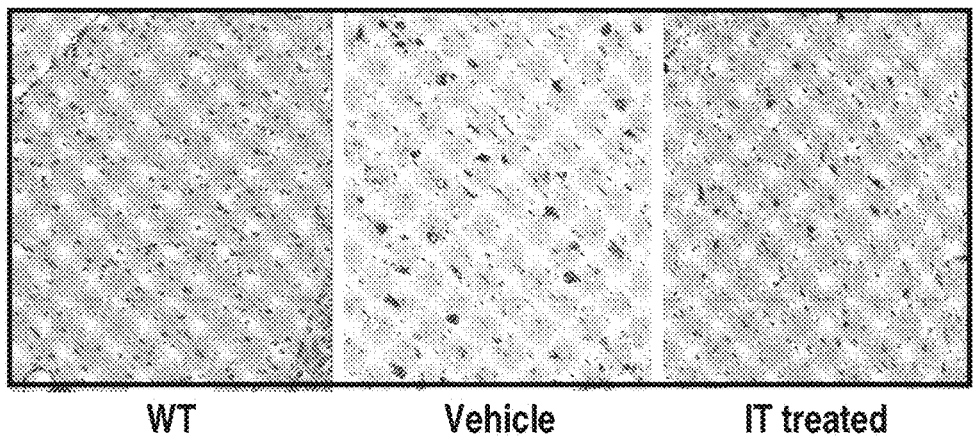
FIG. 21 depicts exemplary reduction of LAMP staining in white matter (fimbria) of immunotolerant MLD mice treated with rhASA depicts exemplary results illustrating LAMP-1 levels in fimbria as determined by immunohistochemistry. Magnification=20x. As demonstrated, treatment with intrathecally injected rhASA resulted in reduction of LAMP-1 in the cerebral white matter.
Figure 22:
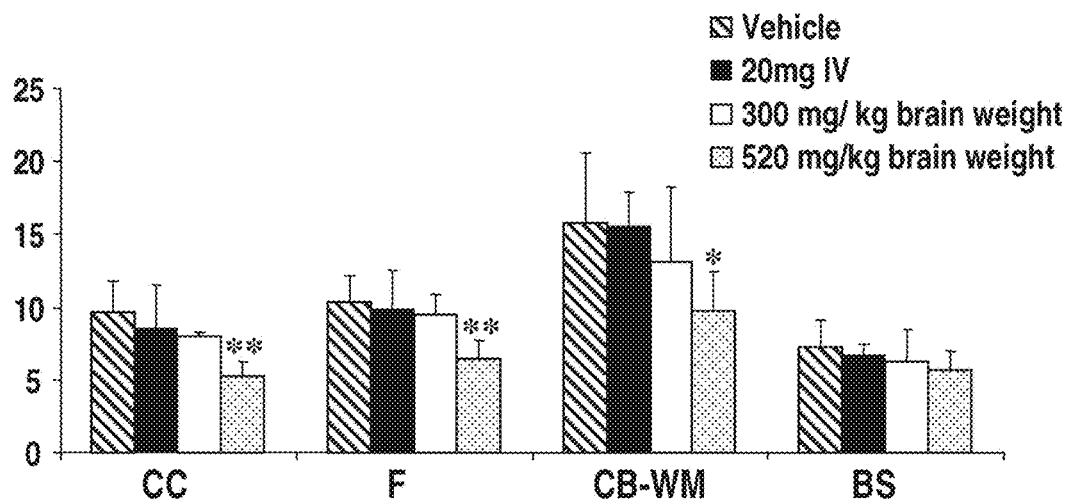
FIG. 22 illustrates exemplary morphometry Analysis of LAMP staining of brain from immunotolerant MLD mice treated with rhASA depicts exemplary results illustrating LAMP-1 staining intensity in corpus collosum (CC), fimbria (F), cerebellar white matter (CB-WM) and brain stem (BS) of animals treated with 20 mg/kg intravenous rhASA, 300 mg/kg brain weight intrathecal rhASA, 520 mg/kg brain weight intravenous rhASA, or vehicle control.

| Type of Sample | Storage Temperature |
|---|---|
| Serum | frozen at circa −80° C. |
| tissues for lipid analysis | frozen at circa −80° C. |
| Tail snips | frozen at circa −80° C. |
| Tissues for light microscopy | Approximately 4° C. | rhASA reduced sulfatide storage in the spinal cord of MLD mice, particularly in the white matter, FIG. 19. Morphometry analysis of the spinal cord demonstrated that the optical density of alcian blue staining was statistically significantly reduced after rhASA dosing, FIG. 20. rhASA treated MLD mice also exhibited reduced lysosomal activity in the brain, FIG. 21. This reduction was statistically significant in the high-dose group (0.21 mg-520 mg/kg brain weight) compared with vehicle treated animals, FIG. 22.

Immunotolerant MLD mice (hASAC69S/ASA(−/−)) over 1 year in age received intrathecal-lumbar administration of rhASA one time each week for 4 weeks (a total of 4 doses). Doses were vehicle (154 mM NaCl, 0.005% polysorbate 20, pH ~6.0), 0.04, 0.12, 0.21 mg/dose (normalized doses were 100, 300 and 520 mg/kg of brain weight, respectively). At terminal timepoints efficacy was evaluated by immunohistochemistry assessment of sulfatide clearance and lysosome activity within the brain and spinal cord. Spinal cord and brain sections were stained using alcian blue stain targeting sulftatides in tissues Brain sections were also stained for the presence of lysosomal-associated membrane protein (LAMP), an indicator of lysosomal processes. Additionally, morphometry analysis was performed on alcian blue and LAMP stained sections of the spinal cord (cervical, thoracic and lumbar) and brain.

These preliminary results demonstrate efficacy of intrathecal lumbar administration of rhASA. Compared to vehicle control mice, rhASA treated MLD mice exhibit evidence of improvement within the histological markers of disease, such as reduced sulfatide storage (noted by alcian blue staining) and lysosomal activity in the brain. These histopathological changes were observed near the site of administration (spinal cord) as well as in the distal portions of the brain.

Example 7—Biodistribution 2

Overview

In this study, 36 male and 36 female juvenile cynomolgus monkeys (<12 months at initiation) were assigned to each of 5 dose groups and received rhASA (rhASA) at doses of 0 (device control; animals were dosed with 0.6 mL of PBS), 0 (vehicle control), 1.8, 6.0, or 18.6 mg (Groups 1, 2, 3, 4, and 5, respectively) every other week for 6 months for a total of 12 doses. All doses were administered as an infusion in a volume of 0.6 mL, followed by a flush of 0.5 mL PBS given over approximately 10 minutes (Table 44Table).

TABLE 44

STUDY DESIGN
Study Design

| Group | No. of Animals | Nominal Dose Concentration (mg/mL) | Administered Dose (mg) | No. of Animals, 6 Month Sacrifice | No. of Animals, 1 Month Recovery Sacrifice |
|---|---|---|---|---|---|
| 1 | 4 M, 4 F | DC | 0 | — | 4 M, 4 F |
| 2 | 8 M, 8 F | 0 | 0 | 4 M, 3 F[a] | 4 M, 4 F |
| 3 | 8 M, 8 F | 3 | 1.8 | 4 M, 4 F | 4 M, 4 F |
| 4 | 8 M, 8 F | 10 | 6.0 | 4 M, 4 F | 4 M, 4 F |
| 5 | 8 M, 8 F | 31 | 18.6 | 4 M, 4 F | 4 M, 4 F |

DC = Device Control; Animals in Group 1 were not dosed with vehicle or test article.
[a]Vehicle Control Animal No. 044 was sacrificed early on Day 50 due to a leaking catheter Material and Methods
Tissue Collection The brains were cut in a brain matrix at 3 mm thick coronal slice thickness. Each brain was sectioned into full coronal slices including: neocortex (including frontal, parietal, temporal, and occipital cortex), paleocortex (olfactory bulbs and/or piriform lobe), basal ganglia (including caudate and putamen), limbic system (including hippocampus and cingulate gyri), thalamus/hypothalamus, midbrain regions (including substantia nigra), cerebellum, pons, and medulla oblongata. The locations from which individual tissue samples were obtained (via 4-mm biopsy punch) are shown in FIGS. 32-37. The images in FIGS. 32-37 are from the University of Wisconsin and Michigan State Comparative Mammalian Brain Collections, (also the National Museum of Health and Medicine). Punch number 22 was not collected, as this structure was not present during necropsy. All brain samples were frozen and stored at −60° C. or below prior to analysis for rhASA using an enzyme-linked immunosorbent assay.

The first brain slice and every second slice thereafter were fixed in formalin for histopathological evaluation and immunohistochemical. The second brain slice and every second slice thereafter were frozen for test article concentration analysis. Prior to freezing, samples of brain were taken from the right portion of the even-numbered, test article analysis brain slices for biodistribution analysis. The location of the brain samples were photographed at necropsy and the brain slice number was recorded. The samples were obtained using either a 4-mm circular punch or cut with a scalpel to optimize the amount of white matter collected. All punches were frozen and stored at −60° C. or below for test article analysis. The remainder of the brain slice was frozen and stored at −60° C. or below for possible test article analysis. Locations of the punches are shown in Appendix B.

The spinal cord (cervical, thoracic and lumbar) was cut into one-centimeter sections. The first slice and every second slice thereafter was fixed in formalin for histopathological and immunohistochemical analysis. The second slice of spinal cord and every second slice thereafter was frozen and stored at −60° C. or lower for test article analysis. The distribution of slices was adjusted so that the slice with the tip of the intrathecal catheter (Slice 0) was fixed in formalin and analyzed for histopathology.

Preparation of Brain, Liver, and Spinal Extracts and Determination of rhASA Concentration Brain punches, spinal cord, and liver samples were analyzed using a validated method in compliance with the United States Food and Drug Administration (FDA) Good Laboratory Practice (GLP) regulations 21 CFR, Part 58 and with applicable Midwest BioResearch standard operating procedures. Tissue samples were homogenized in lysis buffer, centrifuged to remove any tissue debris, and stored at −80° C. until assayed. rhASA concentration in the soluble fractions of the homogenates was determined by an ELISA using polyclonal rabbit antibody SH040 as the capture antibody and HRP (horseradish peroxidase)-conjugated anti-ASA monoclonal antibody 19-16-3 as the detection antibody. After a wash step to remove unbound materials, tetramethylbenzidine (TMB) substrate solution reacted with the peroxide in the presence of HRP-conjugated antibody to produce a colorimetric signal that was proportional to the amount of ASA bound by the anti ASA antibody in the initial step. The resulting amount of rhASA in each tissue homogenate was interpolated from a standard curve.

Samples were also analyzed by a bicinchoninic acid (BCA) protein determination assay to obtain the concentration of protein in an unknown sample. The protein concentration for each sample was determined by interpolation of an albumin standard curve. rhASA concentration results were then normalized to total protein in tissue extracts, as determined by bicinchoninic acid assay.

Figure 32:
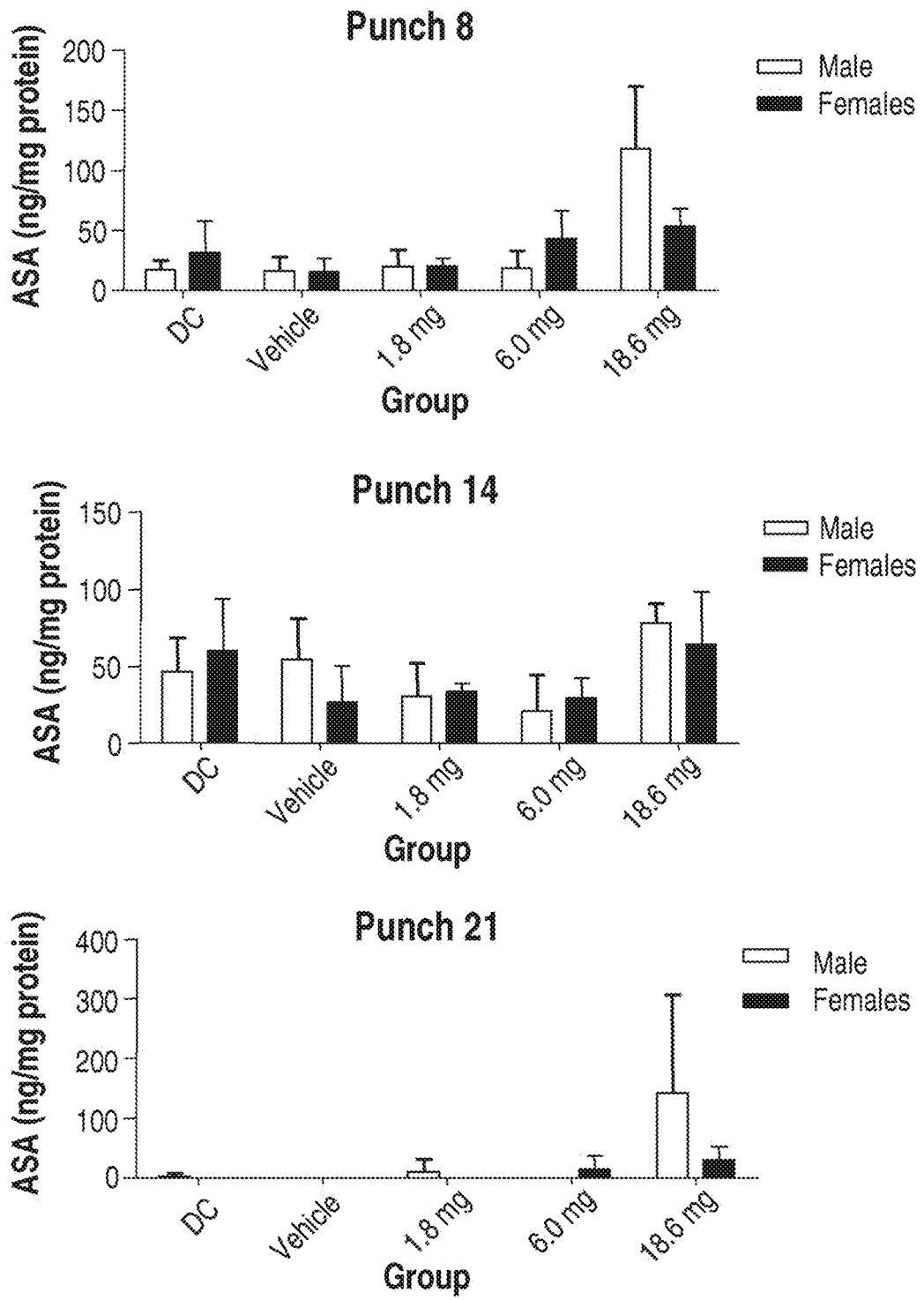
FIG. 32 illustrates exemplary concentration of rhASA in selected punches from surface of brain for device control, vehicle, 1.8 mg, 6.0 mg and 18.6 mg treated animals. (male and female separate, device control data is from recovery necropsy, all other data from main necropsy).
Figure 33:
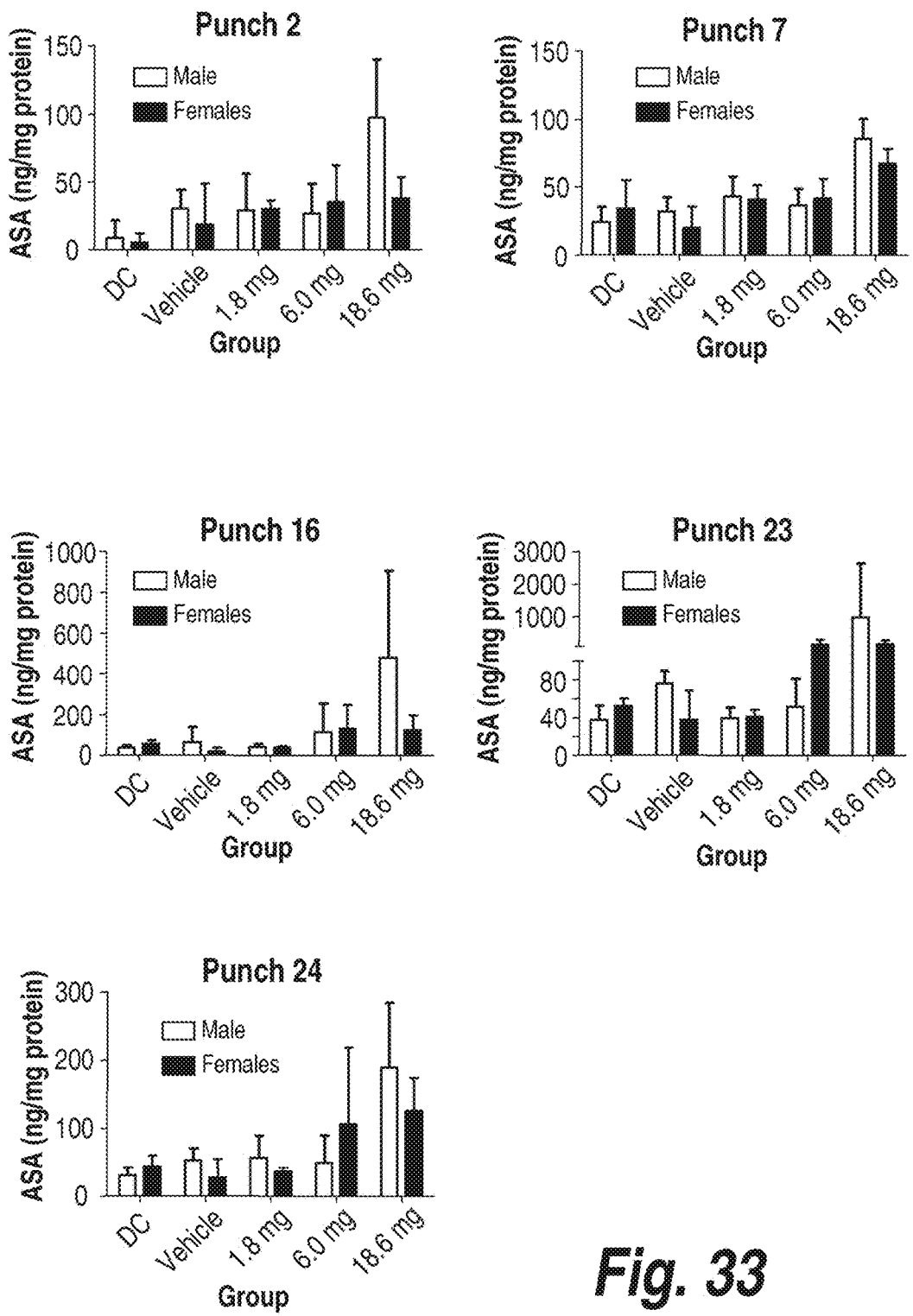
FIG. 33 illustrates exemplary concentration of rhASA in selected punches from deep white area of brain for device control, vehicle, 1.8 mg, 6.0 mg and 18.6 mg treated animals. (male and female separate, device control data is from recovery necropsy, all other data from main necropsy).
Figure 34:
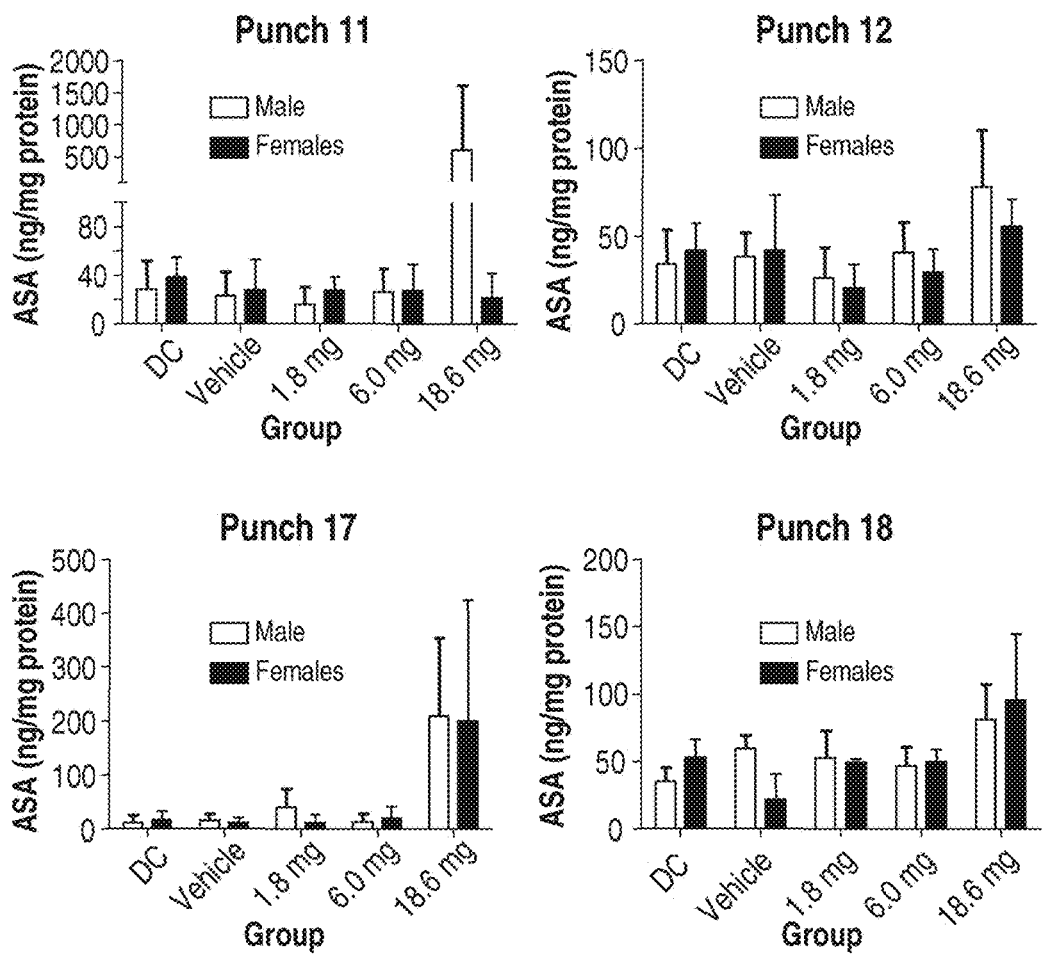
FIG. 34 illustrates exemplary concentration of rhASA in selected punches from deep grey area of brain for device control, vehicle, 1.8 mg, 6.0 mg and 18.6 mg treated animals. (male and female separate, device control data is from recovery necropsy, all other data from main necropsy).
Figure 35:
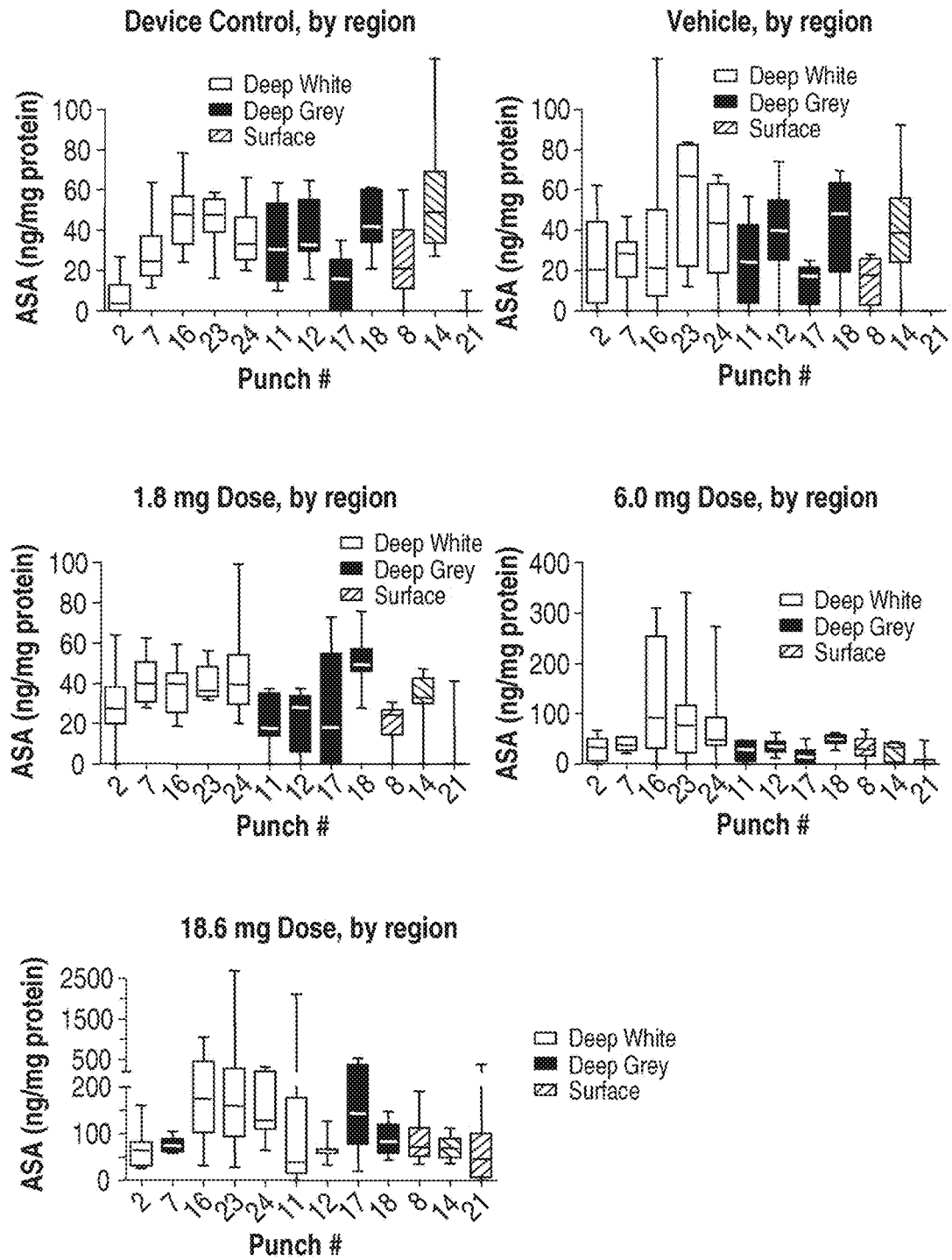
FIG. 35 illustrates exemplary concentration of rhASA in selected punches from various regions in device control, vehicle, 1.8. mg, 6.0 mg and 18.6 mg treated animals. (male and female combined, device control data is from recovery necropsy, all other data from main necropsy).

The ASA levels of all punches for the vehicle, 1.8 mg/dose, 6.0 mg/dose, and 18.6 mg/dose groups are shown in FIG. 23, FIG. 24, FIG. 25, and FIG. 26, respectively. The ASA levels of all punches for the recovery animals for the device control, vehicle, 1.8 mg/dose, 6.0 mg/dose, and 18.6 mg/dose groups are shown in FIG. 27, FIG. 28, FIG. 29, FIG. 30, and FIG. 31, respectively The ASA levels for selected punches that were taken near the surface (meninges) of the brain are shown in FIG. 32. ASA levels for selected punches that are considered to contain mostly deep white brain matter are shown in FIG. 33. White matter is composed of bundles of myelinated nerve cell processes (or axons). Selected punches which contain mostly material from the deep grey brain matter are shown in FIG. 34. Grey matter contains neural cell bodies, in contrast to white matter. The values of ASA in selected punches from the surface, deep white and deep grey are shown for each dose group in FIG. 35.

Figure 36:
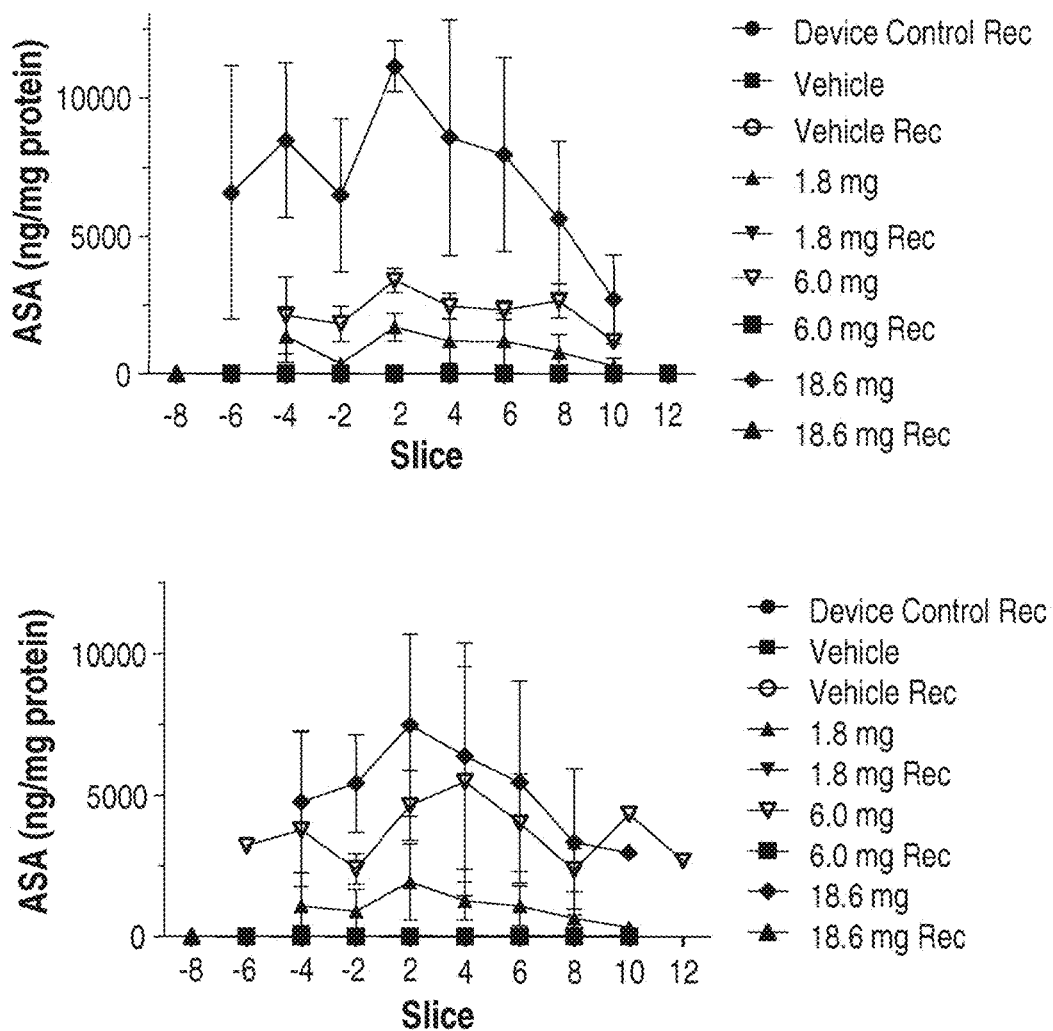
FIG. 36 illustrates exemplary concentration of rhASA in spinal cord sections of juvenile cynomolgus monkeys following EOW IT dosing for 6-months—recovery necroscopy.

Spinal cord concentration data is shown in FIG. 36.

Figure 37:
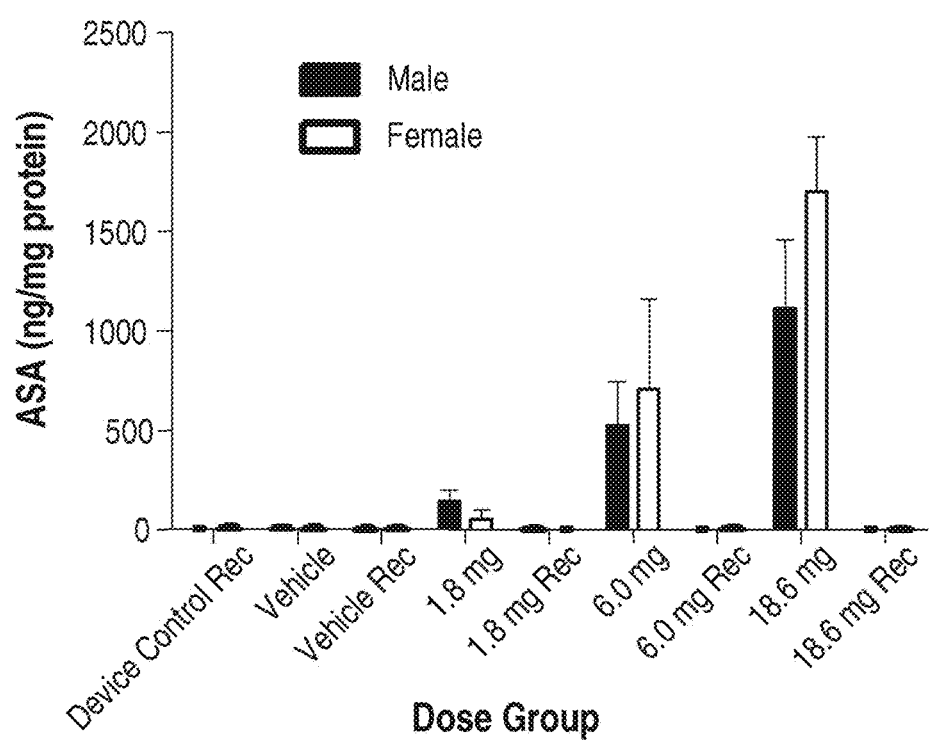
FIG. 37 illustrates exemplary concentration of rhASA in liver of juvenile cynomolgus monkeys following EOW IT dosing for 6-months—recovery necroscopy.
Figure 38:
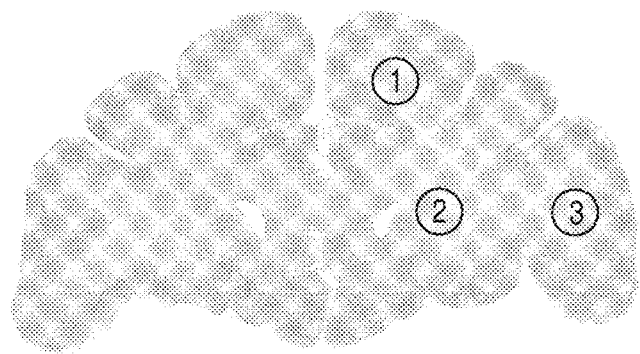
FIG. 38 illustrates exemplary anatomical locations of certain brain punches.
Figure 39:
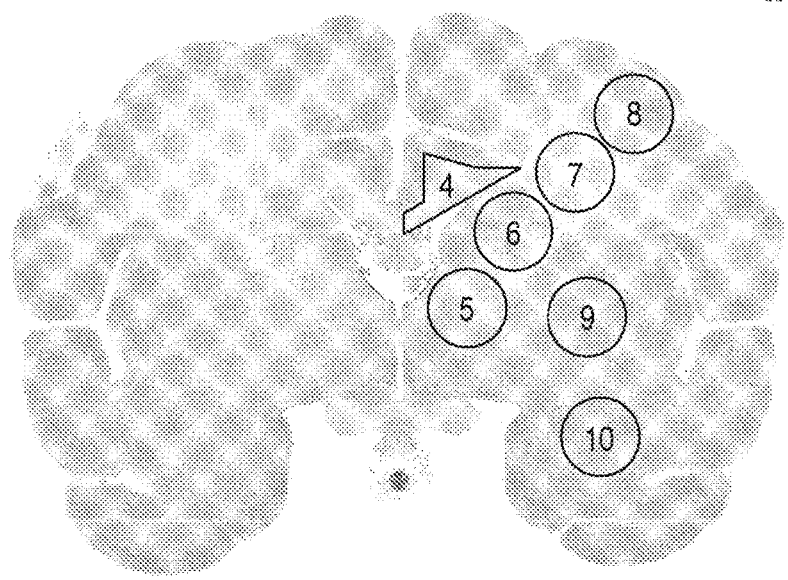
FIG. 39 illustrates exemplary anatomical locations of certain brain punches.
Figure 40:
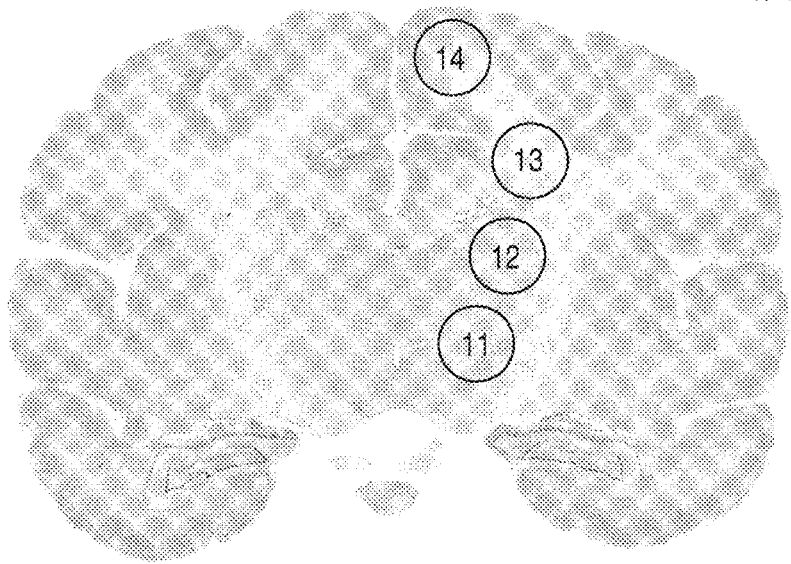
FIG. 40 illustrates exemplary anatomical locations of certain brain punches.
Figure 41:
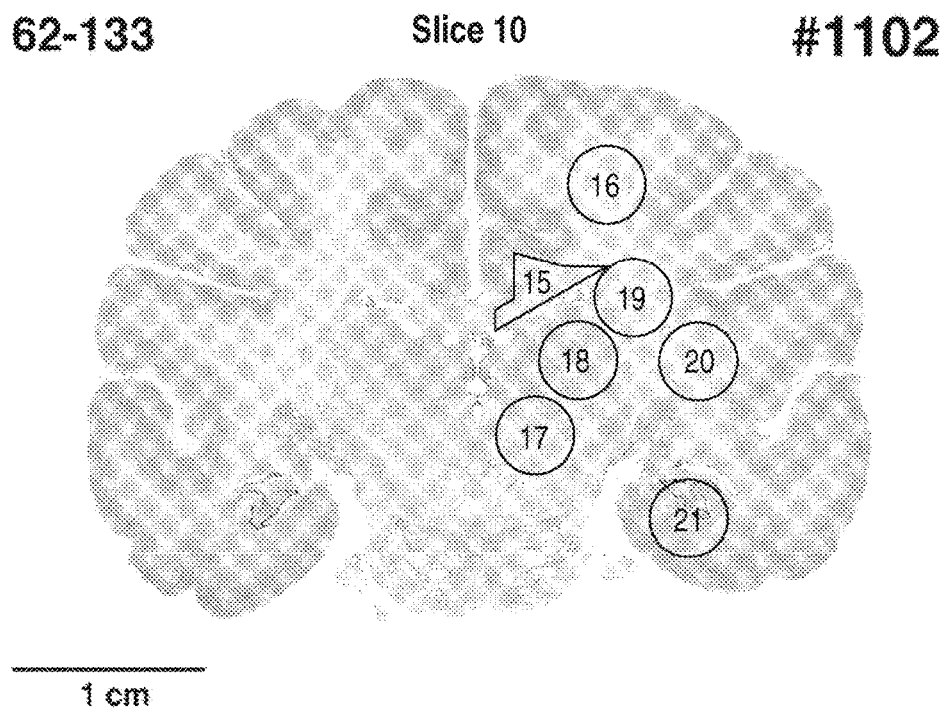
FIG. 41 illustrates exemplary anatomical locations of certain brain punches.
Figure 42:
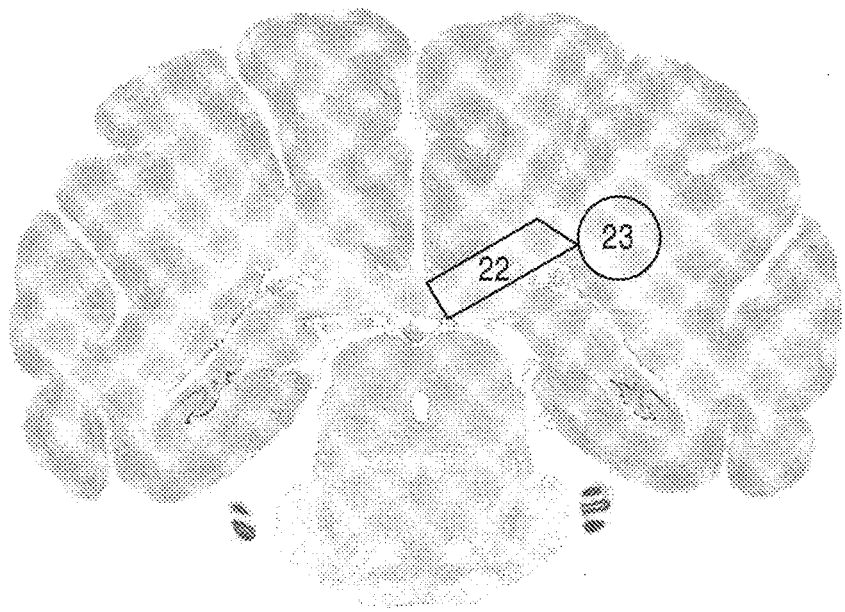
FIG. 42 illustrates exemplary anatomical locations of certain brain punches.
Figure 43:
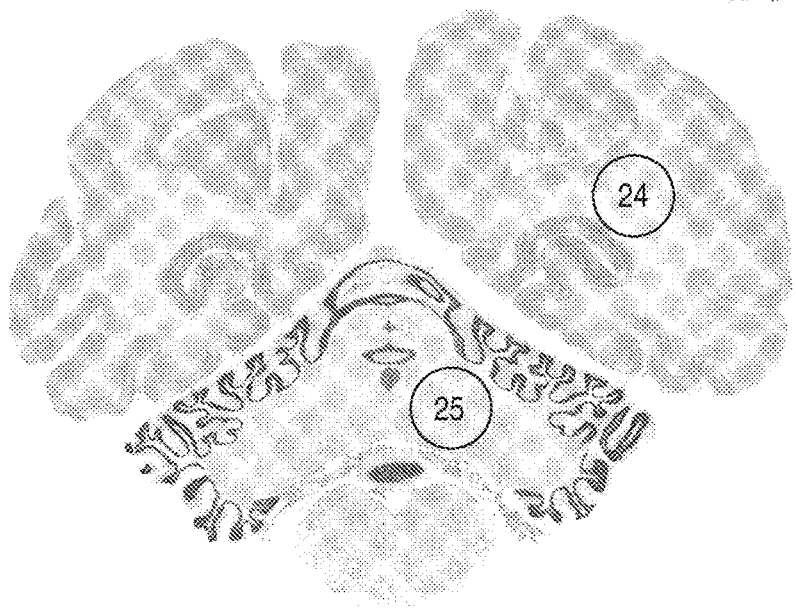
FIG. 43 illustrates exemplary anatomical locations of certain brain punches.
Figure 44A:
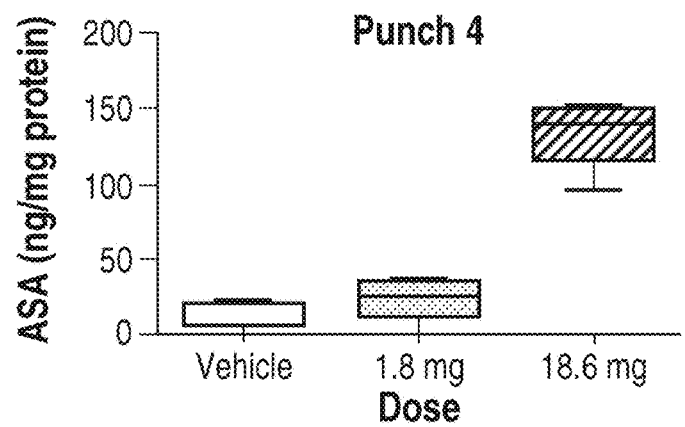
FIG. 44A-G illustrate the concentration of recombinant human arylsulfatase A (rhASA) in extracted tissue punches from the brain tissues of adult and juvenile cynomolgus monkeys administered either a vehicle, 1.8 mg rhASA or 18.6 mg rhASA. Each of FIG. 44A-G corresponds to a region of the brain tissue depicted in FIG. 39.
Figure 44B:
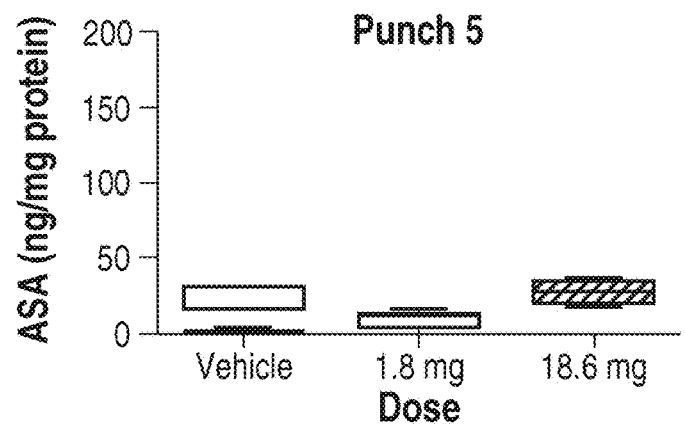
Figure 44C:
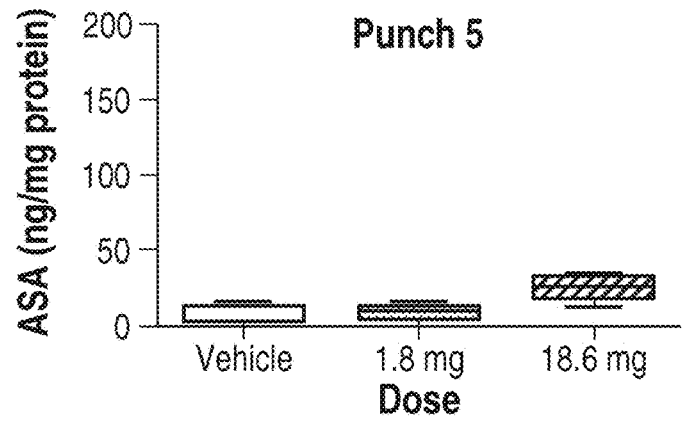
Figure 44D:
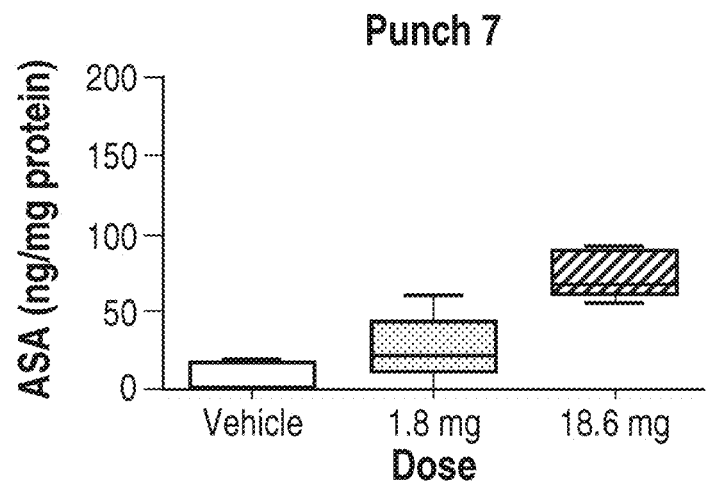
Figure 44E:
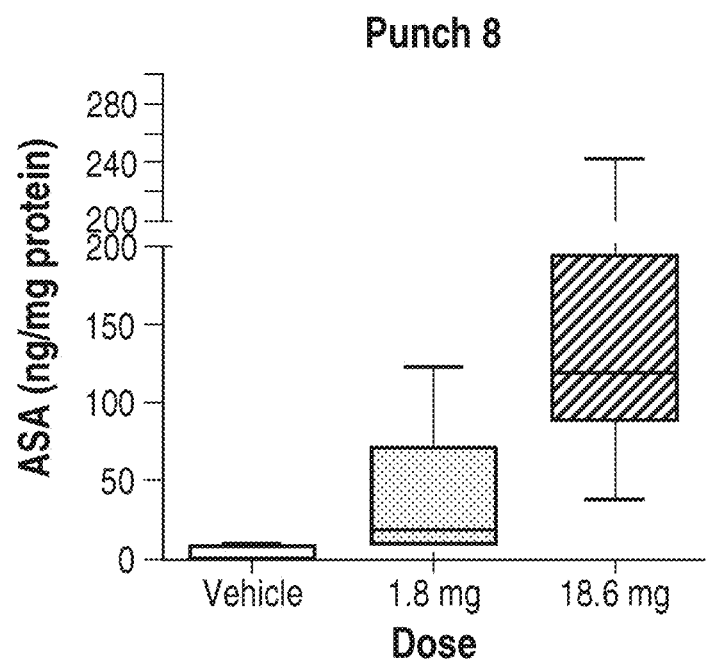
Figure 44F:
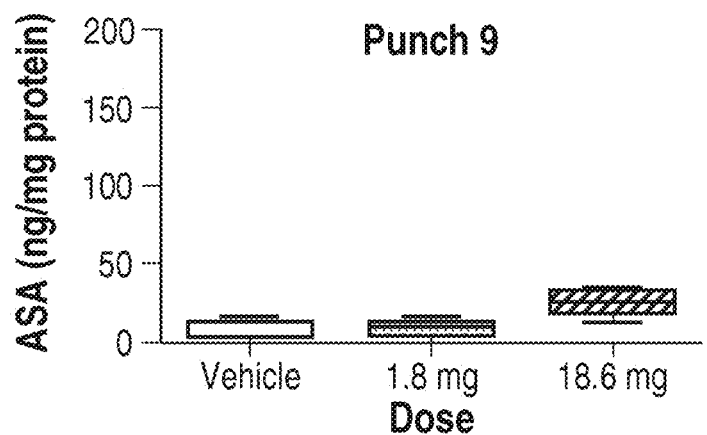
Figure 44G:
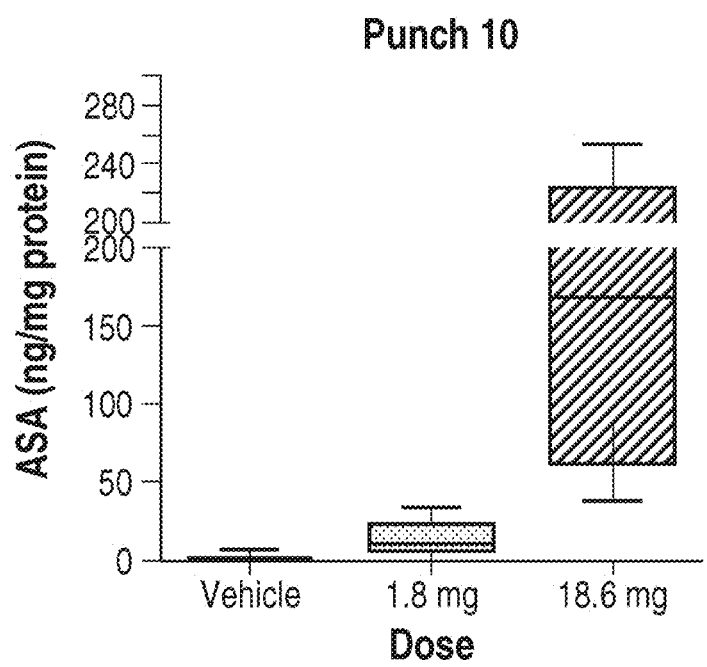
Figure 45A:
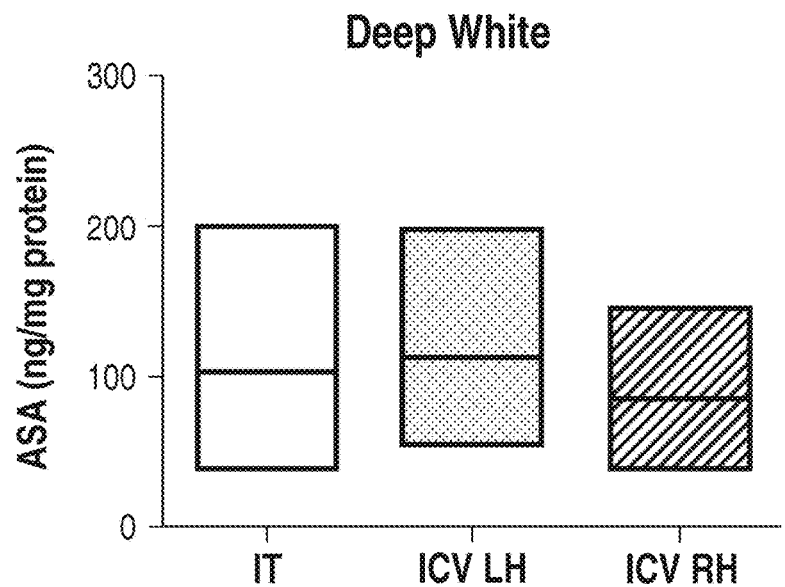
FIGS. 45A and B illustrate exemplary comparison of the concentrations of recombinant human arylsulfatase A (rhASA) detected in the deep white matter (FIG. 45A) or in the deep grey matter (FIG. 45B) brain tissues of adult and juvenile cynomolgus monkeys which were intrathecally (IT) or intracerebroventricularly (ICV) administered rhASA.
Figure 45B:
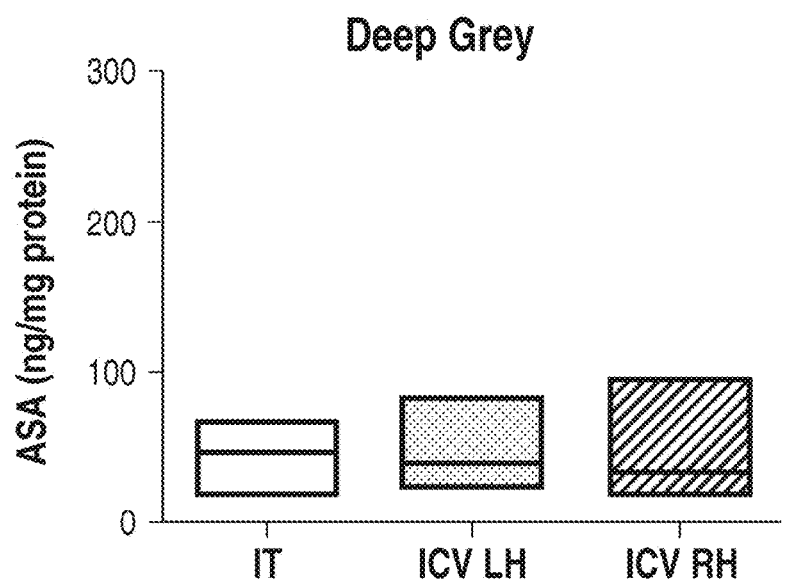
Figure 46A:
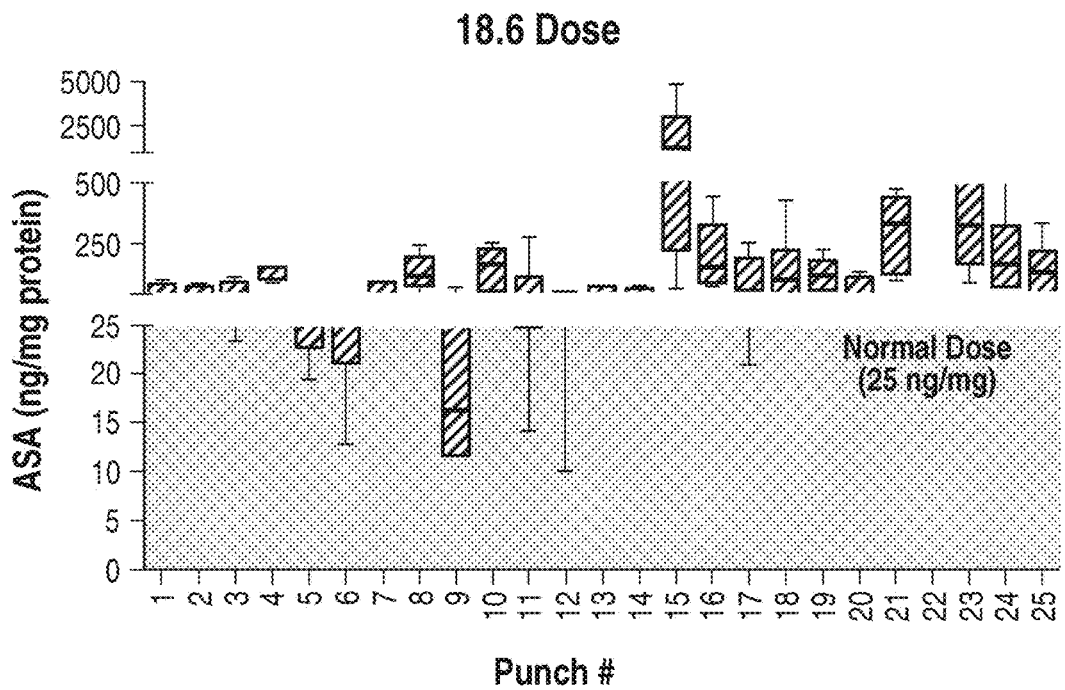
FIG. 46A illustrate concentrations of rhASA detected in several tissue punches obtained from juvenile (<12 months of age) cynomolgus monkeys IT-administered an 18.6 or a 1.8 mg dose of recombinant human arylsulfatase A (rhASA). As illustrated in both FIGS. 40A-B, the concentration of rhASA delivered to the tissues were within, or otherwise exceeded the target therapeutic concentration of 2.5 mg/mg protein. The anatomical regions of brain tissue which correspond to each of the punch numbers depicted in FIG. 46A and FIG. 46B are the: subcortical white matter (1); periventricular white matter and deep white matter (2); subcortical white matter (3); subcortical white matter (4); internal capsule (5); internal capsule caudate nucleus (6); deep white matter (7); subcortical white matter and cortex (8); putamen (9); temporal subcortical white matter and cortex (10), deep grey matter (11), deep grey matter (12), frontal periventricular & subcortical (13); subcortical white matter, cortex superficial perifalxian (14); corpus callosum and pericallosal subcortical white matter (15); deep subcortical white matter (16); deep grey matter (17); deep grey matter (18); periventricular white matter (19); deep subcortical white matter (20); hippocampus (21); corpus callosum (22); deep white matter (23); subcortical white matter, occipital lobe (24); and cerebellar white matter (25).
Figure 46B:
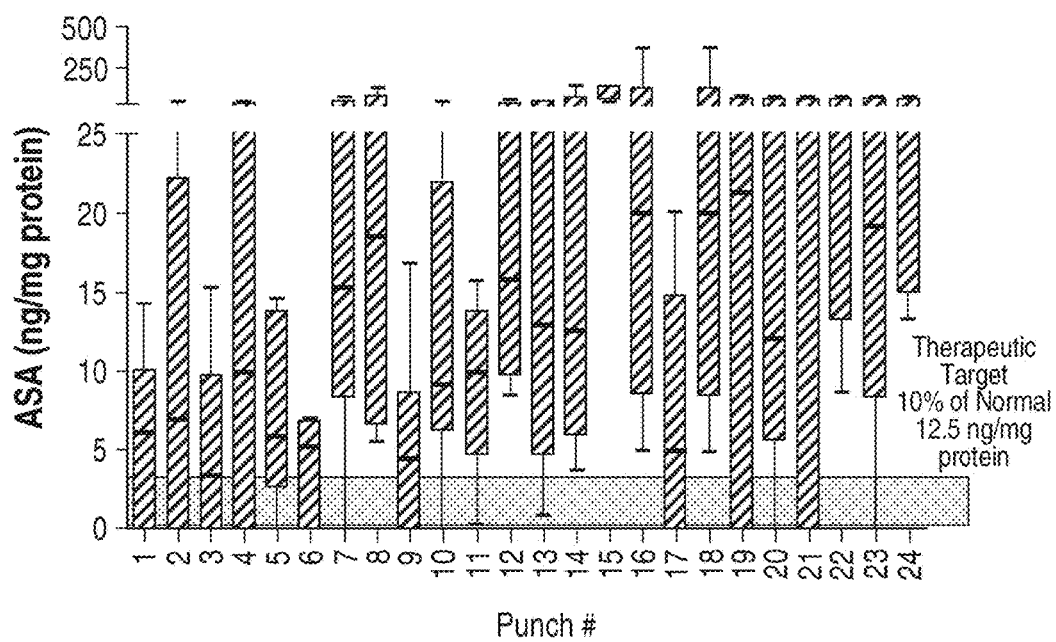
Figure 47C:
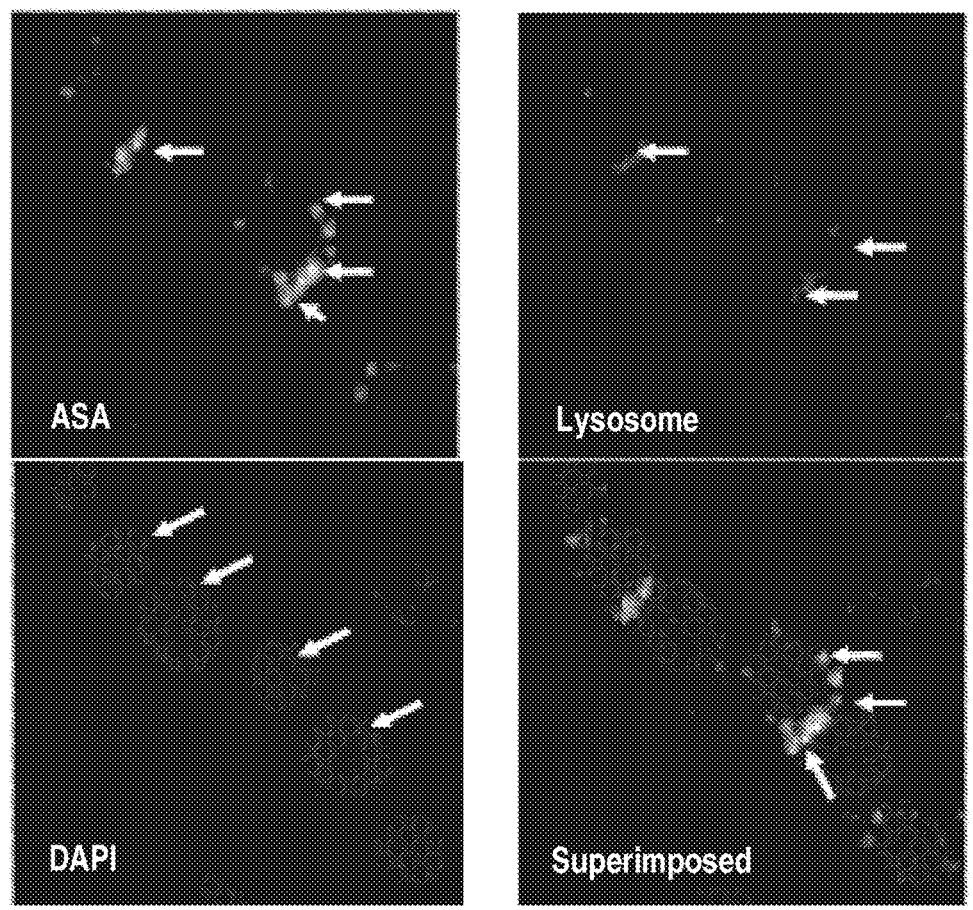
FIG. 47C illustrates that the IT-administered rhASA demonstrated organelle co-localization in the deep white matter tissues of the cynomolgus monkey and in particular in the lysosomes.
Figure 48:
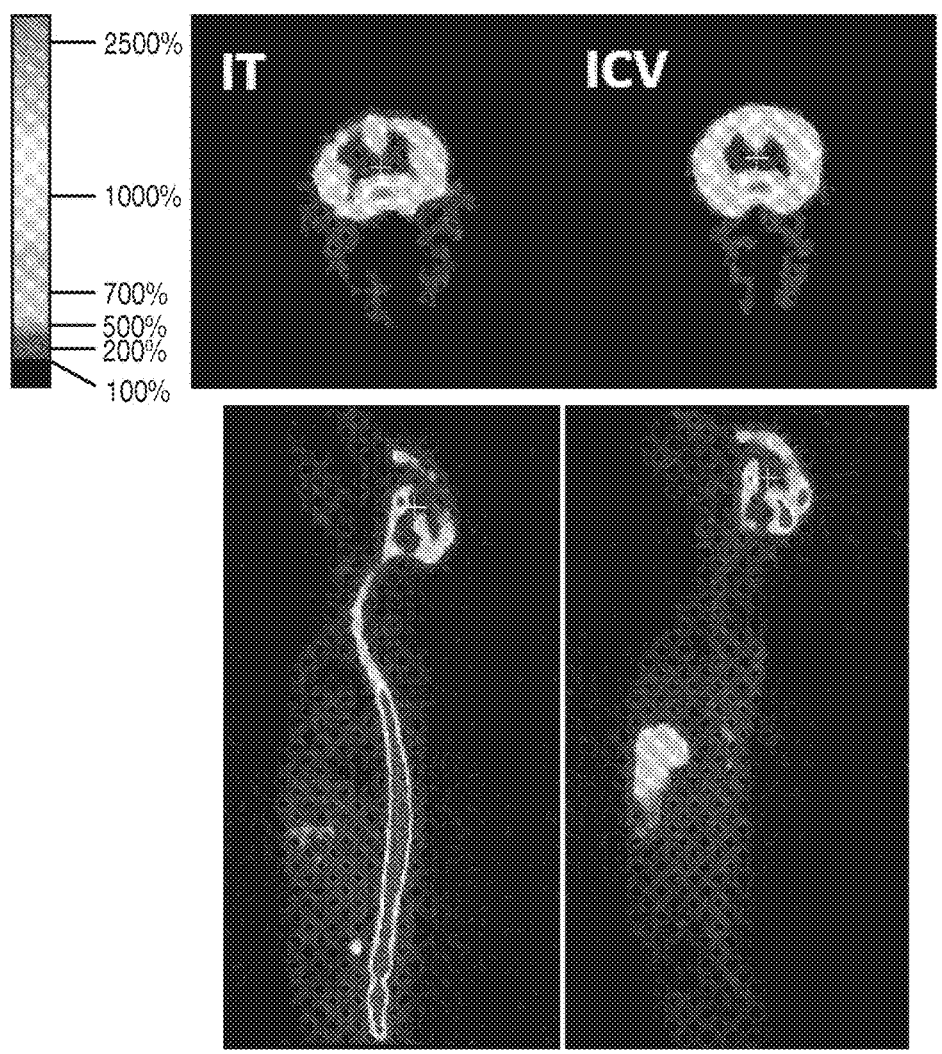
FIG. 48 compares the distribution of $^{124}$I-labeled arylsulfatase A (rhASA) using PET scanning 24 hours following either IT- or ICV-administration of such labeled rhASA to a cynomolgus monkey.
Figure 49:
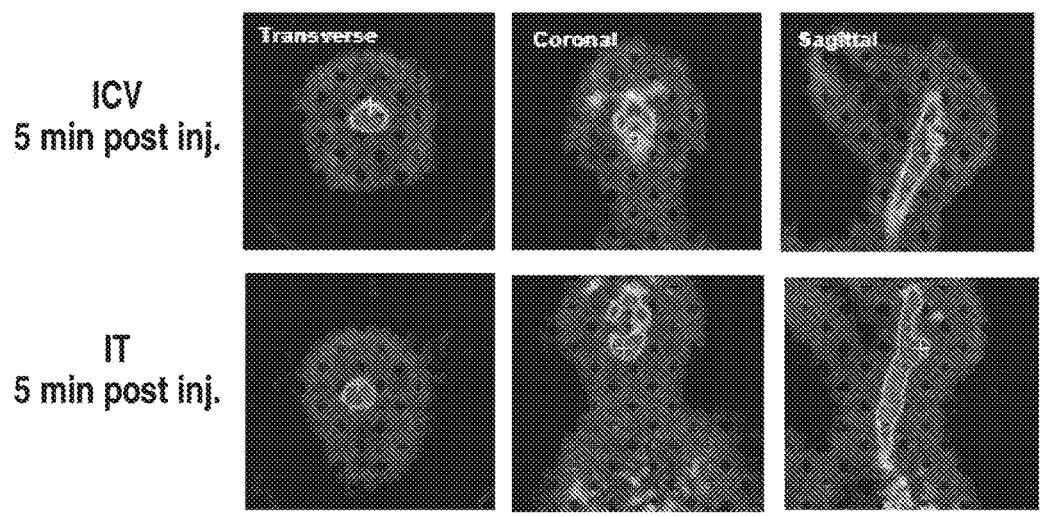
FIG. 49 illustrates the distribution of $^{124}$I-labeled ASA immediately following ICV administration to a cynomolgus monkey, and compares the distribution of IT-administered $^{124}$I-labeled ASA within 2-5 hr. As demonstrated, IT administration delivered the $^{124}$I-labeled ASA to the same initial compartments (cisternae and proximal spine) as that shown for the ICV administration.
Figure 50:
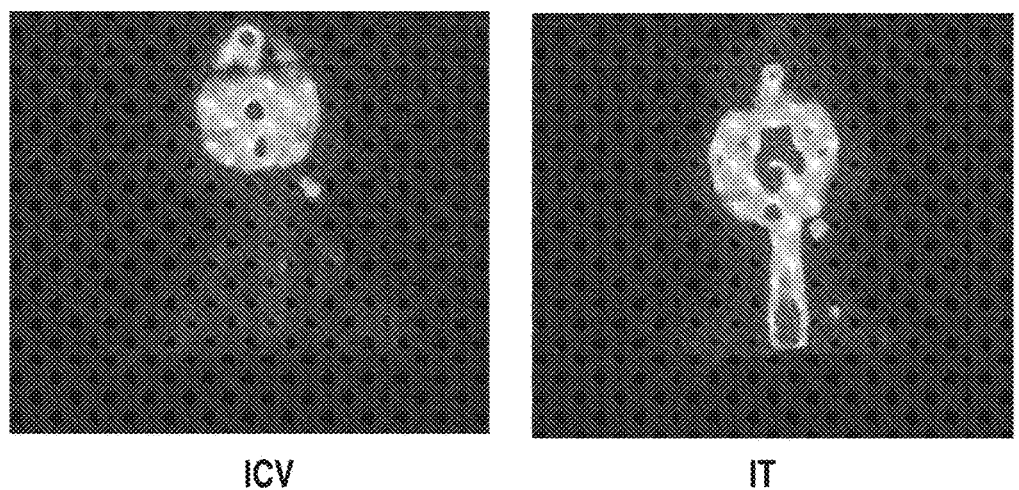
FIG. 50 depicts exemplary ICV and IT administration in a mouse model.
Figure 51:
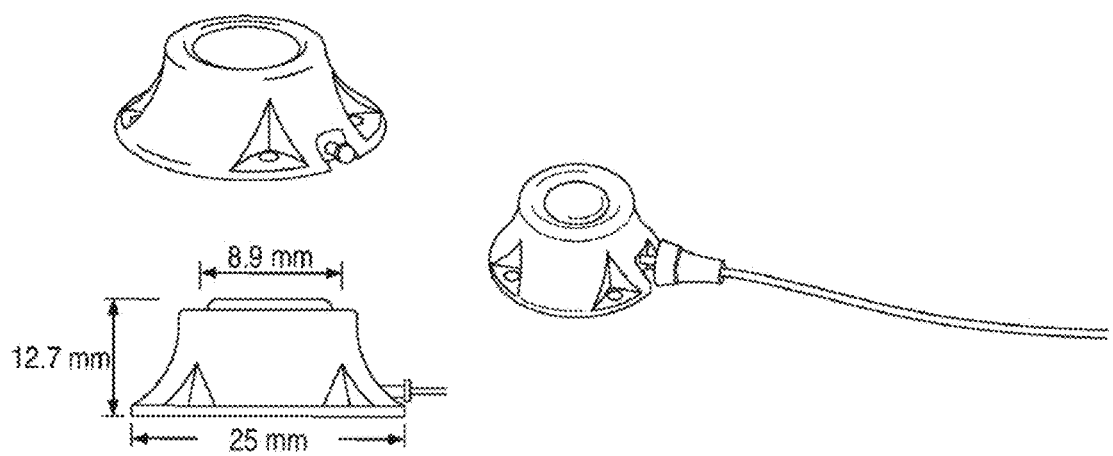
FIG. 51 depicts an exemplary intrathecal drug delivery device (IDDD).
Figure 52:
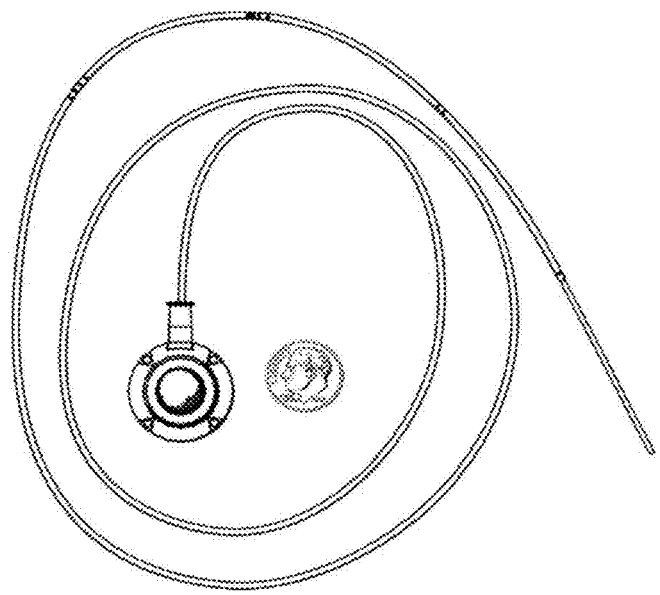
FIG. 52 depicts an exemplary PORT-A-CATH® low profile intrathecal implantable access system.
Figure 53:
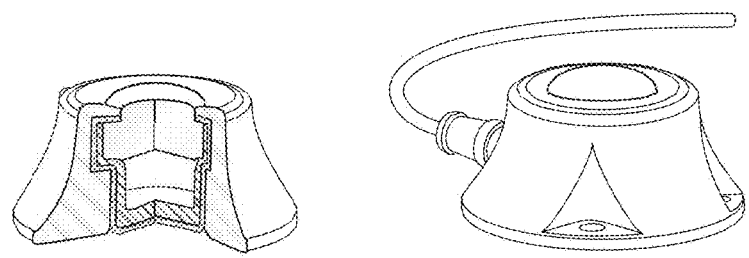
FIG. 53 depicts an exemplary intrathecal drug delivery device (IDDD).
Figure 54:
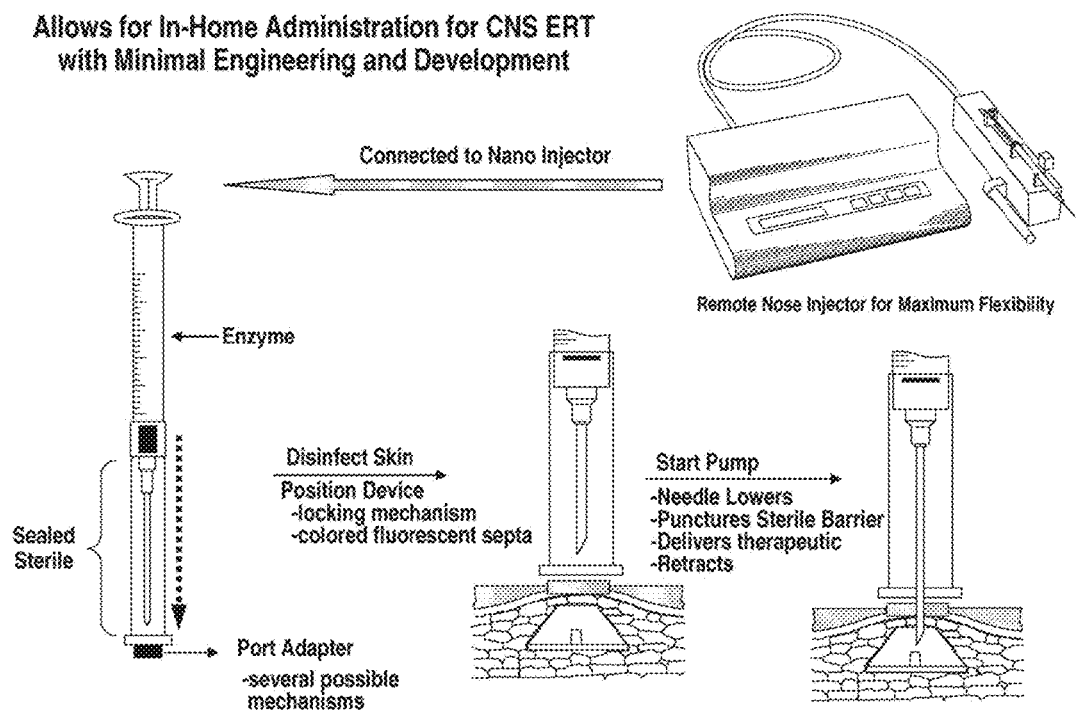
FIG. 54 depicts an exemplary intrathecal drug delivery device (IDDD), which allows for in-home administration for CNS enzyme replacement therapy (ERT).

Liver concentration data is shown in FIG. 37.

Figure 23:
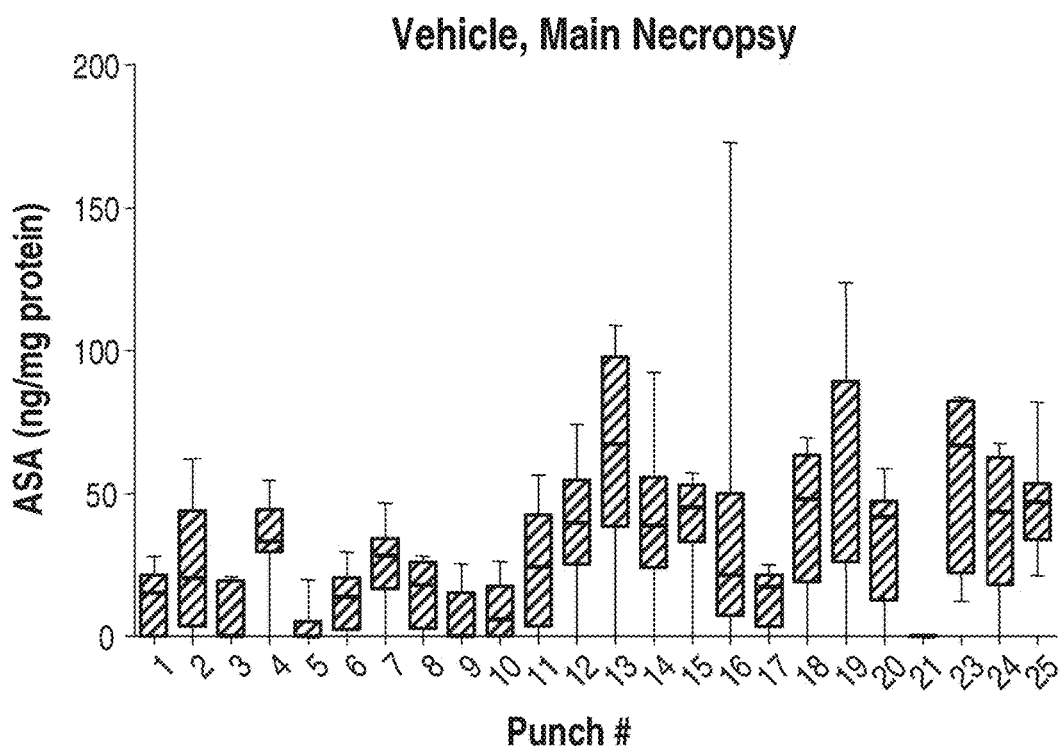
FIG. 23 illustrates exemplary concentration of rhASA in brain punches of vehicle-dosed juvenile cynomolgus monkeys following EOW IT dosing for 6-months-main necropsy.

ASA concentration levels in the liver, spinal cord, and brain of the device and vehicle-dosed control groups were in some cases measurable. The levels in liver and spinal cord were lower than any of the rhASA-treated groups (FIG. 23, FIG. 32, and FIG. 33). The level of rhASA measured in the device control and vehicle-dosed animals represents a cross-reactivity between the anti-rhASA antibody used in the ELISA with the native cynomolgus monkey protein. The reported values in the device control and vehicle tissues do not represent quantitative values for cynomolgus monkey rhASA in the tissues, because the degree of cross-reactivity between the antibody and cynomolgus ASA is not known, and the fact that the assay standards use human ASA. However, without wishing to be bound by any theory, the variation in the levels of ASA detected between device control and vehicle-dosed tissues may be interpreted as demonstrated variability in the relative amounts of cynomolgus ASA in different tissues and anatomical regions.

The ASA levels in spinal cord slices ranged from 160-2352, 1081-6607, and 1893-9252 ng/mg protein in males and 0-3151, 669-6637, and 1404-16424 ng/mg protein in females for the 1.8, 6.0, and 18.6 mg/dose groups, respectively (FIG. 32). Levels of ASA were higher in the lumbar region of the spine than in the cervical region. Levels of ASA protein detected in the liver were dose responsive in the rhASA treated groups and were very low in the vehicle group. Mean ASA levels were 88, 674, and 2424 in males and 140, 462, and 1996 ng/mg protein in females for the 1.8, 6.0, and 18.6 mg/dose groups, respectively (FIG. 33).

Overall, the level of ASA appeared to be dose-related in samples prepared from the spinal cord slices and liver of the rhASA-dosed groups. Many of the brain regions tested demonstrated a clear dose relationship between ASA levels and rhASA administration, while others were more equivocal. In general, ASA levels in the brain increased with rhASA dose.

Example 8: Pharmacokinetic and Biodistribution Study

The objective this study is to evaluate the pharmacokinetic (PK) and biodistribution of various therapeutic replacement enzymes after intrathecal (IT) and intravenous (IV) administration to cynomolgus monkeys.

In this study, a total of twelve male and twelve female cynomolgus monkeys with patent intrathecal-lumbar (IT-L) and intrathecal-cisterna magna (IT-CM) catheters were randomly assigned by body weight into four treatment groups for Phase 1a (IS2 administration) and Phase 1b (ASA administration).

Blood and CSF (from IT-CM catheter) were collected at specified intervals post dosing for both phases. After the last samples were collected from Phase 1a, the animals were allowed a 7-day washout period before initiation of Phase 1b.

After the last samples were collected from Phase 1b, the animals will be allowed a 7-day washout period between initiation of Phase 2. A total of 12 male and female cynomolgus monkeys from Phase 1b were randomly assigned by body weight into 12 treatment groups of IS2 (Groups 1a-6a) and ASA (Groups 1b-6b).

The absolute bioavailability of ASA in serum following IT-L administration is −30 to 40%. In contrast, only 0.5% of the IV dose is bioavailable in CSF.

Exposure to ASA in serum increases in a more than proportional manner following IT-L administration.

Following IT-L administration, exposure to ASA in CSF increases in a less than proportional manner as dose increases. Summaries of PK parameters of rhASA in serum, PK parameters of rhASA in serum in CSF and bioavailability are shown in Tables 45-47.

TABLE 45

SUMMARY PK PARAMETERS OF ASA IN SERUM OF CYNOMOLGUS MONKEYS

| MEAN (CV %) | SERUM ARYLSULFATASE A | | | |
|---|---|---|---|---|
| | ARYLSULFATASE A (PHASE 1B: IV 1 MG/KG) | ARYLSULFATASE A (PHASE 1B: IT-L 1.8 MG) | ARYLSULFATASE A (PHASE 1B: IT-L 6 MG) | ARYLSULFATASE A (PHASE 1B: IT-L 18.6 MG) |
| N | 8 | 6 | 8 | 8 |
| AUC0-T (NG · H/ML) | 10505 (16.9) | 2219 (41.9) | 10352 (31.9) | 17583 (28.2) |
| AUC0-∞ (NG · H/ML) | 11069 (17.2) | NC (NC)B | 9634 (28.9)C | 20789 (27.8)D |
| CMAX (NG/ML) | 11911 (20.0) | 363 (40.4) | 1160 (29.9) | 1621 (25.1) |
| TMAXA (H) | 0.08 (0.08, 0.08) | 4.00 (2.00, 4.00) | 4.00 (1.00, 4.00) | 3.00 (1.00, 4.00) |
| T½ (H) | 6.55 (31.8) | NC (NC)B | 6.77 (21.4)C | 7.40 (32.8)D |
| CL OR CL/F (ML/H) | 261 (17.0) | NC (NC)B | 654 (25.0)C | 944 (25.4)D |
| VZ OR VZ/F (ML) | 2418 (32.4) | NC (NC)B | 6523 (41.3)C | 9686 (25.8)D |

TABLE 46

SUMMARY PK PARAMETERS OF ASA IN CSF OF CYNOMOLGUS MONKEYS

| Mean (CV %) | CSF Arylsulfatase A | | | |
|---|---|---|---|---|
| | Arylsulfatase A (Phase 1b: IV 1 mg/kg) | Arylsulfatase A (Phase 1b: IT-L 1.8 mg) | Arylsulfatase A (Phase 1b: IT-L 6 mg) | Arylsulfatase A (Phase 1b: IT-L 18.6 mg) |
| N | 4 | 6 | 8 | 8 |
| AUC0-t (ng · h/mL) | 1629 (179.8) | 1267266 (86.6) | 5334329 (68.8) | 8028775 (71.2) |
| AUC0-∞ (ng · h/mL) | 8221 (NC)b | 1595942 (79.1)c | 4291829 (84.2)d | 9406664 (64.5)e |
| Cmax (ng/mL) | 69.3 (94.2) | 345167 (48.7) | 1039079 (73.6) | 1841125 (62.8) |
| Tmaxa (h) | 6.00 (1.00, 8.00) | 0.08 (0.08, 4.00) | 0.29 (0.08, 4.00) | 2.04 (0.08, 4.00) |
| t½ (h) | 37.6 (NC)b | 23.6 (68.3)c | 17.1 (31.3)d | 13.4 (29.3)e |
| CL or CL/F (mL/h) | 392 (NC)b | 1.95 (74.1)c | 38.1 (214.8)d * | 3.04 (66.1)e |
| Vz or Vz/F (mL) | 21237 (NC)b | 80.6 (110.4)c | 1090 (215.1)d | 67.6 (81.2)e |

TABLE 47

BIOAVAILABILITY OF ASA IN SERUM AND CSF

| | Absolute Bioavailability Comparison | | |
|---|---|---|---|
| | Arylsulfatase A (Phase 1b: IT-L 1.8 mg) | Arylsulfatase A (Phase 1b: IT-L 6 mg) | Arylsulfatase A (Phase 1b: IT-L 18.6 mg) |
| Fabs (%) | NC | 39.9 | 27.3 |

The bioavailability of ASA in serum following IT-L administration is ~30-40%. In contrast, only 0.5% of the dose administered by IV route is bioavailable in CSF. CSF serum partition is shown in Table 48.

TABLE 48

CSF: SERUM PARTITION
CSF: PLASMA PARTITION

| ARYLSULFATASE A (PHASE 1B: IV 1 MG/KG) | ARYLSULFATASE A (PHASE 1B: IT-L 1.8 MG) | ARYLSULFATASE A (PHASE 1B: IT-L 6 MG) | ARYLSULFATASE A (PHASE 1B: IT-L 18.6 MG) |
|---|---|---|---|
| 0.74 | NC | 445 | 452 |

Example 9—Treatment of MLD Patients

Direct CNS administration through, e.g., IT delivery can be used to effectively treat MLD patients. This example illustrates a multicenter dose escalation study designed to evaluate the safety of up to 3 dose levels every other week (EOW) for a total of 40 weeks of rhASA administered via an intrathecal drug delivery device (IDDD) to patients with late infantile MLD. Various exemplary intrathecal drug delivery devices suitable for human treatment are depicted in FIGS. 45-48.

Up to 20 patients will be enrolled:
Cohort 1: 5 patients (Lowest Dose)
Cohort 2: 5 patients (Intermediate Dose)
Cohort 3: 5 patients (Highest Dose)
5 patients will be randomized to no treatment.

Patients are selected for the study based on inclusion of the following criteria: (1) appearance of first symptoms prior to 30 months of age; (2) ambulatory at the time of screening (defined as the ability to stand up alone and walk forward 10 steps with one hand held); (3) presence of neurological signs at time of screening. Typically, patients' history of hematopoietic stem cell transplantation are excluded.

Safety of ascending doses of rhASA administered by IT injection for 40 weeks in children with late infantile MLD is determined. In addition, the clinical activity of rhASA on gross motor function, and single and repeated-dose pharmacokinetics in serum and concentrations in cerebrospinal fluid (CSF) are assessed.

While certain compounds, compositions and methods described herein have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A method of treating metachromatic leukodystrophy (MLD) disease comprising a step of
administering intrathecally to a human subject in need of treatment a formulation comprising an arylsulfatase A (ASA) protein at a concentration at or greater than 5 mg/mL and at a dose amount of at least 70 mg/kg brain weight, wherein the formulation comprises no greater than 50 mM of phosphate.

2. The method of claim 1, wherein the intrathecal administration of the formulation results in no substantial adverse effects in the subject.

3. The method of claim 2, wherein the intrathecal administration of the formulation results in no substantial adaptive T cell-mediated immune response in the subject.

4. The method of claim 1, wherein the intrathecal administration of the formulation results in delivery of the ASA protein to oligodendrocytes of deep white brain matter.

5. The method of claim 1, wherein the ASA protein is delivered to neurons, glial cells, perivascular cells and/or meningeal cells.

6. The method of claim 1, wherein the ASA protein is further delivered to the neurons in the spinal cord.

7. The method of claim 1, wherein the intrathecal administration of the formulation further results in systemic delivery of the ASA protein in peripheral target tissues.

8. The method of claim 7, wherein the peripheral target tissues are selected from liver, kidney, and/or heart.

9. The method of claim 1, wherein the intrathecal administration of the formulation results in lysosomal localization in target brain tissues, spinal cord neurons and/or peripheral target tissues.

10. The method of claim 1, wherein the intrathecal administration of the formulation results in reduction of sulfatide storage in target brain tissues, spinal cord neurons and/or peripheral target tissues.

11. The method of claim 1, wherein the intrathecal administration of the formulation results in reduced progressive demyelination and axonal loss within the CNS and PNS.

12. The method of claim 1, wherein the intrathecal administration of the formulation results in increased ASA enzymatic activity in target brain tissues, spinal cord neurons and/or peripheral target tissues.

13. The method of claim 1, wherein the intrathecal administration of the formulation results in reduced intensity, severity, or frequency, or delayed onset of at least one symptom or feature of the MLD disease.

14. The method of claim 13, wherein at least one symptom or feature of the MLD disease is increased intracranial pressure, hydrocephalus ex vacuo, accumulated sulfated glycolipids in the myelin sheaths in the central and peripheral nervous system and in visceral organs, progressive demyelination and axonal loss within the CNS and PNS, and/or motor and cognitive dysfunction.

15. The method of claim 1, wherein the intrathecal administration takes place at an interval selected from once every two weeks, once every month, once every two months.

16. The method of claim 1, wherein the intrathecal administration is used in absence of intravenous administration.

17. The method of claim 1, wherein the intrathecal administration is used in absence of concurrent immunosuppressive therapy.

18. The method of claim 1, wherein the formulation comprises NaCl at a concentration of approximately 154 mM, polysorbate 20 at a concentration of approximately 0.005%, and a pH of approximately 6.

19. The method of claim 1, wherein the ASA protein is a synthetic, recombinant, gene-activated or natural enzyme.

20. The method of claim 1, wherein the ASA protein is present at a concentration of at least about 10 mg/mL.

21. The method of claim 1, wherein the ASA protein is present at a concentration of at least about 50 mg/mL.

22. The method of claim 10, wherein the sulfatide storage is reduced by at least 20% as compared to an untreated control.

23. The method of claim 12, wherein the increased ASA enzymatic activity is at least 1-fold as compared to untreated control.

24. The method of claim 12, wherein the increased ASA enzymatic activity is at least 10 nmol/hr/mg.

25. The method of claim 12, wherein the ASA enzymatic activity is increased in the lumbar region.

26. The method of claim 9, wherein the target brain tissue is deep brain tissue at least 4 mm below the surface of the cerebrum.

27. The method of claim 9, wherein the neurons comprise Purkinje cells.

28. The method of claim 1, wherein the formulation is administered in a volume of less than 3 mL.

29. The method of claim 1, wherein the dose amount is of at least 80 mg/kg brain weight.

30. The method of claim 1, wherein the dose amount is of at least 90 mg/kg brain weight.

31. The method of claim 1, wherein the dose amount is of at least 100 mg/kg brain weight.

32. The method of claim 1, wherein the arylsulfatase A (ASA) protein is administered intrathecally at a total amount of 100 mg per injection.

* * * * *

```
                             SEQUENCE LISTING

<160> NUMBER OF SEQ ID NOS: 2

<210> SEQ ID NO 1
<211> LENGTH: 489
<212> TYPE: PRT
<213> ORGANISM: Homo sapiens

<400> SEQUENCE: 1

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
            20                  25                  30

Gln Leu Ala Ala Gly Gly Leu Arg Phe Thr Asp Phe Tyr Val Pro Val
        35                  40                  45

Ser Leu Cys Thr Pro Ser Arg Ala Ala Leu Leu Thr Gly Arg Leu Pro
    50                  55                  60

Val Arg Met Gly Met Tyr Pro Gly Val Leu Val Pro Ser Ser Arg Gly
65                  70                  75                  80

Gly Leu Pro Leu Glu Glu Val Thr Val Ala Glu Val Leu Ala Ala Arg
                85                  90                  95

Gly Tyr Leu Thr Gly Met Ala Gly Lys Trp His Leu Gly Val Gly Pro
            100                 105                 110

Glu Gly Ala Phe Leu Pro Pro His Gln Gly Phe His Arg Phe Leu Gly
        115                 120                 125

Ile Pro Tyr Ser His Asp Gln Gly Pro Cys Gln Asn Leu Thr Cys Phe
    130                 135                 140

Pro Pro Ala Thr Pro Cys Asp Gly Gly Cys Asp Gln Gly Leu Val Pro
145                 150                 155                 160

Ile Pro Leu Leu Ala Asn Leu Ser Val Glu Ala Gln Pro Pro Trp Leu
                165                 170                 175

Pro Gly Leu Glu Ala Arg Tyr Met Ala Phe Ala His Asp Leu Met Ala
            180                 185                 190

Asp Ala Gln Arg Gln Asp Arg Pro Phe Phe Leu Tyr Tyr Ala Ser His
        195                 200                 205

His Thr His Tyr Pro Gln Phe Ser Gly Gln Ser Phe Ala Glu Arg Ser
    210                 215                 220

Gly Arg Gly Pro Phe Gly Asp Ser Leu Met Glu Leu Asp Ala Ala Val
225                 230                 235                 240

Gly Thr Leu Met Thr Ala Ile Gly Asp Leu Gly Leu Leu Glu Glu Thr
                245                 250                 255

Leu Val Ile Phe Thr Ala Asp Asn Gly Pro Glu Thr Met Arg Met Ser
            260                 265                 270

Arg Gly Gly Cys Ser Gly Leu Leu Arg Cys Gly Lys Gly Thr Thr Tyr
        275                 280                 285

Glu Gly Gly Val Arg Glu Pro Ala Leu Ala Phe Trp Pro Gly His Ile
    290                 295                 300

Ala Pro Gly Val Thr His Glu Leu Ala Ser Ser Leu Asp Leu Leu Pro
305                 310                 315                 320

Thr Leu Ala Ala Leu Ala Gly Ala Pro Leu Pro Asn Val Thr Leu Asp
                325                 330                 335
```

Gly Phe Asp Leu Ser Pro Leu Leu Gly Thr Gly Lys Ser Pro Arg
            340                 345                 350

Gln Ser Leu Phe Phe Tyr Pro Ser Tyr Pro Asp Glu Val Arg Gly Val
        355                 360                 365

Phe Ala Val Arg Thr Gly Lys Tyr Lys Ala His Phe Phe Thr Gln Gly
    370                 375                 380

Ser Ala His Ser Asp Thr Thr Ala Asp Pro Ala Cys His Ala Ser Ser
385                 390                 395                 400

Ser Leu Thr Ala His Glu Pro Pro Leu Leu Tyr Asp Leu Ser Lys Asp
                405                 410                 415

Pro Gly Glu Asn Tyr Asn Leu Leu Gly Gly Val Ala Gly Ala Thr Pro
            420                 425                 430

Glu Val Leu Gln Ala Leu Lys Gln Leu Gln Leu Leu Lys Ala Gln Leu
        435                 440                 445

Asp Ala Ala Val Thr Phe Gly Pro Ser Gln Val Ala Arg Gly Glu Asp
    450                 455                 460

Pro Ala Leu Gln Ile Cys Cys His Pro Gly Cys Thr Pro Arg Pro Ala
465                 470                 475                 480

Cys Cys His Cys Pro Asp Pro His Ala
                485

<210> SEQ ID NO 2
<211> LENGTH: 507
<212> TYPE: PRT
<213> ORGANISM: Homo sapiens

<400> SEQUENCE: 2

Met Gly Ala Pro Arg Ser Leu Leu Leu Ala Leu Ala Ala Gly Leu Ala
1               5                   10                  15

Val Ala Arg Pro Pro Asn Ile Val Leu Ile Phe Ala Asp Asp Leu Gly
            20                  25                  30

Tyr Gly Asp Leu Gly Cys Tyr Gly His Pro Ser Ser Thr Thr Pro Asn
        35                  40                  45

Leu Asp Gln Leu Ala Ala Gly Gly Leu Arg Phe Thr Asp Phe Tyr Val
    50                  55                  60

Pro Val Ser Leu Cys Thr Pro Ser Arg Ala Ala Leu Leu Thr Gly Arg
65                  70                  75                  80

Leu Pro Val Arg Met Gly Met Tyr Pro Gly Val Leu Val Pro Ser Ser
                85                  90                  95

Arg Gly Gly Leu Pro Leu Glu Glu Val Thr Val Ala Glu Val Leu Ala
            100                 105                 110

Ala Arg Gly Tyr Leu Thr Gly Met Ala Gly Lys Trp His Leu Gly Val
        115                 120                 125

Gly Pro Glu Gly Ala Phe Leu Pro Pro His Gln Gly Phe His Arg Phe
    130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Gly Cys Asp Gln Gly Leu
                165                 170                 175

Val Pro Ile Pro Leu Leu Ala Asn Leu Ser Val Glu Ala Gln Pro Pro
            180                 185                 190

Trp Leu Pro Gly Leu Glu Ala Arg Tyr Met Ala Phe Ala His Asp Leu
        195                 200                 205

Met Ala Asp Ala Gln Arg Gln Asp Arg Pro Phe Phe Leu Tyr Tyr Ala

-continued

```
                    210                 215                 220
        Ser His His Thr His Tyr Pro Gln Phe Ser Gly Gln Ser Phe Ala Glu
        225                 230                 235                 240

Arg Ser Gly Arg Gly Pro Phe Gly Asp Ser Leu Met Glu Leu Asp Ala
                        245                 250                 255

Ala Val Gly Thr Leu Met Thr Ala Ile Gly Asp Leu Gly Leu Leu Glu
                        260                 265                 270

Glu Thr Leu Val Ile Phe Thr Ala Asp Asn Gly Pro Glu Thr Met Arg
                    275                 280                 285

Met Ser Arg Gly Gly Cys Ser Gly Leu Leu Arg Cys Gly Lys Gly Thr
                    290                 295                 300

Thr Tyr Glu Gly Gly Val Arg Glu Pro Ala Leu Ala Phe Trp Pro Gly
        305                 310                 315                 320

His Ile Ala Pro Gly Val Thr His Glu Leu Ala Ser Ser Leu Asp Leu
                        325                 330                 335

Leu Pro Thr Leu Ala Ala Leu Ala Gly Ala Pro Leu Pro Asn Val Thr
                    340                 345                 350

Leu Asp Gly Phe Asp Leu Ser Pro Leu Leu Leu Gly Thr Gly Lys Ser
                    355                 360                 365

Pro Arg Gln Ser Leu Phe Phe Tyr Pro Ser Tyr Pro Asp Glu Val Arg
                    370                 375                 380

Gly Val Phe Ala Val Arg Thr Gly Lys Tyr Lys Ala His Phe Phe Thr
        385                 390                 395                 400

Gln Gly Ser Ala His Ser Asp Thr Thr Ala Asp Pro Ala Cys His Ala
                        405                 410                 415

Ser Ser Ser Leu Thr Ala His Glu Pro Pro Leu Leu Tyr Asp Leu Ser
                    420                 425                 430

Lys Asp Pro Gly Glu Asn Tyr Asn Leu Leu Gly Gly Val Ala Gly Ala
                    435                 440                 445

Thr Pro Glu Val Leu Gln Ala Leu Lys Gln Leu Gln Leu Leu Lys Ala
                    450                 455                 460

Gln Leu Asp Ala Ala Val Thr Phe Gly Pro Ser Gln Val Ala Arg Gly
        465                 470                 475                 480

Glu Asp Pro Ala Leu Gln Ile Cys Cys His Pro Gly Cys Thr Pro Arg
                        485                 490                 495

Pro Ala Cys Cys His Cys Pro Asp Pro His Ala
                        500                 505
```